(12) United States Patent
Wischik et al.

(10) Patent No.: US 6,953,794 B2
(45) Date of Patent: Oct. 11, 2005

(54) INHIBITION OF TAU-TAU ASSOCIATION

(75) Inventors: Claude Michel Wischik, Cambridge (GB); Patricia Carol Edwards, Cambridge (GB); Charles Robert Harrington, Cambridge (GB); Martin Roth, Cambridge (GB); Aaron Klug, Cambridge (GB)

(73) Assignee: The University Court of the University of Aberdeen, Aberdeen (GB)

(*) Notice: Subject to any disclaimer, the term of this patent is extended or adjusted under 35 U.S.C. 154(b) by 372 days.

(21) Appl. No.: 10/107,181

(22) Filed: Mar. 28, 2002

(65) Prior Publication Data

US 2002/0168687 A1 Nov. 14, 2002

Related U.S. Application Data

(62) Division of application No. 08/913,915, filed as application No. PCT/EP96/01307 on Mar. 25, 1996, now Pat. No. 6,376,205.

(30) Foreign Application Priority Data

Mar. 27, 1995 (GB) ............................................. 9506197

(51) Int. Cl.$^7$ .............................................. A61K 31/54
(52) U.S. Cl. ................................................... 514/224.8
(58) Field of Search ..................................... 514/224.8

(56) References Cited

U.S. PATENT DOCUMENTS 5,827,644 A * 10/1998 Floyd et al. .................... 435/2

FOREIGN PATENT DOCUMENTS

| DE | A-4430091 | 2/1996 |
|---|---|---|
| EP | 0 457 295 A2 | 11/1991 |
| EP | 0 457 295 A3 | 11/1991 |
| WO | WO-A-9303177 | 2/1993 |
| WO | WO-A-9303369 | 2/1993 |
| WO | 9311231 | 6/1993 |
| WO | WO-A-9311231 | 6/1993 |
| WO | WO-A-9505466 | 2/1995 |
| WO | WO-A-9604915 | 2/1996 |

OTHER PUBLICATIONS

R. Lai, The Role of Abnormal Phosphorylation of Tau Protein in the Development of Neurofibrillary Pathology in Alzheimer's Disease, pp. 1–243.
Dissertation by Claude Wischik, p. 182, 189, 233 and 234, No date available.
C. Wischik, "Molecular Neuropathology of Alzheimer's Disease" (1989), pp. 44–70.
Garcini et al., *Biochemical and Biophysical Research Communications,* Self Assembly of Microtubule Associated Protein TAU into Filaments Resembling those found in Alzheimer Disease (1986), pp. 790–797.
Garcini et al., *J. Biochem.* 102, No. 6, "In Vitro Conditions for the Self–Polymerization of the Microtubule–Associated Protein, Tau Factor" (1987), pp. 1415–1421.
Garcini et al., *Elsevier Science Publishers B.V.,* "Tau Factor Polymers are Similar to Paired Helical Filaments of Alzheimer's Disease" (1988), pp. 150–154.
Ksiezak–Reding and Yen, *Neuron,* vol. 6, pp. 717–728, Structural Stability of Paired Helical Filaments Requires Microtubule Binding Domains of Tau: A Model for SelfAssociation (1991).
Wille et al., *J. Cell Biol.,* 118 (1992) 573–584, Alzheimerlike paired helical filaments and antiparallel dimers formed from microtubule–associated protein tau in vitro.
Lee et al., untitled, *Science,* vol. 251 (1992).
Kziezak–Reding and Wall, *Neurobiology of Aging,* vol. 15, No. 1, pp. 11–18. "Mass and Physical Dimensions of Two Distinct Populations of Paired Helical Filaments" (1993).
Wischik et al., *Proc. Natl. Acad. Sci. USA,* vol. 85, pp. 4506–4510 (1988) "Isolation of a fragment of tau derived from the core of the paired helical filament of Alzheimer disease".
Wischik et al., *Proc. Natl. Acad. Sci. USA,* vol. 85, pp. 4884–4888, "Structural characterization of the core of the paired helical filament of Alzheimer disease" (1988).
Wischik et al., *Proc. Natl. Acad. Sci. USA,* vol. 93, pp. 11213–11218 (1996) "Selective inhibition of Alzheimer disease–like tau aggregation by phenothiazines".
Ksiezak–Reding, Assembled tau filaments differ from native paired helical filaments as determiend by scanning transmission electron microscopy (STEM) (1998), pp. 86–98.
Mena et al., *Journal of Neuropathology and Experimental Neurology,* "A Progressive Depsotion of Paired Helical Filaments (PHF) in the Brain Characterizes the Evolution of Dementia in Alzheimer's Disease" (1991), pp. 474–490.
Mena et al., *Acta Neuropathol.,* Monitoring Pathological Assembly of tau and β–Amyloid Proteins in Alzheimer's Disease (1994), pp. 50–56.
Mena et al., *Acta Neuropathol,* "Staging the Pathological Assembly of Truncated tau Protein into Paired Helical Filaments in Alzheimer's Disease" (1995), pp. 633–641.
C.M. Wischik et al. "Quantitative Analysis of Tau Protein in Paried Helical Filament Preparations: Implications for the Role of Tau Protein Phosphorylation in PHF Assembly in Alzheimer's Disease", *Neurobiology of Aging,* vol. 16, No. 3, pp. 409–431, 1995.

(Continued)

*Primary Examiner*—Raymond J. Henley, III
(74) *Attorney, Agent, or Firm*—Bacon & Thomas

(57) ABSTRACT

A composition and use thereof for the prophylaxis or treatment of Alzheimer's disease, motor neurone disease, Lewy body disease, Pick's disease or progressive supranuclear palsy. The composition includes an agent which modulates or inhibits tau-tau association and which does not inhibit tau-tubulin binding. In the method the agent is administered to an individual in order to achieve the desired therapeutic effect. Preferably the agent which is administered is a phenothiazine compound.

9 Claims, 29 Drawing Sheets

OTHER PUBLICATIONS

C.M. Wischik et al., "Author's Response to Commentaries", pp. 423–431, No date available.

C.M. Wischik et al., "Structure, Biochemistry and Molecular Pathogenesis of Paired Helical Filaments in Alzheimer's Disease", *Pathobiology of Alzheimer's Disease*, pp. 10–39, 1995.

V.M.–Y. Lee et al., "A68: A Major Subunit of Paired Helical Filaments and Derivatized Forms of Normal Tau", *Science*, vol. 251, pp. 675–678, No date available.

M. Goedert et al., "Tau Proteins of Alzheimer Paired Helical Filaments: Abnormal Phosphorylation of All Six Brain Isoforms", *Neuron*, vol. 8, pp. 159–168, Jan. 1992.

C.M. Wischik et al., "Structural Characterization of the Core of the Paired Helical Filament of Alzheimer's Disease", *Proc. Natl. Acad. Sci. USA*, vol. 85, pp. 4884–4888, Jul. 1998.

C.M. Wischik et al., "Isolation of a Fragment of Tau Derived From the Core of the Paired Helical Filament of Alzheimer's Disease", *Proc. Natl. Acad. Sci. USA*, vol. 85, pp. 4506–4510, Jun. 1998.

R. Jakes et al., "Identification of 3– and 4–repeat Tau Isoforms Within The PHF in Alzheimer's Disease", *The EMBO Journal*, vol. 10, No. 10, pp. 2725–2729, 1991.

M. Novak et al., "Molecular Characterization of the Minimal Protease Resistant Tau Unit of the Alzheimer's Disease Paired Helical Filament", *The EMBO Journal*, vol. 12, No. 1, pp. 365–370, 1993.

S.–H. Yen et al., "Alzheimer's Neurofibrillary Tangles Contain Unique Epitopes and Epitopes in Common With the Heat–Stable Microtubule Associated Proteins Tau and $MAP_2$", *AJP*, vol. 126, Jan. 1987.

J.P. Brion et al., "Characterization of a Partial cDNA Specific for the High Molecular Weight Microtubule–Associated Protein MAP2 That Encodes Epitopes Shared with Paired Helical Filaments of Alzheimer's Disease", *Dementia*, 1990:1:304–315.

M.W. Klymkowsky, "Weaving a Tangled Web: the Interconnected Cytoskeleton", *Nature Cell Biology*, vol. 1, No. 5, p. E121 (1999).

R. Brandt, "Cytoskeletal Mechanisms of Axon Outgrowth and Pathfinding", *Cell Tissue Res.*, (1998) 292:181–189.

D. van Rossum et al., "Cytoskeletal Dynamics in Dendritic Spines: Direct Modulation By Glutamate Receptors?", *Trends Neurosci*, (1992) 22, 290–295.

R. Sato–Harada et al., "Microtubule–associated Proteins Regulate Microtubule Function as the Track for Intracellular Membrane Organelle Transports", *Cell Structure and Function*, 21:283–295 (1996).

A. Grover et al., "5' Splice Site Mutations in Tau Associated with the Inherited Dementia FTDP–17 Affect a Stem–Loop Structure That Regulates Alternative Splicing of Exon 10*", *The Journal of Biological Chemistry*, vol. 274, No. 21, May 21 Issue, pp. 15134–15143, 1999.

M. Hutton et al., "Association of Missense of 5'–splice–site Mutations in Tau With the Inherited Dementia FTDP–17", *Nature*, vol. 393, pp. 702–705, Jun. 18, 1998.

T. Ishihara et al., "Age–Dependent Emergence and Progression of a Tauopathy in Transgenic Mice Overexpressing the Shortest Human Tau Isoform", *Neuron*, vol. 24, pp. 751–762, Nov. 1999.

A. Harada et al., "Altered Microtubule Organization In Small–Calibre Axons of Mice Lacking Tau Protein", *Letters to Nature*, No date available.

I. Tint et al., "Acute Inactivation of Tau Has No Effect on Dynamics of Microtubules in Growing Axons of Cultured Sympathetic Neurons", *The Journal of Neuroscience*, Nov. 1, 1998, 18(21):8661–8673.

S. Kaech et al., "Cytoskeletal Plasticity in Cells Expressing Neuronal Microtubule–Associated Proteins", *Neuron*, vol. 17, 1189–1199, Dec. 1996.

R. Y. K. Lai et al., "Examination of Phosphorylated Tau Protein as a PHF–Precursor at Early State Alzheimer's Disease", *Neurobiology of Aging*, vol. 16, No. 3, pp. 433–445, 1995.

E. Braak et al., "Alzheimer's Disease: Transiently Developing Dendritic Changes in Pyramidal Cells of Sector CA1 of the Ammon's Horn", *Acta Neuropathol.*, (1997) 93:323–325.

B. H. Anderton et al., "Dentritic Changes in Alzheimer's Disease and Factors That May Underlie These Changes", *Prog. Neurobiol.*, Aug. 1998; 55(6):595–609.

C. Smith et al., "The molecular pathology of Alzheimer's disease: are we any closer to understanding the neurodegenerative process?", *Neuropathology and Applied Neurobiology*, vol. 20, 1994, pp. 322–338, XP002002176.

C.R. Harrington et al., "Measurement of Distinct Immunochemical Presentations of Tau Protein in Alzheimer Disease", pp. 5842–5846, Proc. Natl. Acad. Sci., vol. 88, Jul. 1991.

C.R. Harrington et al., "Competitive ELISA for the Measurement of Tau Protein in Alzheimer's Disease", pp. 261–271, Journal of Immunological Methods, 134 (1990).

R. Day, "How to Write and Publish a Scientific Paper", ISI Press, Philadelphia, PA., pp. 124–127, 1983.

Wischik et al., PNAS 93:11213–11218, 1996.

Friedhoff et al., Biochemistry, 37:10223–10230, 1998.

Friedhoff et al., PNAS, 95:15712–15717, 1998.

Pedrotti, et al., Biochemistry, p. 33:8798–8806, 1994.

Garcia de Ancos et al., Journal of Biological Chemistry, 268(11):7976–7982, 1993.

Wischik, Claude M., Thesis "The Structure and Biochemistry of Paired Helical Filaments in Alzheimer's Disease", Part I and II, No date available.

Wischik et al., "Subunit Structure of Paired Helical Filaments in Alzheimer's Disease", p. 1905–1913, 1985.

* cited by examiner

Fig. 3A
A [R1,R3,R4]

```
                              D L K N V K S K I G S T E N
 L K H O P G G G K V Q I V Y K P V D L S K V T S K C G S L G N
 I H H K P G G G Q V E V K S E K L D F KDR V O S K I G S L D N
 I T H V P G G G N K K I E T H K L t f ren a k a k t d h g a e
```

(SEQ ID NO: 1)

Fig. 3B
B [R1,R2,R3]

```
                              D L K N V K S K I G S T E N
 L K H O P G G G K V Q I I N K K L D L S N V O S K C G S K D N
 I K H V P G G G S V Q I V Y K P V D L S K V T S K C G S L G N
 I H H K P G G G Q V E V K S E K L D F KDR V O S K I G S L D N?
```

(SEQ ID NO: 2)

Fig. 3C
C [R2,R3,R4]

```
                              D L S N V O S K C G S K D N
 I K H V P G G G S V Q I V Y K P V D L S K V T S K C G S L G N
 I H H K P G G G Q V E V K S E K L D F KDR V O S K I G S L D N
 I T H V P G G G N K K I E T H K L t f ren a k a k t d h g a e
```

(SEQ ID NO: 3)

Proto-assembly of tau

Truncation of N- and C-terminal domains

Minimal core tau unit dimer

Further binding of tau

Further truncation

Building up of core PHF

Fig. 11
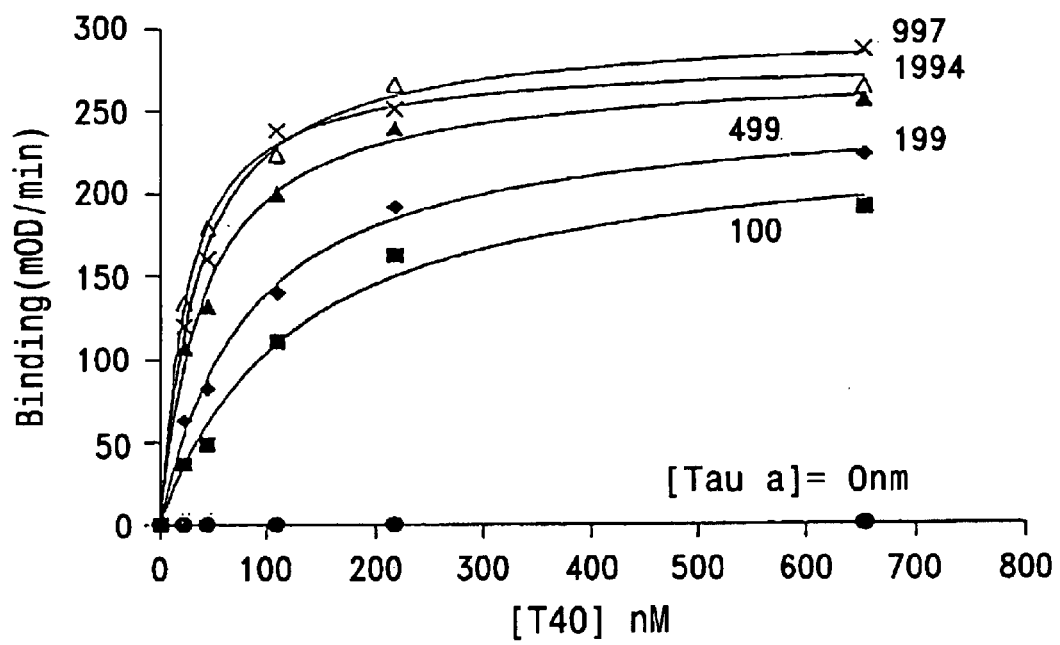
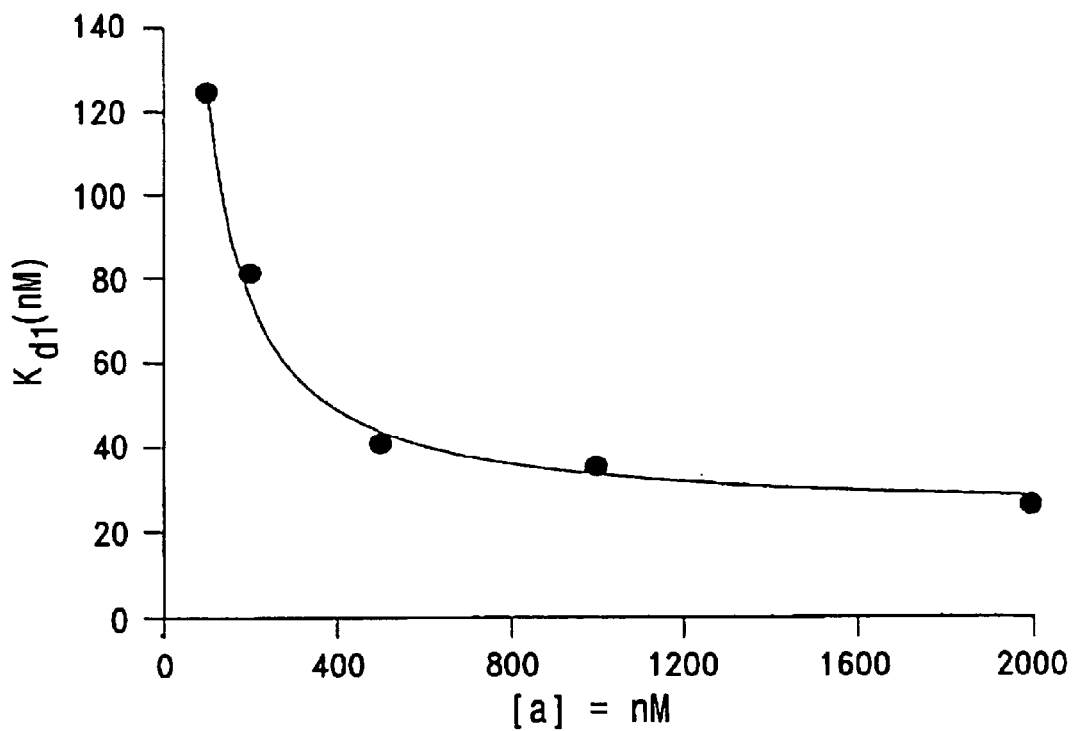

Fig. 13
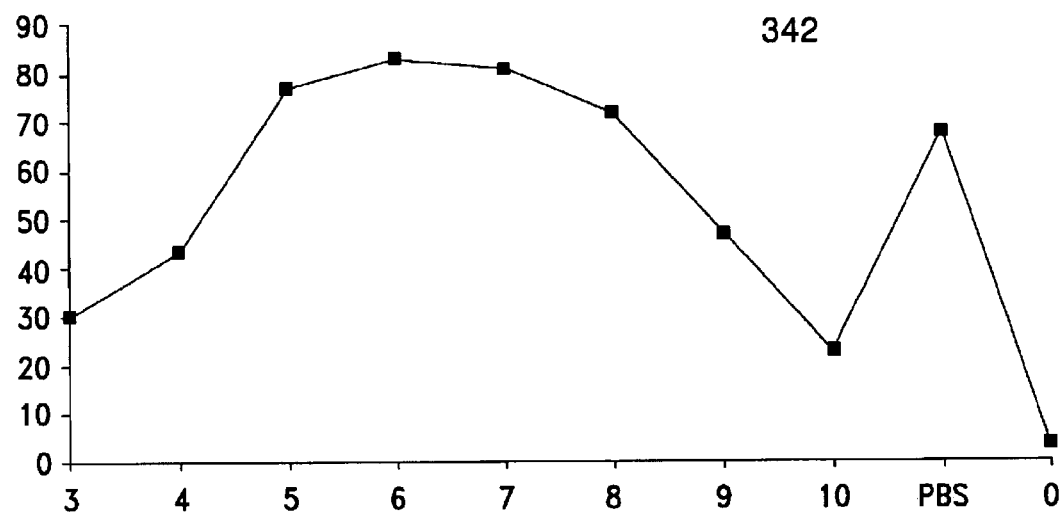
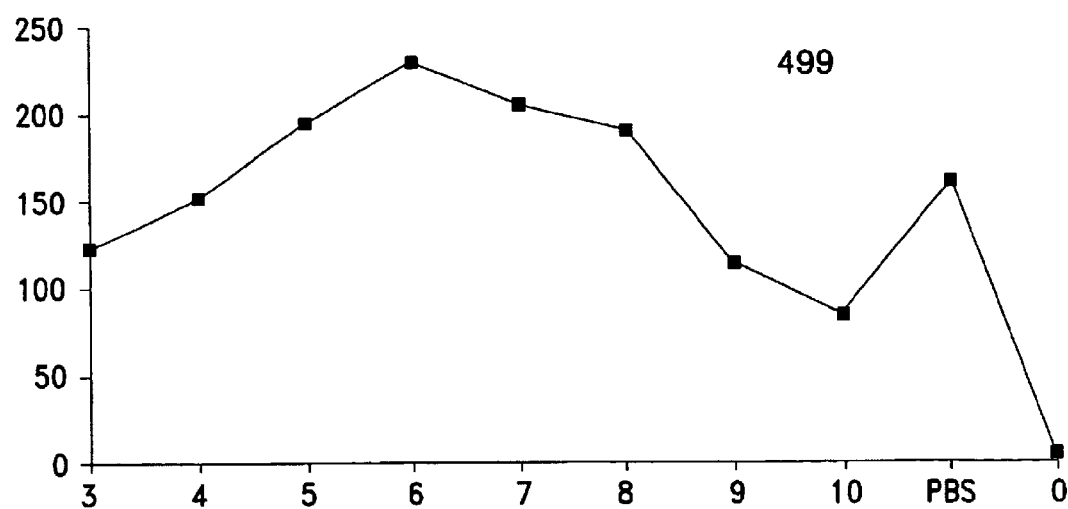

| Solid Phase | Aqueous Phase | | Newborn |
| --- | --- | --- | --- |
| | T40 | T40P | |
| dGA | 25 nM | 252 nM | No Binding |
| Newborn | 19 nM | 627 nM | |
| NewbornP | 754 nM | 969 nM | |

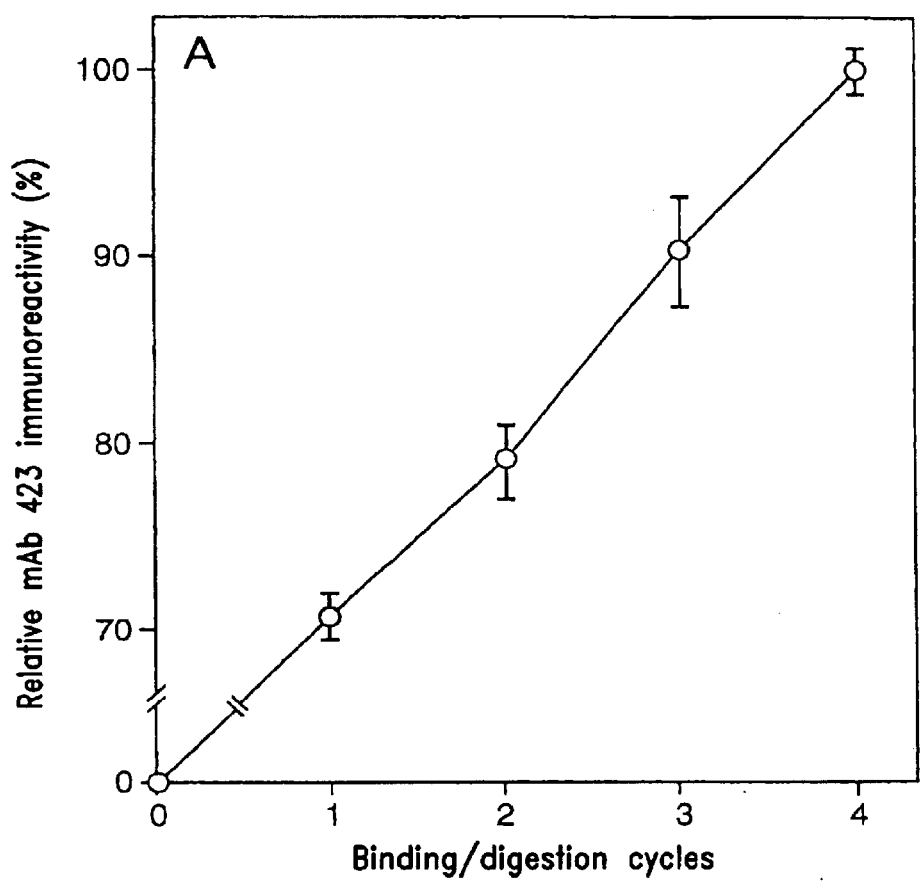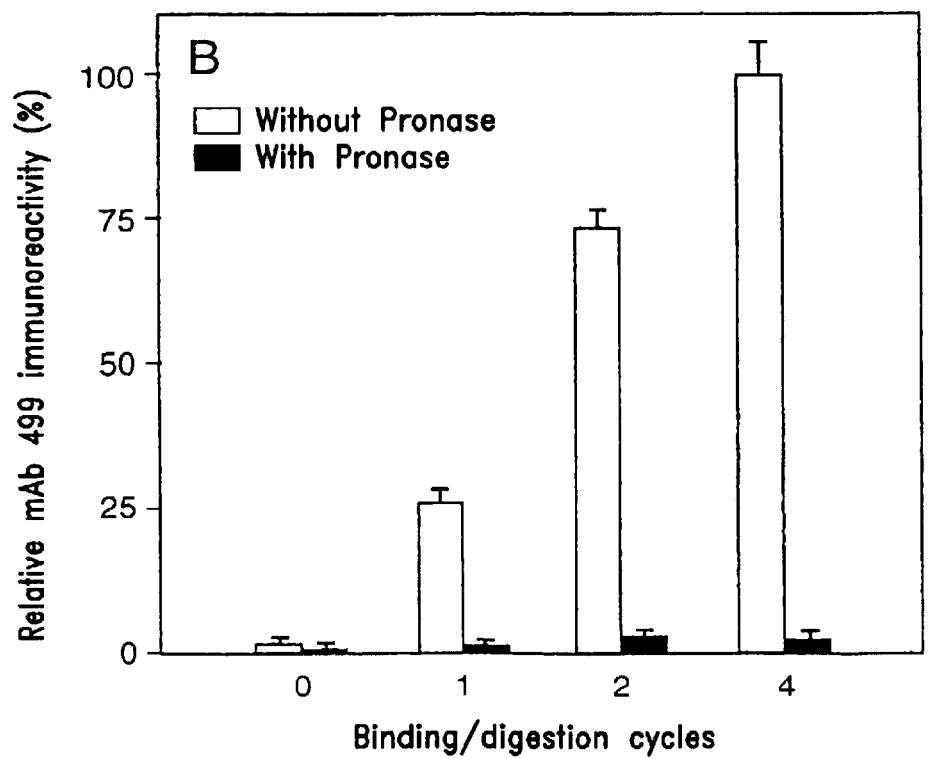
Fig. 18

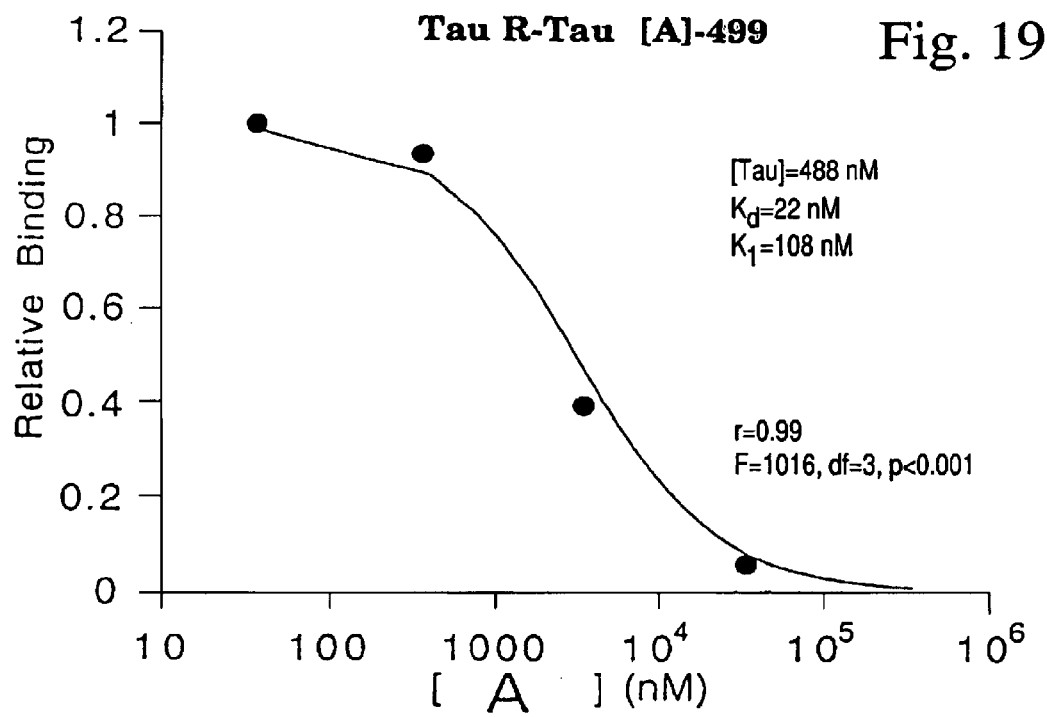
Fig. 19
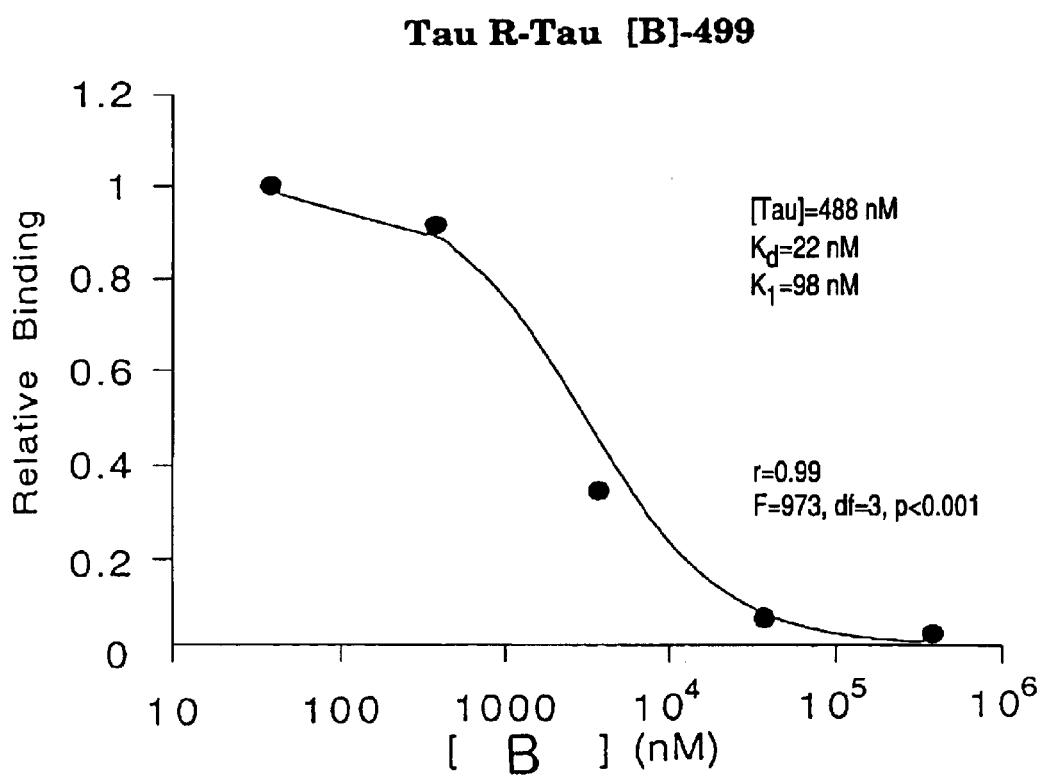

Fig. 21A (SEQ. ID. NOS: 4 and 5)

```
ATG GCT GAG CCC CGC CAG GAG TTC GAA GTG ATG GAA GAT CAC GCT GGG
Met Ala Glu Pro Arg Gln Glu Phe Glu Val Met Glu Asp His Ala Gly
 1               5                  10                  15
ACG TAC GGG TTG GGG GAC AGG AAA GAT CAG GGG GGC TAC ACC ATG CAC
Thr Tyr Gly Leu Gly Asp Arg Lys Asp Gln Gly Gly Tyr Thr Met His
              20                  25                  30
CAA GAC CAA GAG GGT GAC ACG GAC GCT GGC CTG AAA GAA TCT CCC CTG
Gln Asp Gln Glu Gly Asp Thr Asp Ala Gly Leu Lys Glu Ser Pro Leu
          35                  40                  45
CAG ACC CCC ACT GAG GAC GGA TCT GAG GAA CCG GGC TCT GAA ACC TCT
Gln Thr Pro Thr Glu Asp Gly Ser Glu Glu Pro Gly Ser Glu Thr Ser
     50                  55                  60
GAT GCT AAG AGC ACT CCA ACA GCG GAA GAT GTG ACA GCA CCC TTA GTG
Asp Ala Lys Ser Thr Pro Thr Ala Glu Asp Val Thr Ala Pro Leu Val
65                  70                  75                  80
GAT GAG GGA GCT CCC GGC AAG CAG GCT GCC GCG CAG CCC CAC ACG GAG
Asp Glu Gly Ala Pro Gly Lys Gla Ala Ala Ala Gln Pro His Thr Glu
              85                  90                  95
ATC CCA GAA GGA ACC ACA GCT GAA GAA GCA GGC ATT GGA GAC ACC CCC
Ile Pro Glu Gly Thr Thr Ala Glu Glu Ala Gly Ile Gly Asp Thr Pro
             100                 105                 110
AGC CTG GAA GAC GAA GCT GCT GGT CAC GTG ACC CAA GCT CGC ATG GTC
Ser Leu Glu Asp Glu Ala Ala Gly His Val Thr Gln Ala Arg Met Val
         115                 120                 125
AGT AAA AGC AAA GAC GGG ACT GGA AGC GAT GAC AAA AAA GCC AAG GGG
Ser Lys Ser Lys Asp Gly Thr Gly Ser Asp Asp Lys Lys Ala Lys Gly
     130                 135                 140
GCT GAT GGT AAA ACG AAG ATC GCC ACA CCG CGG GGA GCA GCC CCT CCA
Ala Asp Gly Lys Thr Lys Ile Ala Thr Pro Arg Gly Ala Ala Pro Pro
145                 150                 155                 160
GGC CAG AAG GGC CAG GCC AAC GCC ACC AGG ATT CCA GCA AAA ACC CCG
Gly Gln Lys Gly Gln Ala Asn Ala Thr Arg Ile Pro Ala Lys Thr Pro
             165                 170                 175
CCC GCT CCA AAG ACA CCA CCC AGC TCT GGT GAA CCT CCA AAA TCA GGG
Pro Ala Pro Lys Thr Pro Pro Ser Ser Gly Glu Pro Pro Lys Ser Gly
         180                 185                 190
GAT CGC AGC GGC TAC AGC AGC CCC GGC TCC CCA GGC ACT CCC GGC AGC
Asp Arg Ser Gly Tyr Ser Ser Pro Gly Ser Pro Gly Thr Pro Gly Ser
     195                 200                 205
CGC TCC CGC ACC CCG TCC CTT CCA ACC CCA CCC ACC CGG GAG CCC AAG
Arg Ser Arg Thr Pro Ser Leu Pro Thr Pro Pro Thr Arg Glu Pro Lys
210                 215                 220
```

Fig. 21B

```
AAG GTG GCA GTG GTC CGT ACT CCA CCC AAG TCG CTG TCT TCC GCC AAG
Lys Val Ala Val Val Arg Thr Pro Pro Lys Ser Leu Ser Ser Ala Lys
225             230             235             240

AGC CGC CTG CAG ACA GCC CCC GTG CCC ATG CCA GAC CTG AAG AAT GGC
Ser Arg Leu Gln Thr Ala Pro Val Pro Met Pro Asp Leu Lys Asn Gly
            245             250             255

AAG TCC AAG ATC GGC TCC ACT GAG AAC CTG AAG CAC CAG CCG GGA GGC
Lys Ser Lys Ile Gly Ser Thr Glu Asn Leu Lys His Gln Pro Gly Gly
            260             265             270

GGG AAG GTG CAG ATA ATT AAT AAG AAG CTG GAT CTT AGC AAC GTC CAG
Gly Lys Val Gln Ile Ile Asn Lys Lys Leu Asp Leu Ser Asn Val Gln
            275             280             285

TCC AAG TGT GGC TCA AAG GAT AAT ATC AAA CAG GTC CCG GGA GGC GGC
Ser Lys Cys Gly Ser Lys Asp Asn Ile Lys Gln Val Pro Gly Gly Gly
    290             295             300

AGT GTG CAA ATA GTC TAC AAA CCA GTT GAC CTG AGC AAG GTG ACC TCC
Ser Val Gln Ile Val Tyr Lys Pro Val Asp Leu Ser Lys Val Thr Ser
305             310             315             320

AAG TGT GGC TCA TTA GGC AAC ATC CAT CAT AAA CCA GGA GGT GGC CAG
Lys Cys Gly Ser Leu Gly Asn Ile His His Lys Pro Gly Gly Gly Gln
            325             330             335

GTG GAA GTA AAA TCT GAG AAG CTT GAC TTC AAG GAC AGA GTC CAG TCG
Val Glu Val Lys Ser Glu Lys Leu Asp Phe Lys Asp Arg Val Gln Ser
            340             345             350

AAG ATT GGG TCC CTG GAC AAT ATC ACC CAC GTC CCT GGC GGA GGA AAT
Lys Ile Gly Ser Leu Asp Asn Ile Thr His Val Pro Gly Gly Gly Asn
            355             360             365

AAA AAG ATT GAA ACC CAC AAG CTG ACC GTC CGC GAG AAC GCC AAA GCC
Lys Lys Ile Glu Thr His Lys Leu Thr Val Arg Glu Asn Ala Lys Ala
    370             375             380

AAG ACA GAC CAC GGG GCG GAG ATC GTG TAC AAG TCG CCA GTG GTG TCT
Lys Thr Asp His Gly Ala Glu Ile Val Tyr Lys Ser Pro Val Val Ser
385             390             395             400

GGG GAC ACG TCT CCA CGG CAT CTC AGC AAT GTC TCC TCC ACC GGC AGC
Gly Asp Thr Ser Pro Arg His Leu Ser Asn Val Ser Ser Thr Gly Ser
            405             410             415

ATT GAC ATG GTA GAC TCG CCC CAG CTC GCC ACG CTA GCT GAC GAG GGG
Ile Asp Met Val Asp Ser Pro Gln Leu Ala Thr Leu Ala Asp Glu Gly
            420             425             430

TCT GCC TCC CTG GCC AAG CAG GGT TTG TGA
Ser Ala Ser Leu Ala Lys Gln Gly Leu ***
            435             440
```

Fig. 22

```
         NdeI
5' catag
atcaaacacgtcccgggaggcggcagtgtgcaaatagtctacaaaccagttgacctgagcaag
     (M)
     IleLysHisValProGlyGlyGlySerValGlnIleValTyrLysProValAspLeuSerLys gtgacctccaagtgtggctcattaggcaacatccatcataaaccaggaggtggccaggtggaagtaaaatct
ValThrSerLysCysGlySerLeuGlyAsnIleHisHisLysProGlyGlyGlyGlnValGluValLysSer gagaagcttgacttcaaggacagagtccagtcgaagattgggtccctggacaatatcacccacgtccctggc
GluLysLeuAspPheLysAspArgValGlnSerLysIleGlySerLeuAspAsnIleThrHisValProGly ggaggaaataaaaagattgaaacccacaagctgaccttccgcgagaacgccaaagccaagacagaccacggg
GlyGlyAsnLysLysIleGluThrHisLysLeuThrPheArgGluAsnAlaLysAlaLysThrAspHisGly gcggag tgagaattc ... 3'
AlaGlu *** EcoRI
(SEQ ID NO: 6)
```

Primers used for dGAE (Novak et al. 1993)

a) sense primer

```
                NdeI
5'..gcccgggccccatagatcaaacacgtcccgggaggcggcagtgtgcaa..3'
(SEQ ID NO: 7)
``` b) anti-sense primer

```
                EcoRI
5'..agattacagaattctcactccgccccgtggtctgtcttggctttggc..3'
(SEQ ID NO: 8)
```

Fig. 24A
Toluidine Blue O 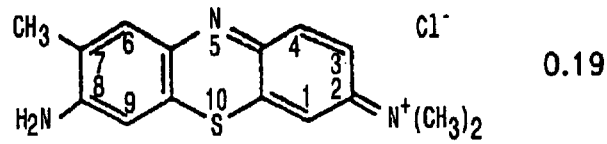 0.19
Thionine 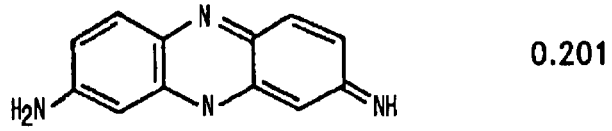 0.201
Azure A 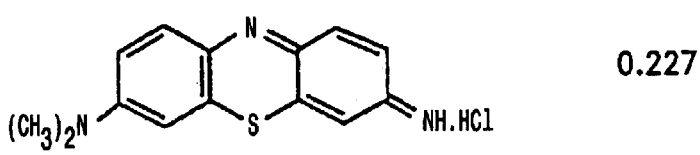 0.227
Azure B 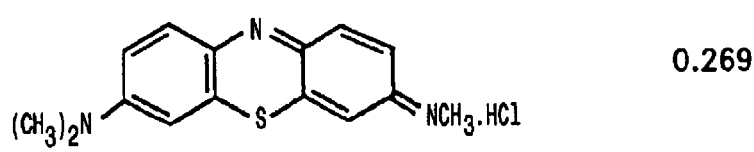 0.269
1,9-Dimethyl-Methylene Blue 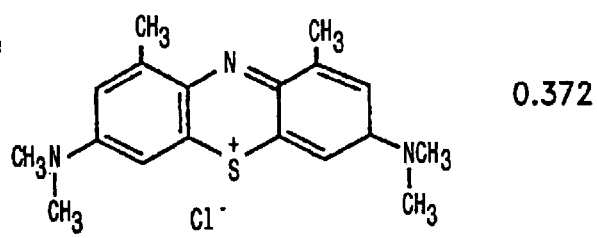 0.372
Acriflavine HCl 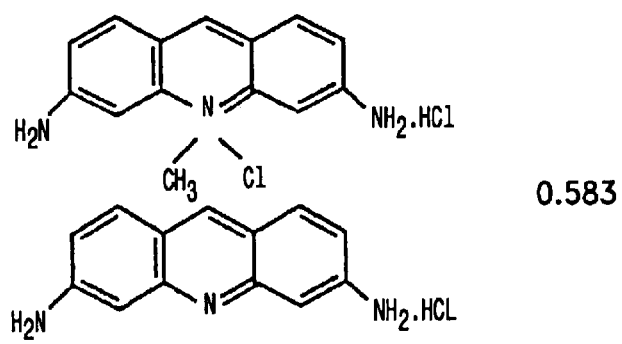 0.583
Vitamin K₂ 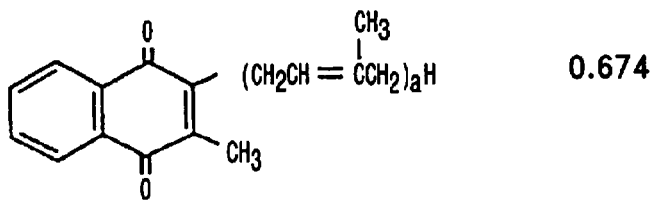 0.674

Fig. 24B
| Compound | Structure | Value |
|---|---|---|
| Neutral red | 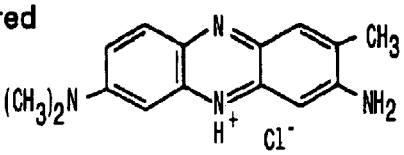 | 0.687 |
| Pyronine Y | 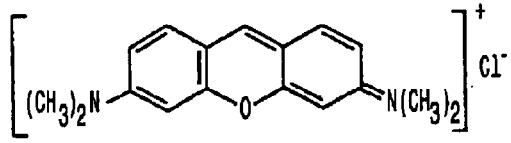 | 0.783 |
| Riboflavine | 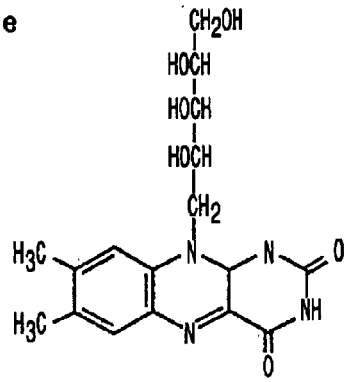 | 0.837 |
| Phenosafranin | 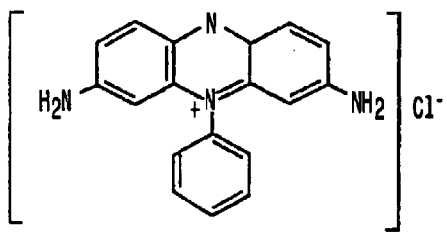 | 0.886 |
| Tacrine | 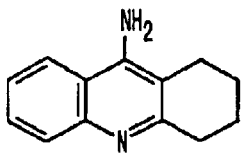 | 0.886 |
| Disopyramide | 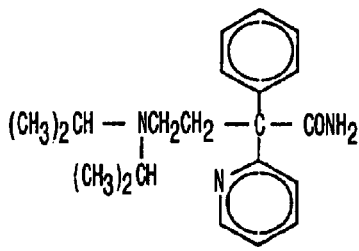 | 0.936 |
| α-Tocopherol acid succinate | 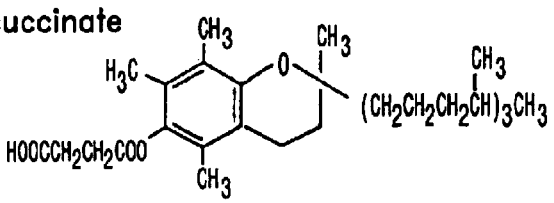 | 0.952 |

Fig. 24C
| Compound | Structure | Value |
|---|---|---|
| Folic Acid | 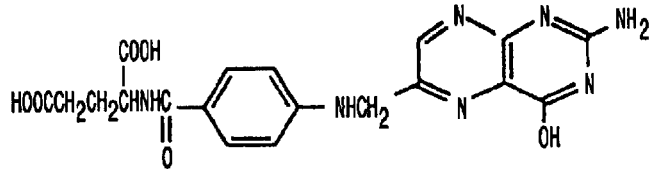 | 0.964 |
| Chlorpromazine | 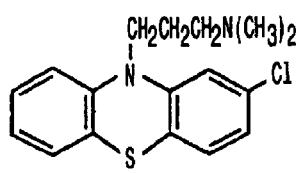 | 0.982 |
| Thiamine HCl | 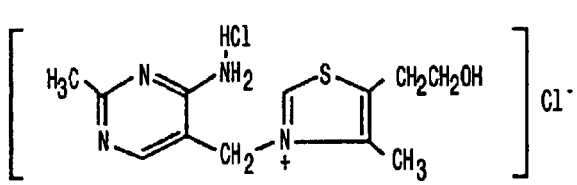 | 0.985 |
| Methylene Blue | 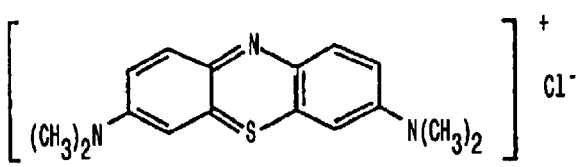 | 0.992 |
| Gallocyanine | 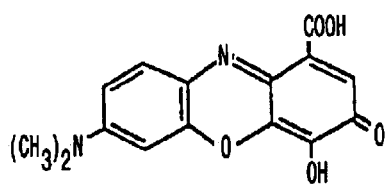 | 0.997 |
| Rhodamine B | 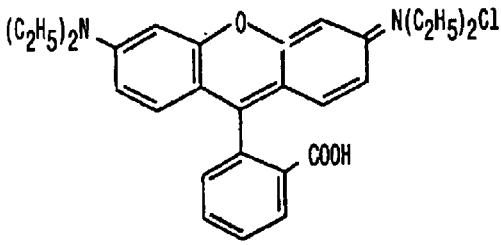 | 1.015 |
| Phenothiazine | 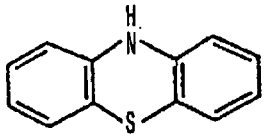 | 1.04 |
| Menadione | 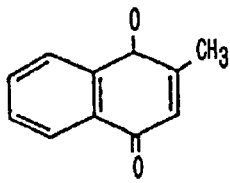 | 1.042 |

Fig. 24D
Vitamin B₁₂ 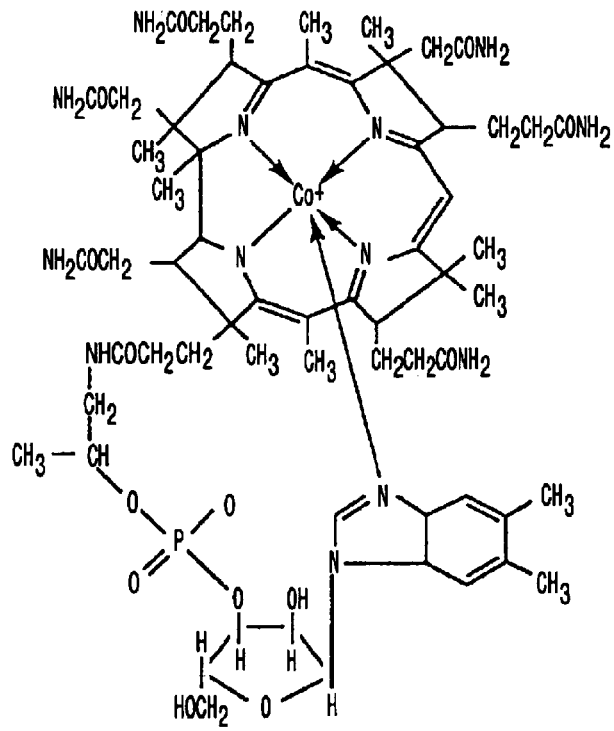 1.098
Pyridoxine Hydrochloride 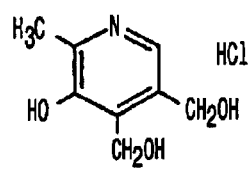 1.192
Celestine Blue 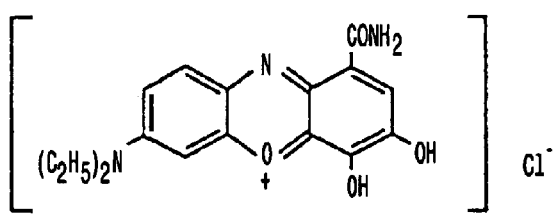 1.259
Carbamazepine 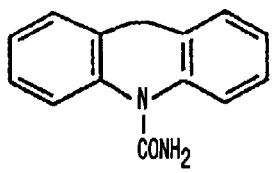 1.51

Fig. 26

```
Human tau (SEQ ID NO: 9)                      D L K N V K S K I G S I E N
Mouse MAP2 (SEQ ID NO: 10)                                              D L K H O P G G G K V Q I I N K K L D L S N V Q S K C G S K D N
 I Y     K       Q R L       I F   K     R I K H V P G G G S V Q I V Y K P V D L S K V T S K C G S L G N
 S A     N           T K I       H             K 338 340 342
 I H H K P G G G Q V E V K S E K L D F KDR V Q S K I G S L D N
 R R             R   K I E V       EK      A   V
                     *   * *
 I T H V P G G G N K K I E T H K L t f ren a k a k t d h g a e
 A H             V     D S Q   n H           r v
```

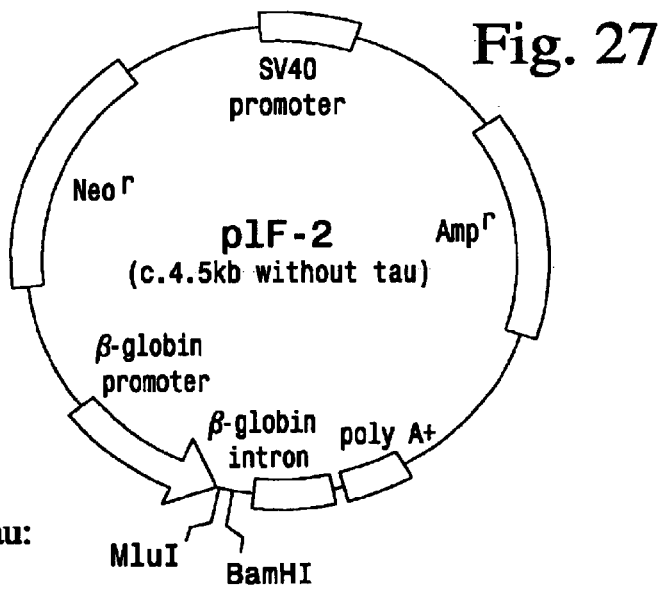

Fig. 27

PCR-Primers for dGAE tau:

```
        MluI
5' ... CGCGACGCGT ATG ATC AAA CAC GTC CCG GGA GGC ... 3'
                   M   T   K   H   V   P   G   G
(SEQ ID NO: 11)

BamHI
3' ... CGG CTT TGT CTG GTG CCC CGC CTC ACT CCTAGGGCGC ... 5'
        A   K   T   D   H   G   A   E   *
                              (SEQ ID NO: 12)
```

Fig. 29

dGAE Concentration in Lipofectin Mixture (µg/ml)

T40 Concentration in Lipofectin (µg/ml)

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
       (A) LENGTH: 109 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 1:

```
Asp Leu Lys Asn Val Lys Ser Lys Ile Gly Ser Thr Glu Asn Leu Lys
1               5                   10                  15

His Gln Pro Gly Gly Gly Lys Val Gln Ile Val Tyr Lys Pro Val Asp
            20                  25                  30

Leu Ser Lys Val Thr Ser Lys Cys Gly Ser Leu Gly Asn Ile His His
            35                  40                  45

Lys Pro Gly Gly Gly Gln Val Glu Val Lys Ser Glu Lys Leu Asp Phe
        50                  55                  60

Lys Asp Arg Val Gln Ser Lys Ile Gly Ser Leu Asp Asn Ile Thr His
65                  70                  75                  80

Val Pro Gly Gly Gly Asn Lys Lys Ile Glu Thr His Lys Leu Thr Phe
                85                  90                  95

Arg Glu Asn Ala Lys Ala Lys Thr Asp His Gly Ala Glu
                100                 105
```

(2) INFORMATION FOR SEQ ID NO: 2:

(i) SEQUENCE CHARACTERISTICS:
       (A) LENGTH: 108 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 2:

```
Asp Leu Lys Asn Val Lys Ser Lys Ile Gly Ser Thr Glu Asn Leu Lys
1               5                   10                  15

His Gln Pro Gly Gly Gly Lys Val Gln Ile Ile Asn Lys Lys Leu Asp
            20                  25                  30

Leu Ser Asn Val Gln Ser Lys Cys Gly Ser Lys Asp Asn Ile Lys His
            35                  40                  45

Val Pro Gly Gly Gly Ser Val Gln Ile Val Tyr Lys Pro Val Asp Leu
        50                  55                  60

Ser Lys Val Thr Ser Lys Cys Gly Ser Leu Gly Asn Ile His His Lys
65                  70                  75                  80

Pro Gly Gly Gly Gln Val Glu Val Lys Ser Glu Lys Leu Asp Phe Lys
                85                  90                  95

Asp Arg Val Gln Ser Lys Ile Gly Ser Leu Asp Asn
                100                 105
```

(2) INFORMATION FOR SEQ ID NO: 3:

(i) SEQUENCE CHARACTERISTICS:

(A) LENGTH: 109 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

```
Asp Leu Ser Asn Val Gln Ser Lys Cys Gly Ser Lys Asp Asn Ile Lys
1               5                   10                  15

His Val Pro Gly Gly Gly Ser Val Gln Ile Val Tyr Lys Pro Val Asp
            20                  25                  30

Leu Ser Lys Val Thr Ser Lys Cys Gly Ser Leu Gly Asn Ile His His
        35                  40                  45

Lys Pro Gly Gly Gly Gln Val Glu Val Lys Ser Glu Lys Leu Asp Phe
    50                  55                  60

Lys Asp Arg Val Gln Ser Lys Ile Gly Ser Leu Asp Asn Ile Thr His
65                  70                  75                  80

Val Pro Gly Gly Gly Asn Lys Lys Ile Glu Thr His Lys Leu Thr Phe
                85                  90                  95

Arg Glu Asn Ala Lys Ala Lys Thr Asp His Gly Ala Glu
            100                 105
```

(2) INFORMATION FOR SEQ ID NO: 4:

(i) SEQUENCE CHARACTERISTICS:
        (A) LENGTH: 1326 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..1326

(xi) SEQUENCE DESCRIPTION: SEQ ID NO: 4:

```
ATG GCT GAG CCC CGC CAG GAG TTC GAA GTG ATG GAA GAT CAC GCT GGG        48
Met Ala Glu Pro Arg Gln Glu Phe Glu Val Met Glu Asp His Ala Gly
1               5                   10                  15

ACG TAC GGG TTG GGG GAC AGG AAA GAT CAG GGG GGC TAC ACC ATG CAC        96
Thr Tyr Gly Leu Gly Asp Arg Lys Asp Gln Gly Gly Tyr Thr Met His
            20                  25                  30

CAA GAC CAA GAG GGT GAC ACG GAC GCT GGC CTG AAA GAA TCT CCC CTG       144
Gln Asp Gln Glu Gly Asp Thr Asp Ala Gly Leu Lys Glu Ser Pro Leu
        35                  40                  45

CAG ACC CCC ACT GAG GAC GGA TCT GAG GAA CCG GGC TCT GAA ACC TCT       192
Gln Thr Pro Thr Glu Asp Gly Ser Glu Glu Pro Gly Ser Glu Thr Ser
    50                  55                  60

GAT GCT AAG AGC ACT CCA ACA GCG GAA GAT GTG ACA GCA CCC TTA GTG       240
Asp Ala Lys Ser Thr Pro Thr Ala Glu Asp Val Thr Ala Pro Leu Val
65                  70                  75                  80

GAT GAG GGA GCT CCC GGC AAG CAG GCT GCC GCG CAG CCC CAC ACG GAG       288
Asp Glu Gly Ala Pro Gly Lys Gln Ala Ala Ala Gln Pro His Thr Glu
                85                  90                  95

ATC CCA GAA GGA ACC ACA GCT GAA GAA GCA GGC ATT GGA GAC ACC CCC       336
Ile Pro Glu Gly Thr Thr Ala Glu Glu Ala Gly Ile Gly Asp Thr Pro
            100                 105                 110

AGC CTG GAA GAC GAA GCT GCT GGT CAC GTG ACC CAA GCT CGC ATG GTC       384
Ser Leu Glu Asp Glu Ala Ala Gly His Val Thr Gln Ala Arg Met Val
        115                 120                 125
```

```
AGT AAA AGC AAA GAC GGG ACT GGA AGC GAT GAC AAA AAA GCC AAG GGG        432
Ser Lys Ser Lys Asp Gly Thr Gly Ser Asp Asp Lys Lys Ala Lys Gly
    130                 135                 140

GCT GAT GGT AAA ACG AAG ATC GCC ACA CCG CGG GGA GCA GCC CCT CCA        480
Ala Asp Gly Lys Thr Lys Ile Ala Thr Pro Arg Gly Ala Ala Pro Pro
145                 150                 155                 160

GGC CAG AAG GGC CAG GCC AAC GCC ACC AGG ATT CCA GCA AAA ACC CCG        528
Gly Gln Lys Gly Gln Ala Asn Ala Thr Arg Ile Pro Ala Lys Thr Pro
                165                 170                 175

CCC GCT CCA AAG ACA CCA CCC AGC TCT GGT GAA CCT CCA AAA TCA GGG        576
Pro Ala Pro Lys Thr Pro Pro Ser Ser Gly Glu Pro Pro Lys Ser Gly
        180                 185                 190

GAT CGC AGC GGC TAC AGC AGC CCC GGC TCC CCA GGC ACT CCC GGC AGC        624
Asp Arg Ser Gly Tyr Ser Ser Pro Gly Ser Pro Gly Thr Pro Gly Ser
            195                 200                 205

CGC TCC CGC ACC CCG TCC CTT CCA ACC CCA CCC ACC CGG GAG CCC AAG        672
Arg Ser Arg Thr Pro Ser Leu Pro Thr Pro Pro Thr Arg Glu Pro Lys
    210                 215                 220

AAG GTG GCA GTG GTC CGT ACT CCA CCC AAG TCG CTG TCT TCC GCC AAG        720
Lys Val Ala Val Val Arg Thr Pro Pro Lys Ser Leu Ser Ser Ala Lys
225                 230                 235                 240

AGC CGC CTG CAG ACA GCC CCC GTG CCC ATG CCA GAC CTG AAG AAT GGC        768
Ser Arg Leu Gln Thr Ala Pro Val Pro Met Pro Asp Leu Lys Asn Gly
                245                 250                 255

AAG TCC AAG ATC GGC TCC ACT GAG AAC CTG AAG CAC CAG CCG GGA GGC        816
Lys Ser Lys Ile Gly Ser Thr Glu Asn Leu Lys His Gln Pro Gly Gly
        260                 265                 270

GGG AAG GTG CAG ATA ATT AAT AAG AAG CTG GAT CTT AGC AAC GTC CAG        864
Gly Lys Val Gln Ile Ile Asn Lys Lys Leu Asp Leu Ser Asn Val Gln
            275                 280                 285

TCC AAG TGT GGC TCA AAG GAT AAT ATC AAA CAG GTC CCG GGA GGC GGC        912
Ser Lys Cys Gly Ser Lys Asp Asn Ile Lys Gln Val Pro Gly Gly Gly
    290                 295                 300

AGT GTG CAA ATA GTC TAC AAA CCA GTT GAC CTG AGC AAG GTG ACC TCC        960
Ser Val Gln Ile Val Tyr Lys Pro Val Asp Leu Ser Lys Val Thr Ser
305                 310                 315                 320

AAG TGT GGC TCA TTA GGC AAC ATC CAT CAT AAA CCA GGA GGT GGC CAG       1008
Lys Cys Gly Ser Leu Gly Asn Ile His His Lys Pro Gly Gly Gly Gln
                325                 330                 335

GTG GAA GTA AAA TCT GAG AAG CTT GAC TTC AAG GAC AGA GTC CAG TCG       1056
Val Glu Val Lys Ser Glu Lys Leu Asp Phe Lys Asp Arg Val Gln Ser
        340                 345                 350

AAG ATT GGG TCC CTG GAC AAT ATC ACC CAC GTC CCT GGC GGA GGA AAT       1104
Lys Ile Gly Ser Leu Asp Asn Ile Thr His Val Pro Gly Gly Gly Asn
            355                 360                 365

AAA AAG ATT GAA ACC CAC AAG CTG ACC GTC CGC GAG AAC GCC AAA GCC       1152
Lys Lys Ile Glu Thr His Lys Leu Thr Val Arg Glu Asn Ala Lys Ala
    370                 375                 380

AAG ACA GAC CAC GGG GCG GAG ATC GTG TAC AAG TCG CCA GTG GTG TCT       1200
Lys Thr Asp His Gly Ala Glu Ile Val Tyr Lys Ser Pro Val Val Ser
385                 390                 395                 400

GGG GAC ACG TCT CCA CGG CAT CTC AGC AAT GTC TCC TCC ACC GGC AGC       1248
Gly Asp Thr Ser Pro Arg His Leu Ser Asn Val Ser Ser Thr Gly Ser
                405                 410                 415

ATT GAC ATG GTA GAC TCG CCC CAG CTC GCC ACG CTA GCT GAC GAG GGG       1296
Ile Asp Met Val Asp Ser Pro Gln Leu Ala Thr Leu Ala Asp Glu Gly
        420                 425                 430

TCT GCC TCC CTG GCC AAG CAG GGT TTG TGA                               1326
Ser Ala Ser Leu Ala Lys Gln Gly Leu  *
            435                 440
```

(2) INFORMATION FOR SEQ ID NO: 5:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Leu Ser Ser Ala Lys
225                 230                 235                 240

Ser Arg Leu Gln Thr Ala Pro Val Pro Met Pro Asp Leu Lys Asn Gly
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys Gln Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350
```

```
Lys Ile Gly Ser Leu Asp Asn Ile Thr His Val Pro Gly Gly Gly Asn
            355                 360                 365

Lys Lys Ile Glu Thr His Lys Leu Thr Val Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Gly
                420                 425                 430

Ser Ala Ser Leu Ala Lys Gln Gly Leu
        435                 440
```

(2) INFORMATION FOR SEQ ID NO: 6:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: <Unknown>

(xi) SEQUENCE DESCRIPTION: SEQ ID NO: 6:

```
ATCAAACACG TCCCGGGAGG CGGCAGTGTG CAAATAGTCT ACAAACCAGT TGACCTGAGC      60

AAGGTGACCT CCAAGTGTGG CTCATTAGGC AACATCCATA AACCAGGAGG TGGCCAGGTG     120

GAAGTAAAAT CTGAGAAGCT TGACTTCAAG GACAGAGTCC AGTCGAAGAT TGGGTCCCTG     180

GACAATATCA CCCACGTCCC TGGCGGAGGA AATAAAAAGA TTGAAACCCA CAAGCTGACC     240

TTCCGCGAGA ACGCCAAAGC CAAGACAGAC CACGGGGCGG AGTGAGAATT C              291
```

(2) INFORMATION FOR SEQ ID NO: 7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
GCCCGGGCCC CATAGATCAA ACACGTCCCG GGAGGCGGCA GTGTGCAA                    48
```

(2) INFORMATION FOR SEQ ID NO: 8:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
AGATTACAGA ATTCTCACTC CGCCCCGTGG TCTGTCTTGG CTTTGGC                     47
```

(2) INFORMATION FOR SEQ ID NO: 9:

(i) SEQUENCE CHARACTERISTICS:
        (A) LENGTH: 140 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Asp Leu Lys Asn Val Lys Ser Lys Ile Gly Ser Thr Glu Asn Leu Lys
1               5                   10                  15

His Gln Pro Gly Gly Gly Lys Val Gln Ile Ile Asn Lys Lys Leu Asp
            20                  25                  30

Leu Ser Asn Val Gln Ser Lys Cys Gly Ser Lys Asp Asn Ile Lys His
        35                  40                  45

Val Pro Gly Gly Gly Ser Val Gln Ile Val Tyr Lys Pro Val Asp Leu
    50                  55                  60

Ser Lys Val Thr Ser Lys Cys Gly Ser Leu Gly Asn Ile His His Lys
65              70                  75                      80

Pro Gly Gly Gly Gln Val Glu Val Lys Ser Glu Lys Leu Asp Phe Lys
            85                  90                  95

Asp Arg Val Gln Ser Lys Ile Gly Ser Leu Asp Asn Ile Thr His Val
            100                 105                 110

Pro Gly Gly Gly Asn Lys Lys Ile Glu Thr His Lys Leu Thr Phe Arg
            115                 120                 125

Glu Asn Ala Lys Ala Lys Thr Asp His Gly Ala Glu
    130                 135                 140

(2) INFORMATION FOR SEQ ID NO: 10:

(i) SEQUENCE CHARACTERISTICS:
        (A) LENGTH: 140 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

Asp Leu Lys Asn Val Lys Ser Lys Ile Gly Ser Thr Asp Asn Ile Lys
1               5                   10                  15

Tyr Gln Pro Lys Gly Gly Gln Val Arg Ile Leu Asn Lys Lys Ile Asp
            20                  25                  30

Phe Ser Lys Val Gln Ser Arg Cys Gly Ser Lys Asp Asn Ile Lys His
        35                  40                  45

Ser Ala Gly Gly Gly Asn Val Gln Ile Val Thr Lys Lys Ile Asp Leu
    50                  55                  60

Ser His Val Thr Ser Lys Cys Gly Ser Leu Lys Asn Ile Arg His Arg
65              70                  75                      80

Pro Gly Gly Gly Arg Val Lys Ile Glu Ser Val Lys Leu Asp Phe Lys
            85                  90                  95

Glu Lys Val Gln Ala Lys Val Gly Ser Leu Asp Asn Ala His His Val
            100                 105                 110

Pro Gly Gly Gly Asn Val Lys Ile Asp Ser Gln Lys Leu Asn Phe Arg
            115                 120                 125

Glu His Ala Lys Ala Arg Val Asp His Gly Ala Glu
    130                 135                 140

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single

```
        (D) TOPOLOGY: linear (ii) MOLECULE TYPE: cDNA (xi) SEQUENCE DESCRIPTION: SEQ ID NO: 11:

CGCGACGCGT ATGATCAAAC ACGTCCCGGG AGGC                                      34

(2) INFORMATION FOR SEQ ID NO: 12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CGGCTTTGTC TGGTGCCCCG CCTCACTCCT AGGGCGC                                   37
```

INHIBITION OF TAU-TAU ASSOCIATION

The present invention relates to novel methods for the detection of substances capable of modulating or inhibiting pathological tau-tau protein association and pathological neurofilament aggregation. The methods of the present invention are particularly useful in screening substances for the prophylaxis and treatment of Alzheimer's disease.

Alzheimer's disease (AD) is the most common single cause of dementia in late life (Livingstone (1994) The scale of the problem. In: Dementia (eds. Burns and Levy) Chapman & Hall, London, pp. 21–35). Individuals with Alzheimer's disease are characterised by progressive dementia that presents with increasing loss of memory, disturbances in judgement, perception and speech, and global intellectual deterioration (Roth and Iversen (1986) Brit. Med. Bull., 42 (special volume)).

The major pathological hallmarks of Alzheimer's disease are senile plaques and neurofibrillary tangles, both of which contain paired helical filaments (PHFs) of which the microtubule-associated protein tau is a constituent (Wischik et al. (1988) Proc. Natl. Acad. Sci. USA, 85, 4506–4510). Plaques also contain β-amyloid fibrils derived from an as yet undefined abnormality in the processing of the amyloid precursor protein (APP; Kang et al. (1987) Nature, 325, 733–736).

Studies of Alzheimer's disease have pointed to loss of the normal microtubule associated protein tau (Mukaetova-Ladinska et al. (1993) Am. J. Pathol., 143, 565–578; Wischik et al. (1995a) Neurobiol. Ageing, 16: 409–417; Lai et al. (1995b) Neurobiol. Ageing, 16: 433–445), accumulation of pathological paired helical filaments (PHFs; Mukaetova-Ladinska et al. (1993), loc. cit.; Harrington et al. (1994a) Dementia, 5, 215–228; Harrington et al. (1994b) Am. J. Pathol., 145, 1472–1484; Wischik et al., (1995a), loc. cit.) and loss of synapses in mid-frontal cortex (Terry et al. (1991) Ann. Neurol., 30, 572–580) as strong discriminatory markers for cognitive impairment. Loss of synapses (Terry et al., loc. cit.) and loss of pyramidal cells (Bondareff et al. (1993) Arch. Gen. Psychiatry, 50, 350–356) are both correlated with morphometric measures of tau-reactive neurofibrillary pathology, and this correlates at the molecular level with an almost complete redistribution of the tau protein pool from soluble to polymerised form (PHFs) in Alzheimer's disease (Mukaetova-Ladinska et al. (1993), loc. cit.; Lai et al. (1995), loc. cit.). A possible explanation for these changes is that the pathological redistribution of tau protein into PHFs causes a failure of axonal transport in cortico-cortical association circuits through failure to maintain axonal tubulin in the polymerised state within pyramidal cells (Wischik et al. (1995a), loc. cit.; Wischik et al. (1995b) Neurobiol. Ageing, in press; Wischik et al (1995c) Structure, biochemistry and molecular pathogenesis of paired helical filaments in Alzheimer's disease. Eds. A. Goate and F. Ashall, in press; Lai et al., (1995), loc. cit.). A resulting failure of transport of synaptic constituents from projection soma to distant association neocortex would lead to synaptic loss and cognitive impairment. Further factors include the direct toxicity of PHF accumulation in pyramidal cells (Bondareff et al., (1993), Arch. Gen. Psychiat. 50: 350–356; (1994), J. Neuropath. Exp. Neurol. 53: 158–164), and the possible direct toxicity of truncated tau accumulation impairing cellular function (Mena et al. (1991), J. Neuropath. Exp. Neurol. 50: 474–490).

Although studies of molecular pathogenesis in model systems have emphasised the neurotoxic role of β-amyloid accumulation (reviewed in Harrington and Wischik (1994) Molecular Pathobiology of Alzheimer's disease. In: Dementia (eds. A. Burns and R. Levy). Chapman & Hall London, pp. 211–238), the evidence linking β-amyloid deposition directly with cognitive impairment in humans is weak. It is more likely that altered processing of APP is only one of several possible factors which might initiate altered processing of tau protein. Other initiating factors include unknown processes associated with apoE4 (Harrington et al. (1994b), loc. cit.), trisomy of chromosome 21 (Mukaetova-Ladinska et al. (1994) Dev. Brain Dysfunct. 7: 311–329), and environmental factors, such as prolonged exposure to sub-toxic levels of aluminium (Harrington et al. (1994c) Lancet, 343, 993–997). Distinct etiological factors are able to initiate a common pattern of disturbance in tau protein processing which includes: C-terminal truncation at Glu-391, formation of PHF tau polymers, loss of soluble tau, and accumulation of abnormally phosphorylated tau species (Wischik et al. (1996) Int. Rev. Psychiat., in press).

The fragment of the microtubule-associated protein tau which has been shown to be an integral constituent of the protease-resistant core structure of the PHF is a 93/95 amino acid residue fragment derived from the microtubule binding domain of tau (Wischik et al. (1988), loc. cit.; Kondo et al. (1988) Neuron, 1, 827–834; Jakes et al. (1991) EMBO J., 10, 2725–2729; Novak et al. (1993) EMBO J., 12, 365–370). Tau protein exists in 6 isoforms of 352–441 amino acid residues in the adult brain (Goedert et al. (1989) Neuron, 3, 519–526). In general structure the tau molecule consists of an extensive N-terminal domain of 252 residues, which projects from the microtubule, a tandem repeat region of 93–125 residues consisting of 3 or 4 tandem repeats and which is the microtubule binding domain, and a C-terminal tail of 64 residues. Each tandem repeat is composed of a 19 residue tubulin binding segment, and 12 residue linker segment (Butner and Kirschner (1991) J. Cell Biol., 115, 717–730; FIG. 1). The major tau constituent which can be extracted from enriched protease-resistant core PHF preparations is a 12 kDa fragment derived from both 3- and 4-repeat isoforms, but restricted to the equivalent of 3 tandem repeats regardless of isoform (Jakes et al., loc. cit.; FIG. 2). The N- and C-terminal boundaries of the fragment define the precise extent of the characteristic protease-resistant core PHF tau unit. It is phase—shifted by 14/16 residues with respect to the binder/linker organisation of the normal molecule defined by Butner and Kirschner, bc. cit., FIG. 1) and is C-terminally truncated at Glu-391, or at a homologous position in the third repeat of the 4-repeat isoform (Novak et al. (1993), loc. cit.; FIGS. 3A, 3B and 3C). A monoclonal antibody (mAb 423) is available which specifically recognises this C-terminal truncation point, and histological studies using this antibody have shown the presence of tau protein C-terminally truncated at Glu-391 at all stages of neurofibrillary degeneration (Mena et al. (1995) Acta Neuropathol., 89, 50–56; Mena et at. (1996) Acia Neuropathol. (in press)). Thus, a possible post-translation modification implicated in PHF assembly is abnormal proteolysis.

Methods have been developed which permit discrimination between several tau pools found in AD brain tissues: normal soluble tau, phosphorylated tau, and protease-resistant PHFs (Harrington et al. (1990), (1991), (1994a), loc. cit.). These methods have been deployed in studies of severe AD and Down's Syndrome (Mukaetova-Ladinska et al. (1993; 1995), loc. cit.), in prospectively assessed cases at early stage AD (Wischik et al. (1995a), loc. cit.; Lai et al. (1995), loc. cit.) and cases with other neuropathological diagnoses including senile dementia of the Lewy body type and Parkinson's disease (Harrington et al. (1994a), (1994b), loc. cit.). The overall PHF content in brain tissue distinguishes unambiguously between patients with and without dementia of the Alzheimer type. There is overall a 19-fold difference in PHF content, and in temporal cortex the difference reaches 40-fold. Furthermore, apolipoprotein E genotyping of the cortical Lewy body cases showed that the frequency of the E4 allele was raised to a similar extent to that seen in AD. Therefore, the presence of the E4 allele cannot be the sole cause of the characteristic tau pathology of AD, since this was not seen in the Lewy body cases (Harrington et al. (1994b), loc. cit.).

A further parameter which distinguishes cases with and without AD is the amount of normal soluble tau protein. Although tau levels are higher in white matter than in grey matter, as expected for an axonal microtubule associated protein, the amount found in grey matter also reflects afferent axonal innervation. In AD, there is a substantial loss of normal soluble tau protein which affects all brain regions uniformly (Mukaetova-Ladinska et al. (1993), loc. cit.). The molecular basis of this uniform decline is not known, and cannot be explained by reduced tau mRNA (Goedert et al. (1988) Proc. Natl. Acad. Sci. USA, 85, 4051–4055). The net effect the two processes of accumulation of PHFs and loss of soluble tau is an anatomical redistribution of the tau protein pool, from white matter predominant to grey matter predominant, and from frontal predominant to temporo-parietal prodominant.

The global extent of tau protein redistribution in AD can be appreciated from the data shown in FIG. 4, where total free and PHF-bound tau pools are compared. Whereas in controls, 97% of the tau protein pool is in the soluble phase, in AD 83% of the tau protein pool is to be found in the insoluble phase, almost entirely in a form truncated and polymerised into PHFs (Mukaetova-Ladinska et al. (1993), loc. cit.). A study of early stage AD in cases prospectively assessed by the clinical diagnostic instrument CAMDEX (Roth et al. (1986) Brit. J. Psych., 149, 698–709) and graded post-mortem by the staging criteria of Braak and Braak (1991), Acta Neuropathol. 82, 239–259) demonstrated that the loss of soluble tau is directly related to the tangle count and to the extent of PHF accumulation (Lai et al. (1995), loc. cit.).

Although abnormally phosphorylated tau has been considered a possible PHF precursor (Lee et. al. (1991) Science, 251, 675–678; Goedert et al. (1994), in Microtubules (Hyams and Lloyd, eds.) pp. 183–200. John Wiley & Sons, NY), normal tau has been found to be phosphorylated at many of the sites previously considered abnormally phosphorylated in PHF-associated tau protein (Matsuo et al. (1994) Neuron, 13, 989–1002). In the study of early stage AD, insoluble hyperphosphorylated tau species were first seen after appreciable tau redistribution into PHFs had occurred (Lai et al., 1995; FIG. 5). There was no evidence of selective accumulation of phosphorylated species prior to the appearance either of PHFs, or of neurofibrillary tangles (Lai et al. (1995), loc. cit.). Likewise, there was no evidence that phosphorylated tau feeds into the total PHF-bound pool during progression of pathology (Lai et al. (1995), loc. cit.). Phosphorylation of tau protein, insofar as it is abnormal, appears to be a secondary process affecting about 5% of PHFs at any stage of pathology (Wischik et al. (1995a), (1995c), loc. cit.).

Studies of early stage Alzheimer's disease also showed that the rate of transfer of soluble tau into PHFs is Geometric with respect to the PHF level, with a progressive increase in the rate of incorporation at higher ambient levels of PHFs (Lai et al.(1995). loc. cit.; FIG. 6B). Furthermore, the observed rate of loss of soluble tau with progression of pathology is not enough to account entirely for the observed rate of accumulation of PHFs. Progressively more new tau synthesis is induced as the ambient level of soluble tau falls below 580 pmol/g, and this too feeds into PHF assembly (FIG. 6A). The rate of PHF assembly is therefore not determined by the state or concentration of the soluble precursor, which appears to be entirely normal even in AD (Wischik et al. (1995a), (1995b), loc. cit.). Rather, the rate of transfer of soluble tau into PHFs is determined by the ambient level of PHF-tau, suggesting that the critical post-translational modification responsible for PHF assembly occurs at the point of incorporation of tau into the PHF.

A likely explanation for these findings is that tau protein undergoes an induced conformational change at the point of incorporation into the PHF, which is associated with the half-repeat phase shift in the tandem repeat region that has been documented previously (Novak et al. (1993), loc. cit.). This conformational chance could expose a high affinity tau capture site which permits the capture and induced conformational modification of a further tau molecule, and so on. The critical conformational change in tau protein which determines the rate of PHF assembly would not then need to be a chemical modification of soluble tau, but an induced conformational change which is produced by the binding of tau protein to a pathological substrate. The process could be initiated by non-tau proteins, such as a product of APP metabolism (Caputo et al. (1992) Brain Res., 597, 227–232), a modified mitochondrial protein (Wallace (1994) Proc. Natl. Acad. Sci. USA, 91, 8739–8746), etc. Once tau capture had been initiated, the process could continue provided the rate of further tau capture exceeded the rate of degradation of the pathological tau complex. Degradation could be limited by the fact that the core tau complex of the PHF is resistant to proteases (Wischik et al. (1988), loc. cit.; Jakes et al., loc. cit.). Such a process, an "amyloidosis of tau protein", could be initiated and progress geometrically without any intervening chemical modification of soluble tau protein, as commonly supposed.

FIG. 7 schematically depicts the transformation of tau protein into PHFs in Alzheimer's disease. The major protein constituent of the PHF core is a form of tau protein which is truncated down to a 93 residue fragment which encompasses a phase-shifted version of the tandem repeat region of the tau molecule which normally functions as the microtubule binding domain. The assembly of the PHF can be envisaged as occurring as a result of a repetitive sequence of events in which pathological tau-tau binding plays a pivotal role. This binding of free tau is favoured at a physiological concentration only in the asymmetrical case in which one tau molecule has already undergone pathological capture (e.g. to a product of APP metabolism (Caputo et al. (1992) Neurobiol. Ageing, 13, 267–274), or an altered mitochondrial protein (Jancsit et al. (1989) Cell Motil. Cytoskel., 14, 372–381; Wallace, loc. cit.), and further tau binding is enhanced by partial proteolytic processing of the captured species leaving only the truncated tau unit. Once a full length or truncated unit binds a full-length molecule, partial proteolytic processing of the pathological complex results in the production of a dimer of core tau units, with loss of N- and C-terminal domains of the previously intact molecule (s). The limits of proteolytic processing are determined by the region of tau-tau association, which corresponds precisely to the minimal protease-resistant tau unit we have described (Novak et al. (1993), loc. cit.); see FIGS. 17A, 17B and 17C). However, the end result of this partial proteolysis is to reproduce the core tau unit, which is able to capture a further full-length tau molecule. This process can be repeated indefinitely. It requires two key steps to continue to the point of exhaustion of the available tau protein pool. The first is repeated capture of full-length tau by the truncated unit, the second is truncation of bound full-length tau to reproduce the core unit.

So far, no reliable methods for the measurement of pathological tau-tau association are available and no substances capable of modulating or inhibiting pathological tau-tau association have been described.

The solution to the above technical problem is achieved by providing the embodiments characterised in the claims.

Accordingly, the present invention relates to methods for the detection of agents capable of modulating or inhibiting pathological tau-tau association comprising contacting a) a tau protein or a derivative thereof containing the tau core fragment with b) an agent suspected of being capable of modulating or inhibiting tau-tau association and with c) a labelled tau protein or a labelled derivative thereof capable of binding to the tau protein of step a) or with a tau protein or a derivative thereof which is distinct from the tau protein of step a) and also capable of binding to the tau protein of step a) and d) detection of the tau-tau binding.

The modification of tau which is responsible for its polymerisation into PHFs is propagated by a physical conformational change rather than any preceding Chemical post-translational modification of tau. Surprisingly, it is possible to transfer this modification which is induced in vivo at the point of pathological tau capture to the in vitro method according to the above process by initial tau binding to a solid phase. Tau isolated from the brain of the rat neonate was entirely unable to bind to the core tau unit of the PHF (FIG. 14; POTr). But neonatal tau which had been previously bound passively to solid phase matrix, was induced to bind unmodified full-length tau protein with an identical high affinity to that demonstrated with the core tau unit (FIGS. 15 & 16). Thus, the critical factor required to convert a species of tau incapable of pathological binding, into a species able to capture a further tau molecule with high affinity is the conformational change induced by passive binding of neonatal tau to the solid phase substrate. This demonstrated that the exposure of the high affinity tau capture site could be induced physically by the conformational change that occurs upon binding of tau to a suitable substrate, and does not require any other chemical modification.

BRIEF DESCRIPTION OF THE DRAWINGS

FIG. 3A-C shows the N-terminal sequence analysis of distinct peptides released from core PHF preparations.

FIG. 11 shows the determination of Kd for binding of full-length tau ("T40") to the truncated core tau unit terminating at Ala-390 ("a"), using mAb 499 to measure bound full-length human tau. The horizontal axis on the under graph shows the concentration of T40 used and the vertical axis shows mAb 499 immunoreactivity. Each binding curve is obtained at a plating concentration of "a" which is shown.

FIG. 13 shows a similar experiment to that shown in FIG. 12, keeping the sodium chloride concentration constant at 137 mM, but varying the pH in the range 3–10, with binding in physiological phosphate-buffered normal saline ("PBS", pH 7.4) and water ("0") shown for comparison.

FIG. 17A shows full-length tau bound to dGA and incubated with Pronase. FIG. 17B shows full length tau which had self-aggregated in the solid phase in the absence of dGA was digested similarly. FIG. 17C shows the immunoreactivity of the digested fragments, FIG. 18A and 18B show accumulation of truncated tau by repetitive tau capture, beginning with the truncated tau fragment (dGA) in the solid phase, adding full-length recombinant human tau, and digesting with Pronase, and repeating the addition and digestion. FIG. 18A shows pronase digestion of the complex was associated with incremental accumulation of tau protein truncated at Glu-391 in the solid phase following each digestion cycle. FIG. 18B shows binding of full-length tau was detected by the appearance of immunoreactivity for the N terminus of tau which was entirely abolished by Pronase digestion.

FIGS. 19A and 19B shows relative tau-tau binding (vertical axis) in the presence of increasing concentrations of prototype inhibitory phenothiazines (horizontal axis).

FIGS. 21A and 21B show nucleotide and predicted amino acid sequences of a human tau protein isoform (SEQ ID NO: 4).

FIG. 22 shows amino acid and cDNA sequence of PHF-core tau unit (SEQ ID NO: 6) and the orimers (SEQ ID NO: 7 and 8) used in construction of the preferred core tau unit.

FIGS. 24A–24D show chemical structures of the compounds tested with values for standardised binding according to FIG. 17.

FIG. 26 shows sequence differences in the tandem repeat region of human tau (upper line: SEQ ID NO: 9) and human MAP2 (lower line: SEQ ID NO: 10). Vertical arrows show the limits of the truncated PHF-core fragment terminating at Glu-39 1, and the tubulin-binding segments are shown underlined.

FIG. 27 shows the plF2 expression vector which is an SV40-based eukaryotic expression vector. Also shown are primers SEQ ID NO: 11 and 12.

FIG. 29 shows mouse fibroblast 3T3 cells transfected with PIF: :dGAE, expressing the truncated PHF-core tau fragment terminating at Glu-39 1, immunolabelled with mAb 7.51.

Figure 17:
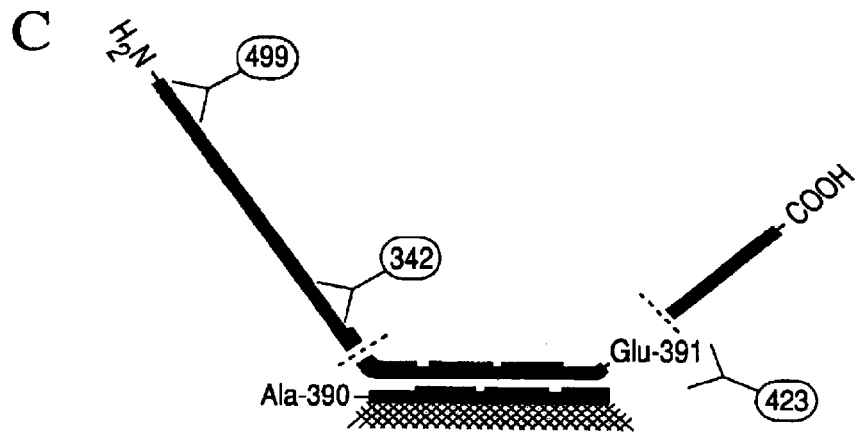
FIGS. 17A, 17B and 17C show proteolytic digestion of aggregated full-length tau protein as measured by immunoreactivity with various stated mAb's.

According to the invention, the pathological binding which is reproduced in vitro had certain critical properties identical to those seen in the human brain. This is in particular that full-length tau protein (FIG. 21, SEQ ID NO:4) bound to a core tau unit terminating at Ala-390 (FIGS. 3A and 3C ), and therefore lacking the Glu-391 needed for recognition by monoclonal antibody 423, could be made to react with mAb 423 after treatment of the bound tau complex with the broad spectrum protease, Pronase, in a manner that depended quantitatively in the extent of Pronase digestion (FIGS. 17A, 17B and 17C). Digestion-dependent loss of N-terminal tau immunoreactivity could be demonstrated to occur in parallel with the acquisition of the mAb 423 immunoreactivity characteristic of the core PHF (FIGS. 17A, 17B and 17C). Thus, the essential requirement needed for the creation of the tau unit isolated from the core of the PHF, and produced in the brain in Alzheimer's disease is the pathological tau-tau interaction which had been reproduced in vitro.

Further, repetitive cycles of binding of full-length tau to the core tau unit terminating at Ala-390, followed by treatment with Pronase, then binding of full-length tau and further Pronase digestion, and so on up to four cycles, was associated with progressive accumulation of tau C-terminally truncated at Glu-391 (FIG. 18A), and with progressively enhanced capacity to bind more full-length tau after each cycle (FIG. 18B). This demonstrated that the essential role of proteolysis in the model depicted in FIG. 7 is to prevent saturation, and hence facilitates the unlimited progressive transformation of soluble tau into the truncated tau units of the core PHF.

Figure 7:
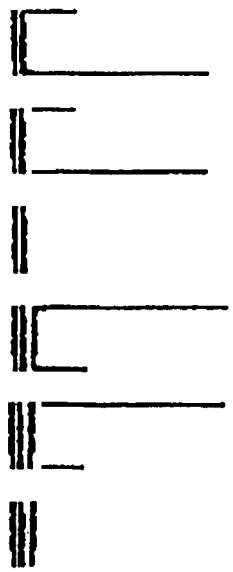
FIG. 7 shows a hypothetical scenario for transformation of tau protein into PHFs in Alzheimer's disease showing autocatalytic cycles of immobilisation, truncation, captured, partial proteolytic degradation and further capture.

Having shown that all the steps depicted in FIG. 7 could be reproduced in vitro, and that the critical requirement for progression of the process was the high affinity tau capture step it is possible to demonstrate the use of the binding assay to find compounds able to block the high affinity tau-tau interaction. Competitive inhibition of 20% could be demonstrated when the most potent inhibitory compounds were present at 1:1 molar ratio with respect to tau, and further inhibition was found to be approximately linear in the range up to 10:1 molar ratio (FIG. 19).

Since the tandem repeat region functions as a whole, it is unexpected that it would be possible to demonstrate selective competitive inhibition of pathological tau-tau binding without interference to the normal binding of tau to tubulin via the same region of the molecule. A method of determining any possible interference, i. e. binding of tau or a derivative thereof to tubulin molecules, comprises contacting a depolymerised tubulin preparation, or preparation of taxol-stabilised microtubules with an agent suspected of being capable of modulating or inhibiting pathological tau-tau association and a tau compound mentioned in above step c) followed by detection of the tau-tubulin binding.

Figure 2:
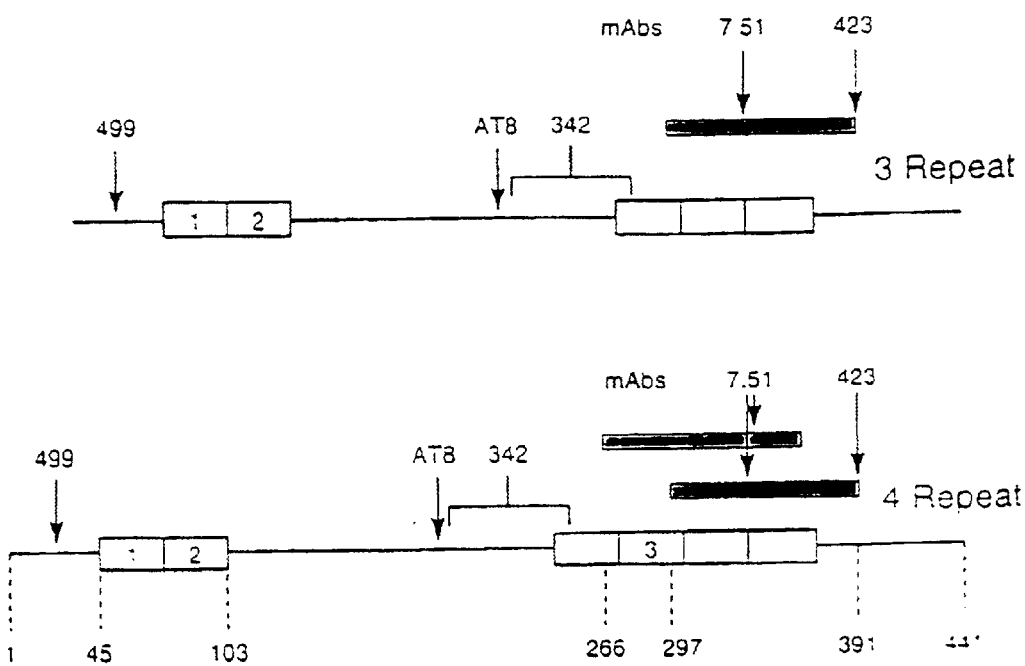
FIG. 2 shows a schematic representation of tau protein isoforms, whereon tau fragments and the positions of epitopes for mAb are shown.

The term "tau protein" refers to any protein of the tau protein family mentioned above and derivatives thereof. Tau proteins are characterised as one family among a larger number of protein families which co-purify with microtubules during repeated cycles of assembly and disassembly (Shelanski et al. (1973) Proc. Natl. Acad. Sci. USA, 70, 765–768), and known as microtubule-associated-proteins (MAPs). The tau family in addition is characterised by the presence of a characteristic N-terminal segment which is shared by all members of the family, sequences of ~50 amino acids inserted in the N-terminal segment, which are developmentally regulated in the brain, a characteristic tandem repeat region consisting of 3 or 4 tandem repeats of 31–32 amino acids, and a C-terminal tail (FIG. 2).

In a preferred embodiment of the present invention the tau protein comprises the amino acid sequence of FIG. 21 (SEQ ID NO: 5), referred to as "T40" (Goedert et al. (1989), Neuron 3: 519–526), or fragments thereof and comprising the form of the tau protein having 2 N-terminal inserts and 4 tandem repeats.

The term "tau core fragment" is defined in its most basic form as tau fragment comprising a truncated tau protein sequence derived from the tandem repeat region which in the appropriate conditions is capable of binding to the tandem repeat region of a further tau protein with high affinity. Ordinarily, preferred tau proteins, tau protein derivatives and tau protein core fragments have an amino acid sequence having at least 70% amino acid sequence identity with the corresponding human tau protein amino acid sequence (FIG. 21, SEQ ID NO: 5), preferably at least 80% and most preferably at least 90% and are characterised in that they are capable to bind to the human tau core fragment. A particularly advantageous embodiment of the assay method comprises the tau core fragment with the amino acid sequence shown in FIG. 22 (SEQ ID NO: 6; Novak et al., 1993). This recombinant tau peptide expressed by E. coli in vitro corresponds to species isolated from protease-resistant core-PHF preparations (Wischik et al. (1988), loc. cit.; Jakes et al. (1991), loc. cit.). The term "tau core fragment" also includes derivatives thereof as described below and mentioned in FIG. 25 and 26 (SEQ ID NO: 9 and 10).

Figure 25:
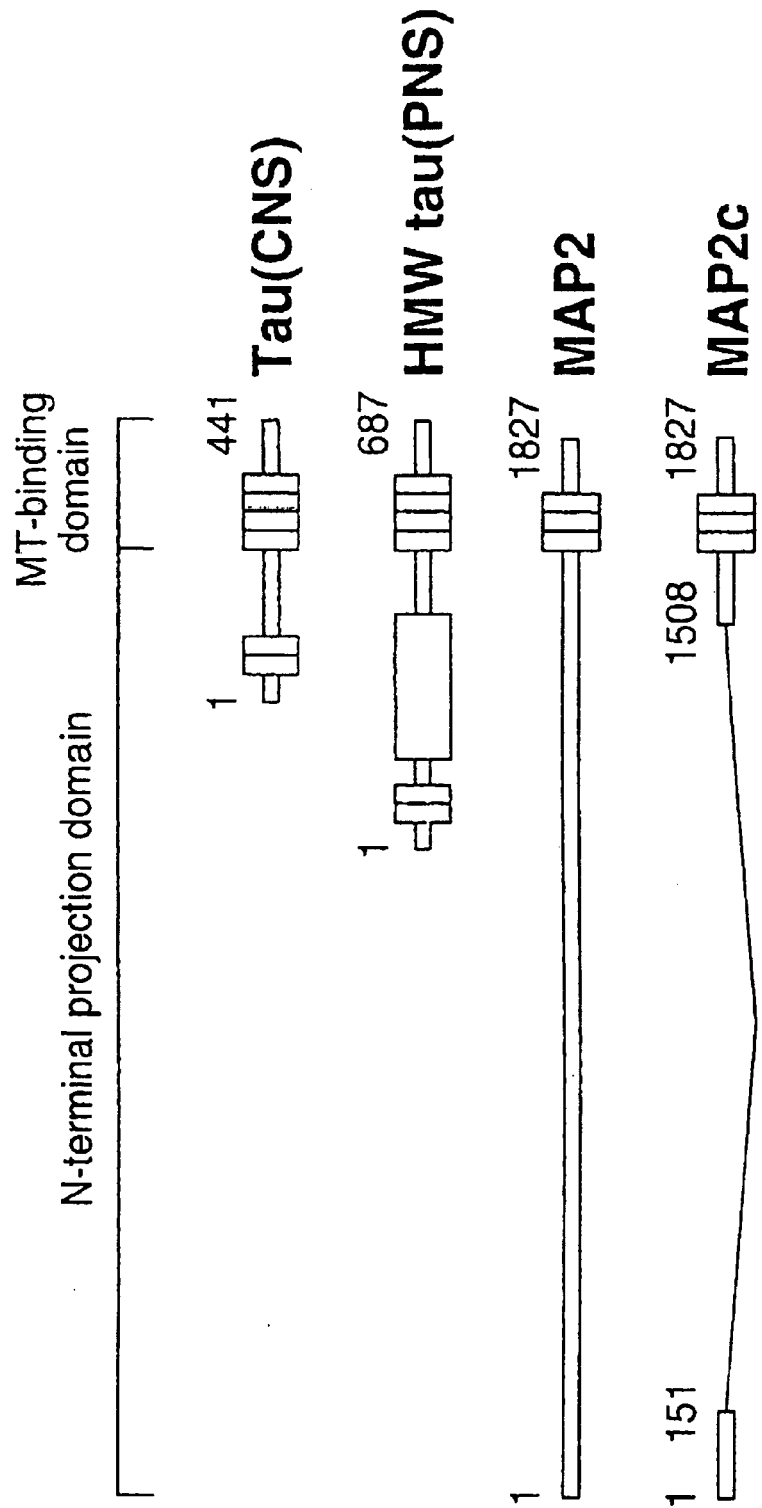
FIG. 25 shows a schematic representation of tau, MAP2 (adult form), MAP2C (juvenile form) and high molecular weight tau.

The terms "tau protein derivative" and "tau core fragment derivative" comprise fragments of naturally or non-naturally occurring tau proteins and related proteins comprising at least partial amino acid sequences resembling to the tandem repeat region of the tau proteins, i. e. proteins in which one or more of the amino acids of the natural tau or its fragments have been replaced or deleted without loss of binding activity. Examples of naturally occurring proteins with sequence similarity in the tandem repeat region are microtubule-associated proteins (MAP2; FIGS. 25 and 26: SEQ ID NO: 9 and 10; Kindler and Garner (1994) Mol. Brain Res. 26, 218–224). Such analogues may be produced by known methods of peptide chemistry or by recombinant DNA technology.

The terms "tau protein derivative" and "tau core fragment derivative" comprise derivatives which may be prepared from the functional groups occurring as side chains on the residues or the N- or C-terminal groups, by means known in the art. These derivatives may include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl- or threonyl residues) formed with acyl moieties.

The core PHF tau fragment may be isolated from AD brain tissues by the method described in Wischik et al. (1988); (1995a), loc. cit.). The method depends on a series of differential centrifugation steps conducted in empirically determined buffer and density conditions, the final critical centrifugation step being carried out in a continuous sucrose density gradient ranging between 1.05 and 1.18 in density and in the presence of 10 µg/ml of Pronase, to produce a protease-resistant core PHF-fraction at the interface with a high density caesium chloride cushion. Tau protein can be released from the core PHF as an essentially pure preparation in the pH 5.5 supernatant (50 mmol. ammonium acetate) obtained after treating the PHF preparation with concentrated formic acid, lyophilisation, and sonication in pH 5.5 buffer.

Normal soluble tau can be isolated either from AD, control human brain tissues, or from animal brain tissues, with a post-mortem delay of less than 3 hours. Microtubule proteins are obtained by three cycles of temperature-dependent assembly-disassembly according to Shelanski et al. (1973, loc. cit.). Tau protein is purified from the thermostable fraction by gel filtration (Herzog and Weber (1978) Eur. J. Biochem., 92, 1–8). Alternatively, tau protein can be isolated by the procedure of Lindwall and Cole (1984; J. Biol. Chem., 259, 12241–12245) based on the solubility of tau protein in 2.5% perchloric acid.

The production of tau proteins and fragments can further be achieved by conventional recombinant DNA technology which are within the skills of an artisan in the field. Such techniques are explained further in the literature, see e.g. Sambrook, Fritsch & Maniatis "Molecular Cloning. A Laboratory Manual" (1989) Cold Spring Harbor Laboratory, N.Y. and Ausubel et al. "Current Protocols in Molecular Biology", Green Publish. Association & Wiley Interscience.

Further, DNA molecules or fragments thereof encoding complete or partial tau proteins may be obtained with the polymerase chain reaction (PCR) technique. Primers encoding 3' and 5' portions of relevant DNA molecules may be synthesised for the tau protein of interest and can be utilised to amplify the individual members of the tau protein family.

Preparation of tubulin proteins or fragments thereof are known in the art and are described e.g. by Slobada et al. (1976, in: Cell Mobility (R. Goldman, T. Pollard and J. Rosenbaum, eds.), Cold Spring Laboratory, Cold Spring Harbor, N.Y., pp 1171–1212).

The DNA sequences and DNA molecules may be expressed using a wide variety of host/vector combinations. For example. useful expression vectors may consist of segments of chromosomal, non-chromosomal and synthetic DNA sequences. Examples of such vectors are viral vectors, such as the various known derivatives of SV40, bacterial vectors, such as plasmids from E. coli, phage DNAs, such as the numerous derivatives of phage λ, M13 and other filamentous single-stranded DNA phages, as well as vectors useful in yeasts, such as derivatives of the 2µ plasmid, vectors useful in eukaryotic cells more preferably vectors useful in animal cells, such as those containing SV40, adenovirus and/or retrovirus derived DNA sequences.

As used herein, the term "DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal non translated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

As used herein, the terms "expression vector" and "expression plasmid" refer to a plasmid comprising a transcriptional unit comprising an assembly of (1) a genetic element or elements having a regulatory role in gene expression. for example, promoters or enhancers, (2) a structural or coding sequence which is transcribed into mRNA and translated into protein, and (3) appropriate transcription and translation initiation and termination sequences. Structural elements intended for use in various eukaryotic expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved form the expressed recombinant protein to provide a final product.

The host cell used for the expression of DNA sequence may be selected from a variety of known hosts. Examples for such hosts are prokaryotic or eukaryotic cells. A large number of such hosts are available from various depositories such as the American Type Culture Collection (ATCC) or the Deutsche Sammlung für Mikroorganismen (DSM). Examples for prokaryotic cellular hosts are bacterial strains such as E. coli, B. subtilis and others. Preferred hosts are commercially available mammalian cells such as mouse 3T3 cells, neuroblastoma cell lines such as NIE-115, N2A, PC-12, or the SV40 transformed African Green monkey kidney cell line COS, etc.

The tau protein produced by fermentation of the prokaryotic and eukaryotic hosts transformed with the DNA sequences of this invention can then be purified to essential homogeneity by known methods such as, for example, by centrifugation at different velocities, by precipitation with ammonium sulphate, by dialysis (at normal pressure or at reduced pressure), by preparative isoelectric focusing, by preparative gel electrophoresis or by various chromatographic methods such as gel filtration, high performance liquid chromatography (HPLC), ion exchange chromatography, reverse phase® chromatography and affinity chromatography (e.g. on SEPHAROSE™ (bead form gel prepared from agarose) Blue CL-6B or on carrier-bound monoclonal antibodies).

Figure 8:
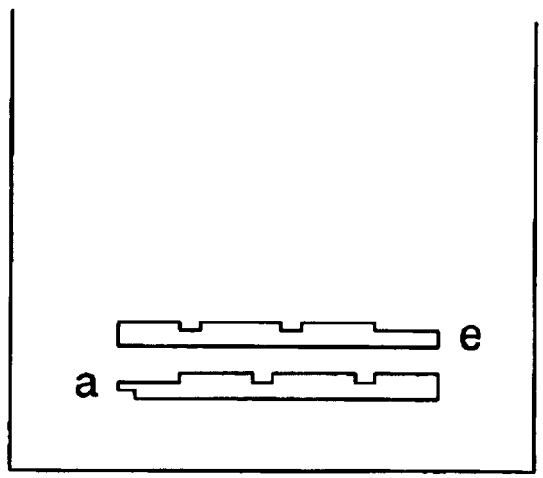
FIG. 8 shows a Tau binding assay configuration in which binding of two truncated units is measured—a species terminating at Ala390 ("a") and a second truncated tau species terminating at Glu-391 ("e").
Figure 10:
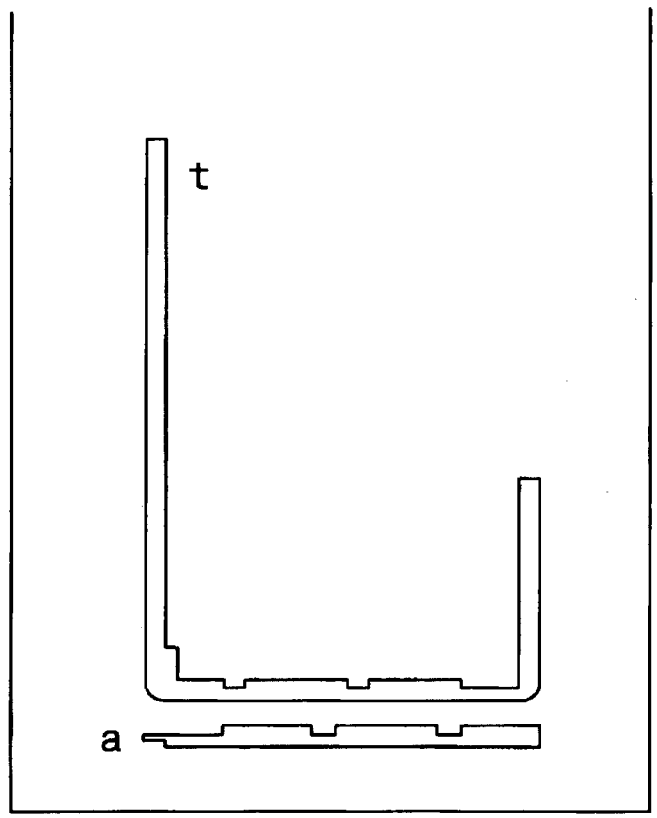
FIG. 10 shows the standard configuration for measurement of binding of full-length tau ("t") to the truncated core tau unit previously bound passively to the solid phase ("a").

According to the invention, a tau protein or a fragment thereof containing the tau core fragment is incubated with a tau protein together with an agent suspected of being capable of modulating or inhibiting pathological tau-tau association. The extent of tau-tau binding which is correlated to the capacity of inhibition of the agent may be detected by various methods:

In a preferred method a tau protein or a fragment thereof containing the tau core fragment is incubated with a tau derivative which is distinct, preferably immunologically distinct, from the first tau protein. In this case, binding of the tau derivative is detected for example via a poly- or monoclonal antibody or a derivative thereof. An example for this kind of detection is an assay method for the detection of tau-tau binding characterised in that a truncated tau protein corresponding to the core fragment is incubated together with a test substance and either a full-length tau protein or a truncated tau protein fragment simulating the core PHF tau unit in the aqueous phase (FIGS. 8 and 10).

In this case, tau-tau binding can be detected immunochemically in a conventional manner using an antibody which recognises the N-terminal segment of the full length tau protein or, for example, an antibody such as mAb 423 which recognises the core tau fragment truncated at Glu-391. Advantageously, the monoclonal antibody of the invention itself carries a marker or a group for direct or indirect coupling with a marker as exemplified hereinafter. Also, a polyclonal antiserum can be used which was raised by injecting the corresponding tau antigen in an animal, preferably a rabbit, and recovering the anti-serum by immunoaffinity purification in which the polyclonal antibody is passed over a column to which the antigen is bound and eluting the polyclonal antibody in a conventional manner.

A particularly advantageous embodiment of the method of the invention comprises the use of an antibody directed against a human-specific segment between Gly-16 and Gln-26 near the N-terminus of the tau protein. The use of this kind of antibody makes it possible to measure binding of full-length recombinant human tau to full-length tau isoforms derived from other animal species, for example rat, at various stages of development. The binding of truncated tau can be detected by using an antibody such as mAb 423 to detect a truncated core tau fragment terminating at Glu-391 binding to a similar fragment terminating at Ala-390 not recognised by mAb 423. (FIG. 8)

The antibodies or fragments thereof may be used in any immunoassay system known in the art including, but not limited to: radioimmuno-assays, "sandwich"-assays, enzyme-linked immunosorbent assays (ELISA), fluorescent immuno-assays, protein A immunoassays, etc.

Particularly preferred is the following configuration for tau-tau binding assays (FIG. 10): A tau fragment, preferably a recombinant tau fragment, corresponding to the truncated tau unit of the core PHF is bound to a solid phase, e.g. a conventional ELISA plate, in buffer conditions which have been shown not to favour tau-tau association. The truncated tau protein is preferably bound passively to the solid phase, since this has been found to expose the high affinity tau-tau binding site within the tandem repeat region. The solid phase is usually poly(vinyl-chloride), but may be other polymers such as cellulose, polyacrylamide, nylon, polystyrene or polypropylene. The solid supports may be in the form of tubes, beads, discs or micro plates, or any other surfaces suitable for conducting an assay, and which on passive binding of tau protein, exposes the high affinity tau capture site. Following binding, the solid phase-antibody complex is washed in preparation for the test sample.

Figure 9:
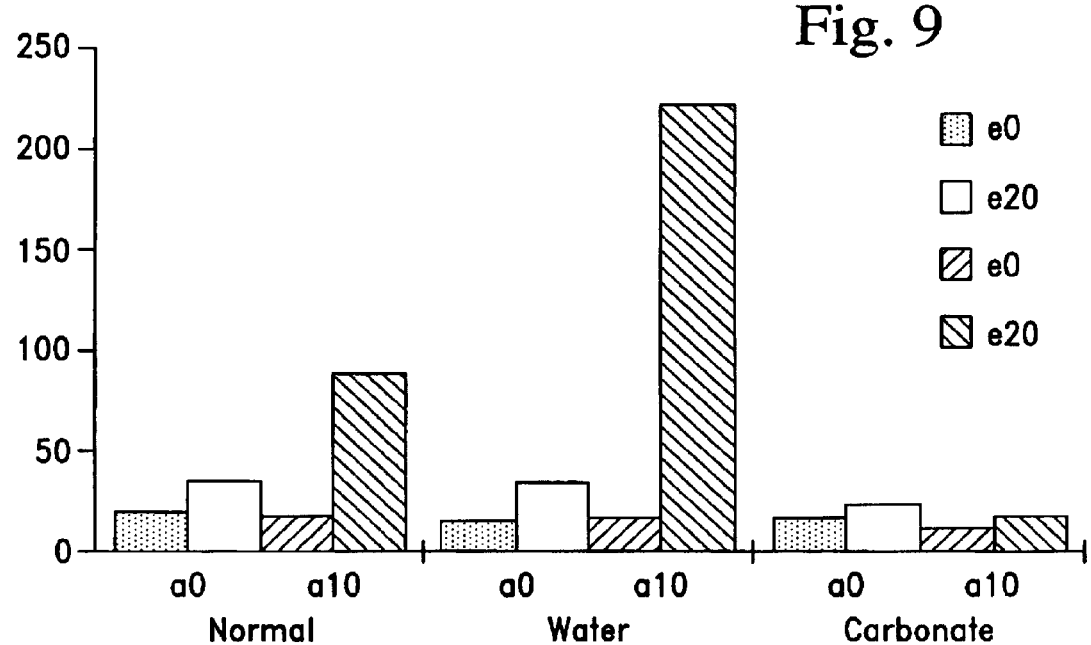
FIG. 9 shows the binding of species "e" to "a" in phosphate buffered normal saline ("normal"), distilled water ("water") and sodium carbonate buffer ("carbonate", 50 mM, pH 9.6).
Figure 12:
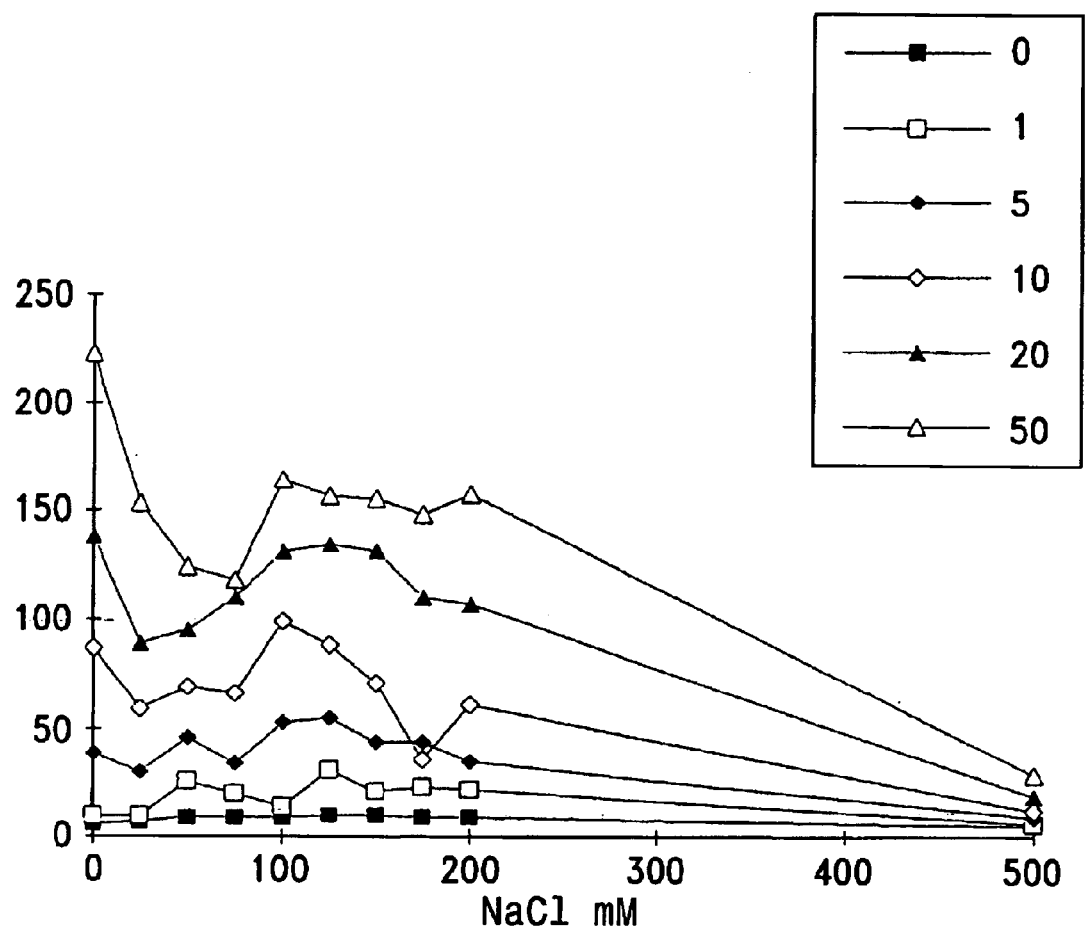
FIG. 12 shows the standard assay format shown in FIG. 10, with species "a" coated at 10 $\mu$g/ml and T40 added at the concentrations shown (range 0–50 $\mu$g/ml). binding was measured at constant pH (pH 7.4), while varying the sodium chloride concentration.

Surprisingly, appropriate buffer conditions for binding of the truncated tau unit of the core PHF to a solid substrate without self-association and without disturbance to the high affinity tau capture site within the tandem repeat region could be determined. An assay system was established as shown in FIG. 8, in which the core tau unit truncated at Ala-390 was first bound to the solid phase matrix. Next, a truncated unit terminating at Glu-391 was incubated. Only the latter could be detected as mAb 423 immunoreactivity. FIG. 9 demonstrates the specificity of the assay, in that mAb 423 immunoreactivity is seen only in the condition in which tau-tau binding is expected. An alkaline buffer (sodium carbonate, tris, etc.), preferably pH 9–10, e.g. sodium carbonate buffer (50 mM, pH 9.6) was found to be associated with negligible self association of core tau units (FIG. 9). Therefore plating of the core tau unit for passive binding to solid phase matrix was carried out in this buffer. If desired, a depolymerised tubulin preparation or a preparation of microtubules in the same buffer can be plated for passive binding for determination of tau-tubulin binding. Suitable agents for blocking excess binding sites are milk extract, bovine serum albumin, gelatine, etc. After transfer of the solid phase bound core tau unit to physiological buffer conditions and incubation with full-length tau in the standard binding assay format (FIG. 10), it was possible to demonstrate extremely high affinity capture of normal full-length tau protein. No binding of full-length tau was seen without prior plating of the core tau unit in the solid phase. When both species were present, binding was seen to depend on concentration of both species. It was found that when either the solid-phase or aqueous phase species was saturating, the binding constant for the other species was 8–25 nM, depending on the particular isoform of tau measured (FIG. 11). The buffer conditions for tau-tau binding should comprise suitable salt concentrations and suitable pH values (FIGS. 12 and 13). The salt concentrations for tau-tau binding should amount to preferably 50 to 400 mM sodium chloride, more preferably 100 to 200 mM sodium chloride or a corresponding salt or salt mixture with a comparable ionic strength. e.g. PBS (137 mM sodium chloride, 1.47 mM potassium dihydrogen phosphate, 8.1 mM disodium hydrogen phosphate, 2.68 mM potassium chloride). The pH range should comprise pH values of pH 4 to pH 10 and more preferably pH 5 to pH 8. In order to saturate excess binding sites and to avoid non specific binding the solid phase may be incubated with a blocking agent, e.g. milk extract, bovine serum albumin or preferably gelatine. After transfer of the passively bound core tau unit to physiological buffer conditions, it was possible to demonstrate extremely high affinity capture of normal full-length tau protein (Kd=8–25 nM, depending on the particular tau species tested).

A liquid phase containing a tau protein capable of binding to the tau protein of the solid phase is added together with the test substance to the solid phase tau protein for a period of time sufficient to allow binding. The bound tau complex is again washed in preparation for addition of the antibody which selectively detects the secondarily bound tau species, but not the initial solid-phase species. The antibody is linked co a reporter molecule, the visible signal of which is used to indicate the binding of the second tau protein species.

Alternatively, detection of binding may be performed with a second antibody capable of binding to a first unlabelled, tau specific antibody. In this case, the second antibody is linked to a reporter molecule.

By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognised, however, a wide variety of different conjugation techniques exist, which are well known to the skilled artisan. Commonly used enzymes include horseradish peroxidase, glucose oxidase, β-galactosidase and alkaline phosphatase, among others.

The substrates to be used with the specific enzymes are generally chosen for the production, upon hydrolysis by the corresponding enzyme, of a detectable colour change. For example, p-nitrophenyl phosphate is suitable for use with alkaline phosphatase conjugates; for peroxidase conjugates, 1,2-phenylenediamine or tetramethylbenzidine are commonly used. It is also possible to employ fluorogenic substrates, which yield a fluorescent product rather than the chromogenic substrates noted above. In all cases, the enzyme-labelled antibody is added to the corresponding tau-tau protein complex and allowed to bind to the complex, then the excess reagent is washed away. A solution containing the appropriate substrate, hydrogen peroxide, is then added to the tertiary complex of antibody-antigen-labelled complex. The substrate reacts with the enzyme linked to the antibody, giving a qualitative visual signal, which may be further quantitated, usually spectrophotometrically, to give an evaluation of the amount of antigen which is present in the serum sample.

Alternately, fluorescent compounds, such as fluorescein or rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic colour visually detectable with a light microscope. As in the enzyme immunoassay (EIA), the fluorescent-labelled antibody is allowed to bind to the first antibody-tau-peptide complex. After washing the unbound reagent, the remaining ternary complex is then exposed to light of the appropriate wavelength, and the fluorescence observed indicates the presence of the antigen.

In another preferred embodiment, the second tau protein species which is added in liquid phase together with a test substance may be linked to a reporter molecule as mentioned above. The second tau species may be directly modified (e.g. marked with a radioactive or enzymatically detectable label) or conjugated (e.g. to a fluorophore) in a domain of the molecule. for example the N-terminal segment, which is known not to be involved in the high affinity tau-tau binding site, and thereby itself function both as the ligand in the tau-tau binding assay, and as the reporter molecule.

A particular preferred embodiment of the present invention is described in detail in Example 1.

The antibodies or fragments thereof used in the method of the present invention may be produced by conventional techniques, i.e. monoclonal antibodies which are selective to tau epitopes may be prepared by the method of Köhler and Milstein. Suitable monoclonal antibodies to tau epitopes can be modified by known methods to provide Fab fragments or (Fab')$_2$ fragments, chimeric humanised or single chain antibody embodiments.

Examples for monoclonal antibodies being useful both to measure binding affinity in the tau-tau interaction, and to demonstrate the immunochemical relationship between the binding demonstrated in vitro and that which occurs in the human brain are presented in the following.

Monoclonal antibodies recognising an N-terminal or C-terminal tau epitope permit measuring of binding between truncated and full length tau species. Especially useful are antibodies recognising human specific epitopes. A monoclonal antibody (designated AK 499) recognises a human specific epitope located in the region between Gly-16 and Gln-26 of tau, and thereby also permits measurement of binding between full-length tau species, provided one is derived from a non-human source (Lai (1995) The role of abnormal phosphorylation of tau protein in the development of neurofibrillary pathology in Alzheimer's disease. PhD Thesis, University of Cambridge). Antibody 342 recognises an non-species specific generic tau epitope located between Ser-208 and Asn-265 (FIG. 21, SEQ ID NO: 4) which is partially occluded in the course of the tau-tau interaction (Lai, loc. cit.).

Figure 16:
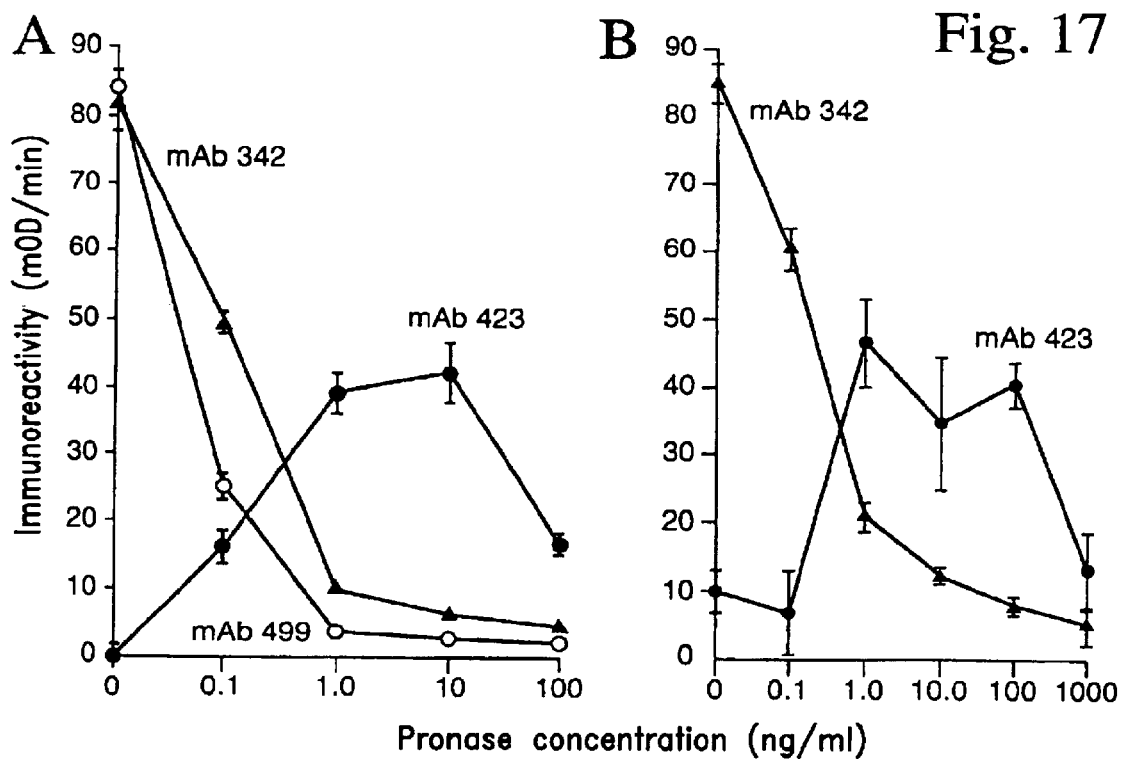
FIG. 16 shows a comparison of Kd values in the tau-tau binding assay using the species shown in the aqueous or solid phases.

Other useful antibodies have already been described: antibody 423 recognises tau C-terminally truncated at Glu-391 (Novak et al. (1993), loc. cit.). This truncation occurs naturally in the course of PHF assembly in Alzheimer's disease (Mena eral. (1995), (1996), loc. cit.; Novak et al. (1993), loc. cit.; Mena et al. (1991), loc. cit.). The same C-terminal truncation can be demonstrated in vitro after binding of full-length tau to a truncated tau fragment terminating at Ala-390, which is not recognised by mAb 423) (Novak et al. (1993), loc. cit.), followed by digestion with the broad-spectrum protease, Pronase (FIG. 16). In this configuration, the only possible source of mAb 423 immunoreactivity is from digestion of bound full-length tau, and this can be shown to increase in a concentration-dependent manner with increasing Pronase (FIG. 17A). This demonstrates that the molecular conformation of the tau-tau binding interaction generated in vitro corresponds precisely to that which occurs in the brain, and hence that selective inhibition of binding demonstrated in vitro can be generalised to the human brain.

Antibody 7.51 recognises a generic tau epitope located in the antepenultimate repeat of tau (Novak et al. (1991) Proc. Natl. Acad. Sci. USA, 88, 5837–5841), which is occluded when tau is bound in a PHF-like immunochemical configuration but can be exposed after formic acid treatment (Harrington et al. (1990), (1991), loc. cit.; Wischik et al. (1995a), loc. cit.). Normal soluble tau, or tau bound to microtubules, can be detected by mAb 7.51 without formic acid treatment (Harrington et al. (1991), loc. cit.; Wischik et al. (1995a), loc. cit.). Binding of full-length tau in the tau-tau binding assay is associated with partial occlusion of the mAb 7.51 epitope.

In practising the invention phenothiazines were identified which produced an inhibition of binding with a Ki of 98–108 nM (FIG. 19). Inhibition of 20% can be demonstrated at 1:1 molar ratio with respect to tau, and further inhibition is approximately linear in the range up to 10:1 molar ratio. These findings are consistent with the following assumptions: tau-tau binding is determined by a finite number of saturable binding sites, and hence is specific; there is no co-operativity, i.e. that the binding of one molecule of tau does not influence the binding of a further molecule of tau at the site at which inhibition occurs; binding is reversible, and is in a state of dynamic equilibrium in which binding is determined only by concentration and binding affinity.

Figure 20:
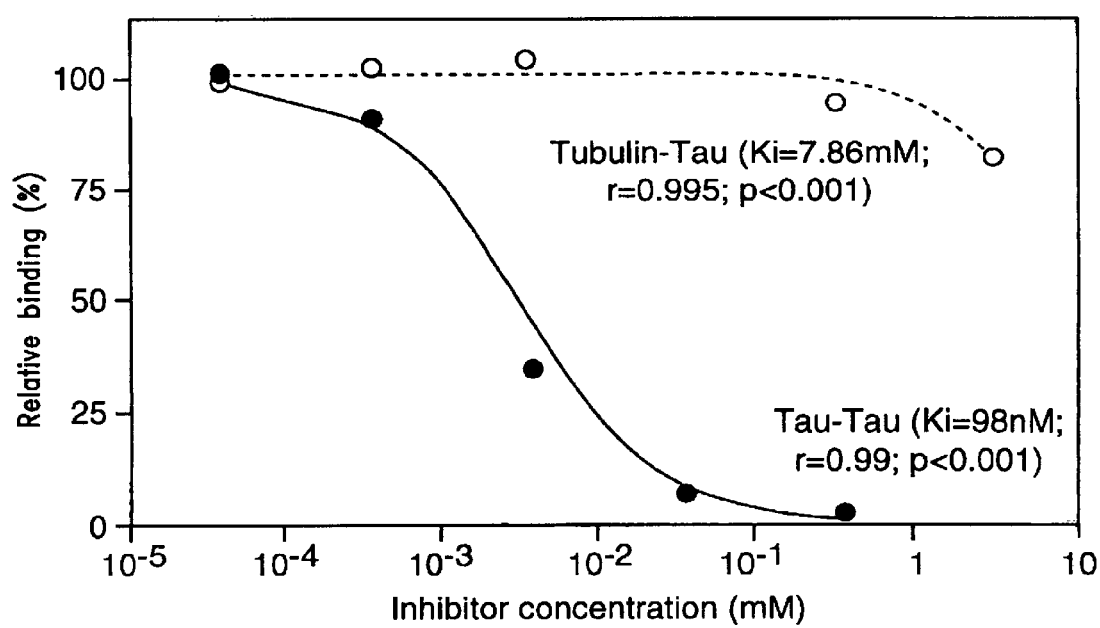
FIG. 20 shows selective inhibition of tau-tau-binding by thionine. Truncated tau protein was used in both aqueous and solid phases of the assay as in FIG. 8 (filled circles). In the tau-tubulin assay. depolymerised tubulin was coated (open circles), and tau was incubated with it.

Given that the tandem repeat region of tau normally functions as the tubulin binding domain, and that the same region of the molecule also contains the high affinity tau capture site responsible for PHF assembly, it would only be possible to envisage a pharmaceutical intervention to prevent pathological binding of tau if a more subtle molecular difference could be demonstrated between the two types of binding, which would permit selective inhibition of pathological tau-tau interaction, without inhibition of normal tau-tubulin binding, since many normal cellular processes, including particularly axonal transport of synaptic vesicles (Okabe and Hirokawa (1990) Nature, 343, 479–482), are dependent on the capacity of the cell the maintain tubulin in the polymerised state. Prior experiments demonstrated immunochemical differences (occlusion of the mAb 7.51 epitope in the tau-tau binding interaction, but no occlusion in the tau-tubulin binding interaction; Harrington et al. (1991), loc. cit.; Novak et al. (1991), loc. cit.) and molecular differences (tau bound in a PHF-like configuration shows a 14/16 amino acid residue phase-shift with respect to the normal tubulin-binding segment/linker segment organisation of the tubulin binding domain which can be demonstrated by characteristic N- and C-terminal proteolytic cleavage sites; Novak,et al. (1993), loc. cit., FIG. 3). Surprisingly, these differences could also provide a basis for pharmaceutical discrimination using small molecules within well-established pharmaceutical classes. In particular, the effects of the phenothiazines which were shown to inhibit pathological tau-tau association were tested for inhibition of normal tau-tubulin binding. Essentially no inhibition of binding could be demonstrated up to a molar ratio of 1000:1 with respect to tau (FIG. 20). Nevertheless, hyperphosphorylation of tau, which has been shown to inhibit the tau tubulin-binding interaction, was also shown to produce comparable inhibition in this tau-tubulin binding assay (Lai, loc. cit.). Thus, compounds provided by the present invention which inhibit pathological tau-tau association do not inhibit normal binding of tau to tubulin. This represents the critical discovery of the present invention, since it demonstrates the technical feasibility of discovering compounds on the basis of the screening system described herein which can distinguish pharmaceutically between the pathological binding of the tandem repeat region in the PHF and the normal binding of the tandem repeat region in the tau-tubulin interaction.

The only microtubule-associated protein identified so far within the PHF core is tau protein. Nevertheless, PHFs assemble in the somatodendritic compartment where the predominant microtubule-associated protein is MAP2 (Matus, A. In Microtubules (Hyams and Lloyd , eds) pp 155–166, John Wiley and Sons, NY). MAP2 isoforms are almost identical to tau protein in the tandem repeat region, but differ substantially both in sequence and extent of the N-terminal domain (FIGS. 25 and 26, SEQ D NO: 9 and 10). As shown in Example 3 aggregation in the tandem-repeat region is not selective for the specific tau core amino acid sequence, and the inhibitory activity of phenothiazine inhibitors such as thionine is not dependent on sequences unique to tau.

In addition, the present invention also relates to the corresponding in vivo methods. These methods refer to the screening for agents that modulate or inhibit pathological tau-tau association characterised in contacting a cell line transfected either with tau protein or a derivative thereof containing the tau core fragment or with a vector capable of expressing a tau protein or a derivative thereof containing the tau core fragment with an agent suspected of being capable of modulating or inhibiting tau-tau association followed by detection of the cell line viability and/or the cell line morphology.

Example 4 and 5 reveal that fibroblasts are fully viable when expressing transgenic full-length tau protein and the cytoskeletal distribution of transgenic full-length tau protein is not disturbed by culturing cells with a potent tau-tau binding inhibitor. The phenothiazine thionine does not appear to have substantial to intrinsic toxicity. But fibroblasts are either not viable or show gross morphological abnormalities when expressing the transgenic core tau unit of the PHF. The frequency of viable transfectants and the expression level for truncated tau are increased in a dose-dependent manner by growing cells in thionine following transfection. Viable transfectants expressing truncated tau are dependent on thionine, and revert to abnormal forms with low viability upon its withdrawal.

These findings therefore substantiate in a non-neuronal cell system the major findings of the present invention, namely: that high levels of PHF-core tau within the cell are toxic; that this toxicity can be reversed by compounds which are selective inhibitors of the pathological tau-tau binding interaction; and that such compounds do not disrupt the normal binding of tau to tubulin in vivo. These findings are generaliseable to other experimental models, including inducible transfection systems and direct transfection of cells with truncated tau protein.

Although the foregoing results support the use of tau-tau binding inhibitors in reversing the toxicity of the truncated tau unit, it is desirable to establish neuronal models of these processes. In general, neuroblastoma cell lines undergo complex cytoskeletal changes in the course of differentiation which depend on a balance between the development of the microtubule-network and a corresponding development of the neurofilament network. Higher molecular weight microtubule-associated proteins (MAP1A, MAP1B) are thought to provide cross-bridges between these cytoskeletal systems (Schoenfield et al. (1989) J. Neurosci. 9, 1712–1730). Direct interference with the microtubule-system with depolymerising agents (Wisniewski and Terry (1967) Lab. Invest. 17, 577–587) or aluminium (Langui et al. (1988) Brain Res. 438, 67–76) is known to result in intermediate filament collapse with formation of characteristic whorls in the cytoplasm (Wischik and Crowther (1986) Br. Med. Bull. 42, 51–56). A similar aggregation of the neurofilament cytoskeleton can be seen to occur spontaneously in neuroblastoma cell lines which fail to differentiate. The role of MAPs in the formation of these aggregates is not at present understood. However, the formation, accentuation and inhibition of these aggregates represent indirect markers of the capacity of microtubular cytoskeleton to associate with and transport the neurofilament cytoskeleton into newly formed neurites.

Examples 6 and 7 reveal that phenothiazine inhibitors like thionine are not toxic for neuronal cell lines at concentrations up to 2 μM and thionine does not interfere with incorporation of transgenic tau protein into the endogenous microtubule network. These phenothiazines are required for production of viable neuronal cell lines following stable transfection with a plasmid expressing truncated tau. Moreover, constitutive expression of truncated tau accentuates the formation of pNFH aggregates, whereas the latter is inhibited by expression of full-length tau. The formation of cytoplasmic pNFH aggregates is inhibited by phenothiazines like thionine and incorporation of pNFH immunoreactivity into neuronal processes is facilitated by these compounds.

These findings demonstrate that stable transfection of neuronal cell lines with truncated tau is inherently toxic and, by destabilising the microtubule system in surviving cells, results in the formation of presumptive neurofilament aggregates which fail to be transported into developing neurites. These effects can be inhibited by a compound selected for its capacity to block tau-tau aggregation in vitro, and this action is presumably mediated by a permissive effect on expression of endogenous tau or other MAPs required to stabilise microtubules. Phenothiazines like thionine also have the unexpected capacity to block neurofilament aggregation in untransfected cells, either by facilitating neuronal differentiation, or by directly inhibiting the formation of neurofilament aggregates. In addition to their potential utility in prevention of tau aggregation in Alzheimer's disease, such compounds may have additional potential utility in the treatment of diseases characterised by pathological neurofilament aggregation, such as motor neuron disease and Lewy body disease. Transgenic mice which overexpress neurofilament subunits have been found to develop neurofilament aggregates selectively in large motor neurones which undergo degeneration, leading to muscle wasting, and weakness (Cote et al. (1993) Cell 73, 35–46; Xu et al. (1993) Cell 73, 23–33). Other neurodegenerative disorders, Pick's disease and Progressive Supranuclear Palsy, show accumulation of pathological truncated tau aggregates respectively in Dentate Gyrus and in stellate pyramidal cells of the neocortex. The compounds which have been described also have utility in these neurodegenerative disorders.

Accordingly, the present invention especially relates to the above method wherein said cell line preferably is a fibroblast or a neuronal cell line, more preferably a fibroblast 3T3, a PC-12 or a NIE-115 cell line. These cell lines are transfected preferably with a truncated tau protein, containing at least the core tau unit. The expression of the tau protein may be under constitutive or under inducible control or the tau protein species may be directly transfected.

The present invention refers also to compounds which modulate or inhibit tau-tau association as obtainable by a any method described above.

Based on the above results, the present invention provides also the use of phenothiazines of the formula

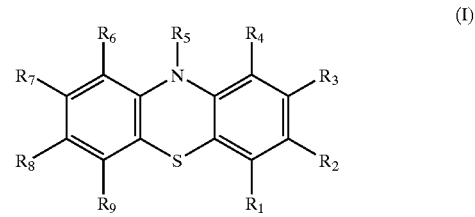

(I)

wherein:
$R_1$, $R_3$, $R_4$, $R_6$, $R_7$ and $R_9$ are independently selected from hydrogen, halogen, hydroxy, carboxy, substituted or unsubstituted alkyl, haloalkyl or alkoxy;
$R_2$ and $R_8$ are independently selected from hydrogen or

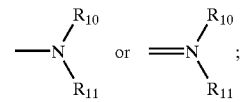

$R_5$ is selected form hydrogen, hydroxy, carboxy, substituted or unsubstituted alkyl, haloalkyl, alkoxy or a single bond;
$R_{10}$ and $R_{11}$ are independently selected from hydrogen, hydroxy, carboxy, substituted or unsubstituted alkyl, haloalkyl, alkoxy or a single bond;
and pharmaceutically acceptable salts thereof in the manufacture of a composition for the prophylaxis and treatment of pathological tau-tau or pathological neurofilament aggregation, and especially for the prophylaxis and treatment of Alzheimer's disease, motor neuron and Lewy body disease.

The term "alkyl" as used herein refers to straight or branched chain groups, preferably having one to eight, more preferably one to six, carbon atoms. For example, "alkyl" may refer to methyl, ethyl, n-propyl, isopropyl, butyl, isobutyl, sec-butyl, tert-butyl, pentyl, isopentyl, tert-pentyl, hexyl, isohexyl, and the like. Suitable substituents for the substituted alkyl groups used in the invention include the mercapto, thioether, nitro, amino, aryloxy, halogen, hydroxyl, and carbonyl groups as well as aryl, cycloalkyl and non-aryl heterocyclic groups.

The terms "alkoxy" refers to groups as defined herein above as alkyl groups, as the case may be, which also carry an oxygen atom interposed between them and the substrate residue to which they are attached.

The term "haloalkyl" represents a straight or branched alkyl chain having from one to four carbon atoms with 1, 2 or 3 halogen atoms attached to it. Typical haloalkyl groups include chloromethyl, 2-bromethyl, 1-chloroisopropyl, 3-fluoropropyl, 2,3-dibrombutyl, 3-chloroisobutyl, iodo-t-butyl, trifluoromethyl and the like.

The "halogen" represents fluoro, chloro, bromo or iodo.

Some compounds of the invention possess one or more asymmetrically substituted carbon atoms and therefore exist in racemic and optically active forms. The invention is intended to encompass the racemic forms of the compounds as well as any of the optically active forms thereof.

The pharmaceutically acceptable acid addition salts are formed between basic compounds of formula (I) and inorganic acids, e.g. hydrohalic acids such as hydrochloric acid and hydrobromic acid, sulphuric acid, nitric acid, phosphoric acid etc., or organic acid, e.g. acetic acid, citric acid, maleic acid, fumaric acid, tartaric acid, methanesulphonic acid, p-toluenesulphonic acid etc.

In a particular preferred embodiment the present invention provides the above phenothiazine wherein
$R_1$, $R_3$, $R_4$, $R_6$, $R_7$ and $R_9$ are independently selected from -hydrogen, —$CH_3$, —$C_2H_5$, or —$C_3H_7$;
$R_2$ and $R_8$ are independently selected from

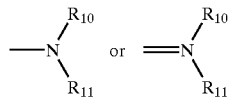

wherein $R_{10}$ and $R_{11}$ are independently selected from a single bond,
hydrogen, —$CH_3$, —$C_2H_5$ or —$C_3H_7$;
$R_5$ is a single bond, -hydrogen, —$CH_3$, —$C_2H_5$, or —$C_3H_7$ and pharmaceutically acceptable salts thereof.
Especially preferred are following phenothiazines:

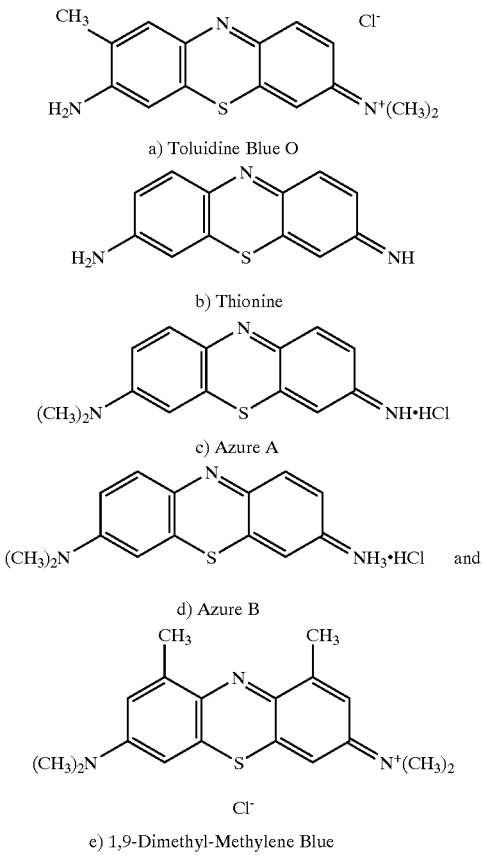

a) Toluidine Blue O b) Thionine c) Azure A d) Azure B e) 1,9-Dimethyl-Methylene Blue Compounds useful for the blocking of pathological tau-tau association, preferably phenothiazines (FIGS. 23 and 24), are characterised by a binding coefficient of less than 0.4, and lack of inhibition in the tau-tubulin binding assay, preferably up to a molar ratio of 1000:1 with respect to the molar concentration of tau.

The phenothiazines of the, present invention are known in the art and may be manufactured by the processes referred to in standard texts (e.g. Merck Manual,e Houben-Weyl, Beilstein E III/IV 27, 1214 ff, J. Heterocycl. Chem 21, 613 (1984), etc.).

The compounds of the above formula, their pharmaceutically acceptable salts, or other compounds found to have the properties defined in the assays provided, could be used as medicaments after further testing for toxicity (e.g. in the form of pharmaceutical preparations). The prior pharmaceutical use of methylene blue in a wide range of medical indications has been described, including treatment of methaemoglobineamia and the prophylaxis of manic depressive psychosis (Naylor (1986) Biol. Psychiatry 21, 915–920), and CNS penetration following systemic administration has been described (Müller (1992) Acta Anat., 144, 39–44). The production of Azure A and B occur as normal metabolic degradation products of methylene blue (Disanto and Wagner (1972a) J. Pharm. Sci. 61, 598–602; Disanto and Wagner (1972b) J. Pharm. Sci. 61, 1086–1094). The administration of pharmaceuticals can be effected parentally such as orally, in the form of tablets, coated tablets, dragees, hard and soft gelatine capsules, solutions, emulsions or suspensions), nasally (e.g. in the form of nasal sprays) or rectally (e.g. in the form of suppositories). However, the administration can also be effected parentally such as intramuscularly or intravenously (e.g. in the form of injection solutions).

For the manufacture of tablets, coated tablets, dragees and hard gelatine capsules the compounds of formula I and their pharmaceutically acceptable acid addition salts can be processed with pharmaceutically inert, inorganic or organic excipients. Lactose, maize starch or derivatives thereof, talc, stearic acid or its salts etc. can be used, for example, as such excipients for tablets, dragees and hard gelatine capsules.

Suitable excipients for soft gelatine capsules are, for example, vegetable oils, waxes, fats, semi-solid and liquid polyols etc.

Suitable excipients for the manufacture of solutions and syrups are, for example, water, polyols, saccarose, invert sugar, glucose etc.

Suitable excipients for injection solutions are, for example, water, alcohols, polyols, glycerol, vegetable oils etc.

Suitable excipients for suppositories are, for example, natural or hardened oils, waxes, fats, semi-liquid or liquid polyols etc.

Moreover, the pharmaceutical preparations can contain preserving agents, solubilizers, viscosity-increasing substances, stabilising a;gents, wetting agents, emulsifying agents, sweetening agents, colouring agents, flavouring agents, salts for varying the osmotic pressure, buffers, coating agents or antioxidants. They can also contain still other therapeutically valuable substances.

In accordance with the invention the compounds of the above formula and their pharmaceutically acceptable salts can be used in the treatment or prophylaxis of Alzheimer's disease, particularly for the blocking, modulating and inhibiting of pathological tau-tau association. The dosage can vary within wide limits and will, of course, be fitted to the individual requirements in each particular case. In general, in the case of oral administration there should suffice a daily dosage of about 50 mg to about 700 mg, preferably about 150 mg to about 300 mg, divided in preferably 1–3 unit doses, which can, for example, be of the same amount. It will, however, be appreciated that the upper limit given above can be exceeded when this is found to be indicated.

Figure 1:
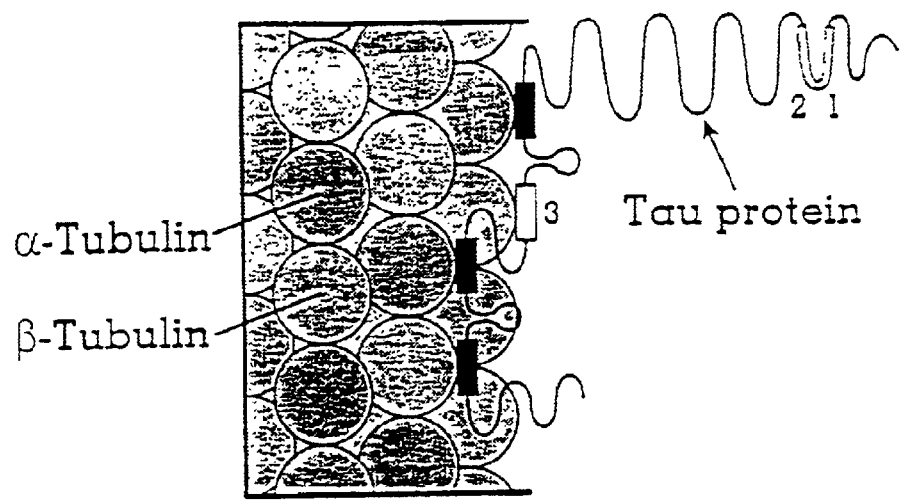
FIG. 1 represents tau protein binding to microtubules.

The invention can be understood better when they are read in conjunction with the accompanying figures:

FIG. 1: Representation of tau protein binding to microtubules (modified after Butner and Kirschner, loc. cit.).

FIG. 2: Schematic representation of tau protein isoforms, with corresponding amino acid and cDNA sequences shown in FIG. 21. The N-terminal domain of 252 residues contains either one or two inserts amounting to a further 58 residues ("1", "2"), followed by a tandem repeat region of 93–125 residues containing 3 or 4 tandem repeats, and a C-terminal tail of 64 residues. The tau fragments isolated from enriched protease-resistant PHF-core preparations are named "F5.5", and consist of a mixture of species derived from both 3- and 4-repeat isoforms, but encompassing 93–95 residues, the equivalent of 3-repeats, phase shifted by 14–16 residues with respect to the normal organisation of the tandem of tandem repeat region. All F5.5 species and normal tau are recognised by mAb 7.51, but mAb 423 recognises only those F5.5 fragments terminating at Glu 391. The positions of epitopes for mAb's 499, AT8 and 342 are also shown.

FIG. 3: N-terminal sequence analysis of the 12 kDa F5.5 fragment released from core PHF preparations revealed the presence of 6 distinct peptides which can be grouped into 3 pairs derived from 3-repeat (A: repeats 1–3; SEQ ID NO: 1) or 4-repeat (B: repeats 1–3; SEQ ID NO: 2, or C: repeats 2–4; SEQ ID NO: 3) isoforms (Jakes et at, loc. cit.). mAb423 immunoreactivity serves to define a C-terminal boundary at Glu-391 (shown by arrow, Novak et al. (1993), loc. cit.). The N- and C-terminal boundaries indicated by vertical arrows in FIGS. 3A to 3C thus serve to define a phasing of the tandem repeat region within the PHF core which is shifted 14–16 residues with respect to the sequence homology repeats. This minimal protease resistant core PHF tau unit is 93/95 residues long which is precisely equivalent to 3 repeats. The boundaries of this unit are also out of phase with respect to the tubulin binding domains proposed by Butner and Kirschner (loc. cit.), which are shown underlined.

Figure 4:
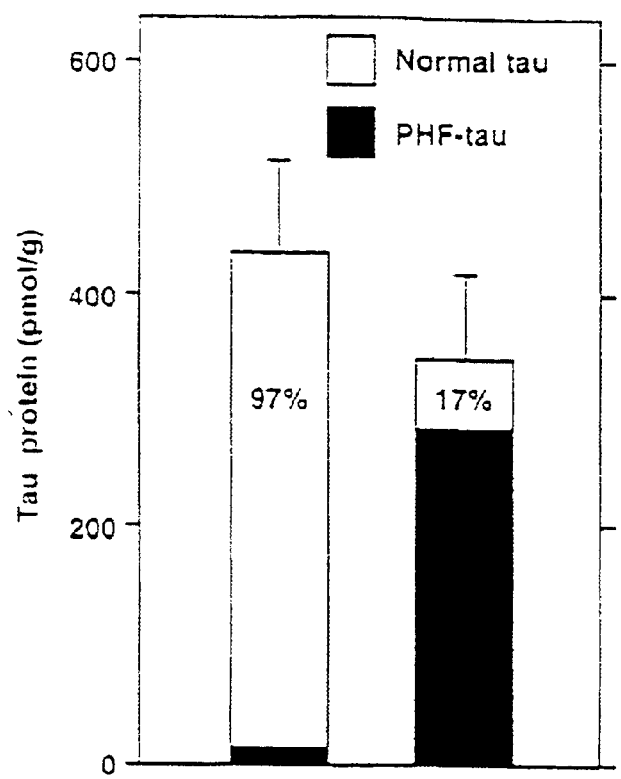
FIG. 4 shows the total (normal and PHF) tau protein content in controls and Alzheimer's disease.

FIG. 4: Total tau protein content in controls and Alzheimer's disease. Normal soluble tau (white) is the predominant form found in controls, whereas in Alzheimer's disease, the predominant form of tau is polymerised into PHFs (black).

Figure 5:
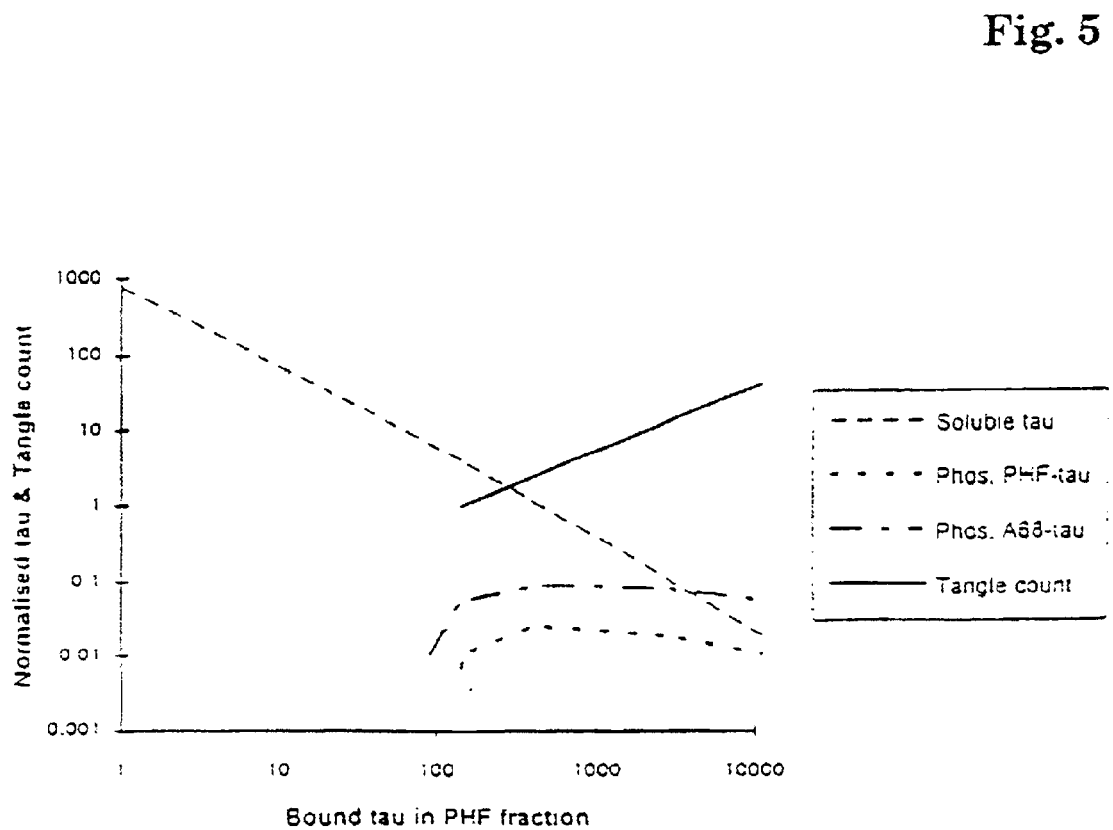
FIG. 5 shows the changes in soluble tau, phosphorylated tau, and tangle count during early stages of Alzheimer's disease.

FIG. 5: Changes in soluble tau, phosphorylated tau, and tangle count during early stages of Alzheimer's disease (Lai et al. (1995), loc. cit.). The accumulation of PHF-bound tau is shown on the horizontal axis. This is accompanied by a relative loss in normal soluble tau. The first appearance of phosphorylated tau is closely linked to the first appearance of tangles. However, both of these appear only after a substantial redistribution of tau from soluble to polymerised phases has already occurred.

Figure 6A:
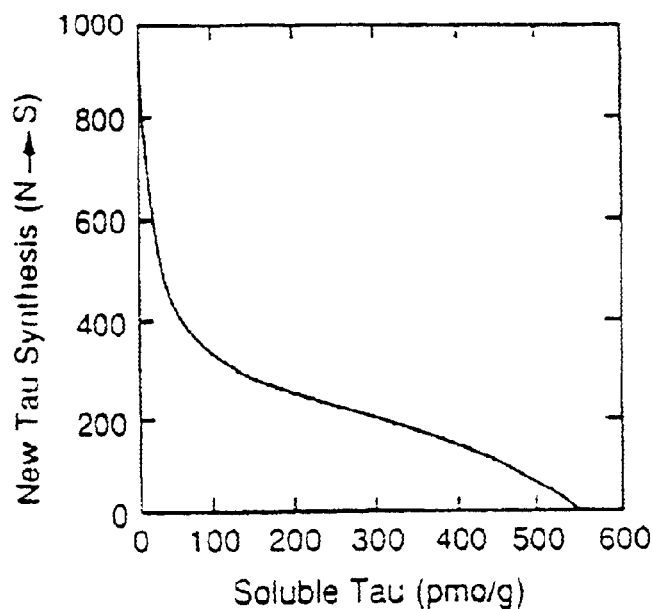
FIGS. 6A and 6B respectively show the calculated rates of transfer of new tau synthesis into the soluble tau pool, and of soluble tau into the PHF bound pool at early stages of Alzheimer's disease.
Figure 6B:
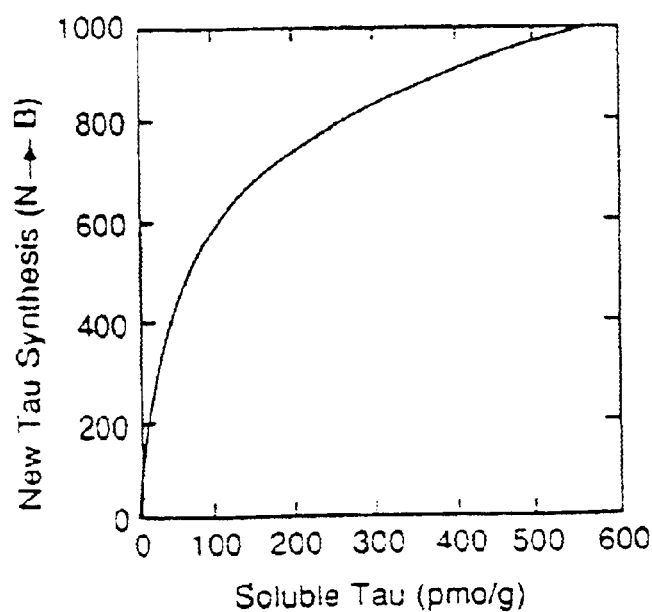

FIGS. 6A and 6B: Calculated rates of transfer of new tau synthesis into the soluble tau pool (FIG. 6A), and of soluble tau into the PHF-bound pool (FIG. 6B) at early stages of Alzheimer's disease (Lai et al. (1995), loc. cit.). As the soluble tau level drops below 580 pmol/g, progressively more new tau synthesis is required to keep pace with the rate of PHF production, and this appears to be regulated in a negative feedback manner with respect to the ambient level of soluble tau (FIG. 6A). The rate of transfer of soluble tau into PHFs is geometric with respect to the ambient level of PHF-tau (FIG. 6B).

FIG. 7: Hypothetical scenario for transformation of tau protein into PHFs in Alzheimer's disease. Once tau has been immobilised and truncated, a high affinity pathological tau capture site is exposed. When a further molecule of tau is captured, only partial proteolytic degradation is possible, since the region of high affinity tau-tau association is protected from proteolysis, leaving a further high affinity tau capture site available for the capture of a further tau molecule. The redistribution of the tau protein pool from soluble to truncated PHF-bound phases is autocatalytic, mediated by repetitive high affinity tau capture and partial proteolysis.

FIG. 8: Tau binding assay configuration in which binding of two truncated units is measured. The species terminating at Ala-390 ("a") is first coated on the ELISA plate (in sodium carbonate buffer: 50 mM, pH 9.6). Next, a second truncated tau species terminating at Glu-391 ("e") is incubated in various buffer conditions shown in FIG. 9. Only the species "e" is recognised by mAb 423, and hence mAb 423 immunoreactivity measures only that tau which is bound during the second incubation.

FIG. 9: Binding of species "e" (0 or 20 µg/ml) to "a" (0 or 10 µg/ml) in phosphate buffered normal saline ("normal"), distilled water ("water") and sodium carbonate buffer ("carbonate", 50 mM, pH 9.6). The vertical axis shows mAb 423 immunoreactivity. No immunoreactivity is detected when species "a" is coated alone, because mAb 423 does not recognise "a". No immunoreactivity is detected when "e" is incubated without prior plating of "a". This is because the blocking conditions used prevent non-specific binding of "e" to the ELISA plate. Immunoreactivity is only seen in the condition in which "a" and "e" are both present, demonstrating the specific detection only of "e" which is has been bound to "a". No binding is seen when "e" is added in sodium carbonate buffer. Therefore, this condition represents the optimal one for initial plating of "a", since self-aggregation is minimised in this condition.

FIG. 10: Standard configuration for measurement of binding of full-length tau ("t") to the truncated core tau unit previously bound passively to the solid phase ("a"). A recombinant tau fragment ("a") corresponding to the truncated tau unit of the core PHF is plated at varying concentrations on an. ELISA plate in conditions which have been shown not to favour tau-tau association (FIG. 9). After blocking, full length recombinant tau ("t") is plated in conditions which permit selective detection of tau-tau binding. Binding is detected by an appropriate antibody, which recognises an epitope located near the N-terminus of full-length tau. This antibody does not recognise "a".

FIG. 11: Determination of Kd for binding of full-length tau ("T40") to the truncated core tau unit terminating at Ala-390 ("a"), using mAb 499 to measure bound full-length human tau. The horizontal axis on the upper graph shows the concentration of T40 used and the vertical axis shows mAb 499 immunoreactivity. Each binding curve is obtained at a plating concentration of "a" which is shown. Without "a", there is no binding, confirming the absence of non-specific binding of T40 in the assay conditions used. Binding depends both on the concentration of T40 and the concentration of "a". The lower figure shows the calculated Kd corresponding to each plating concentration of "a". As the concentration of "a" becomes large, saturating conditions are approached assymptotically, and this represents the saturation Kd for binding of T40 to the truncated core tau unit, in this experiment determined as 22.8 nM.

FIG. 12: Using the standard assay format shown in FIG. 10, with species "a" coated at 10 µg/ml and T40 added at the concentrations shown (range 0–50 µg/ml), binding was measured at constant pH (pH 7.4), while varying the sodium chloride concentration. A plateau is observed in the vicinity of the physiological salt concentration of 137 mM. Binding is reduced at moderately low and high salt concentrations, although binding becomes more favourable at very low salt concentration.

FIG. 13: Similar experiment to that shown in FIG. 12, keeping the sodium chloride concentration constant at 137 mM. but varying the pH in the range 0–10. with binding in physiological phosphate-buffered normal saline ("PBS", pH 7.4) shown for comparison. Binding is reduced at extremes of pH. Binding shown detected by mAb's 499 and 342.

Figure 14:
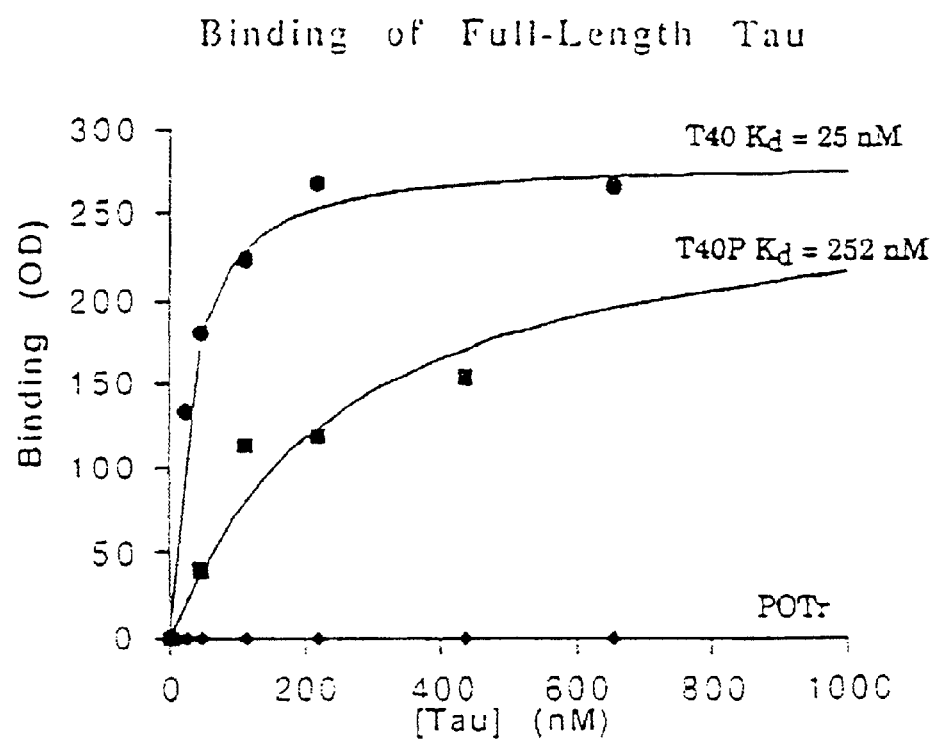
FIG. 14 shows typical sets of binding curves using the truncated core tau unit "a" in the solid phase, and incubating full length tau which has ("T40P") or has not ("T40") been phosphorylated. Fetal rat tau ("POTr") when introduced in the aqueous phase is shown to be incapable of pathological binding to the core tau unit.

FIG. 14: Typical sets of binding curves using the truncated core tau unit "a" in the solid phase, and incubating full length tau which has ("T40P") or has not ("T40") been phosphorylated in vitro using the method of Biernat et al.

(1992) EMBO J. 11, 1593–1597). The Kd was reduced by phosphorylation in this experiment by 10-fold, although varying the state of phosphorylation in the aqueous and solid phases systematically, the overall effect of phosphorylation can be shown to be on average 20-fold inhibition of binding. Although a fetal state of phosphorylation has been proposed by some as important for determining pathological tau-tau binding, fetal rat tau ("POTr") when introduced in the aqueous phase is shown here to be incapable of pathological binding to the core tau unit.

Figure 15A:
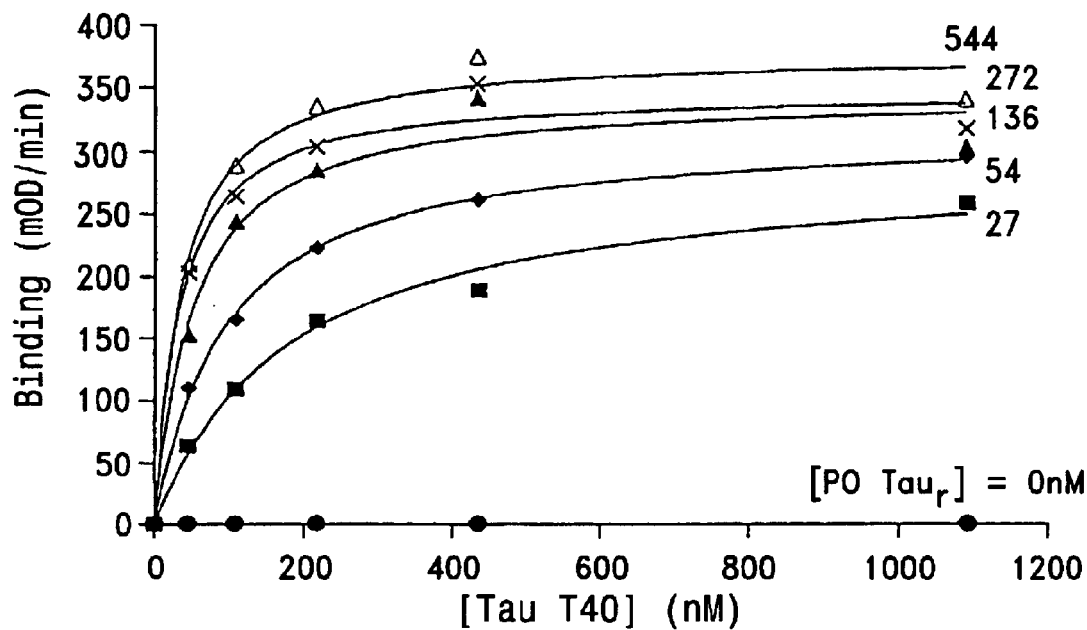
FIG. 15A shows a typical set of binding curves varying the concentration of full-length tau ("T40") and fetal tau ("PO Tau") in the concentration ranges shown. The derived assymptotic Kd is shown in FIG. 15B.
Figure 15B:
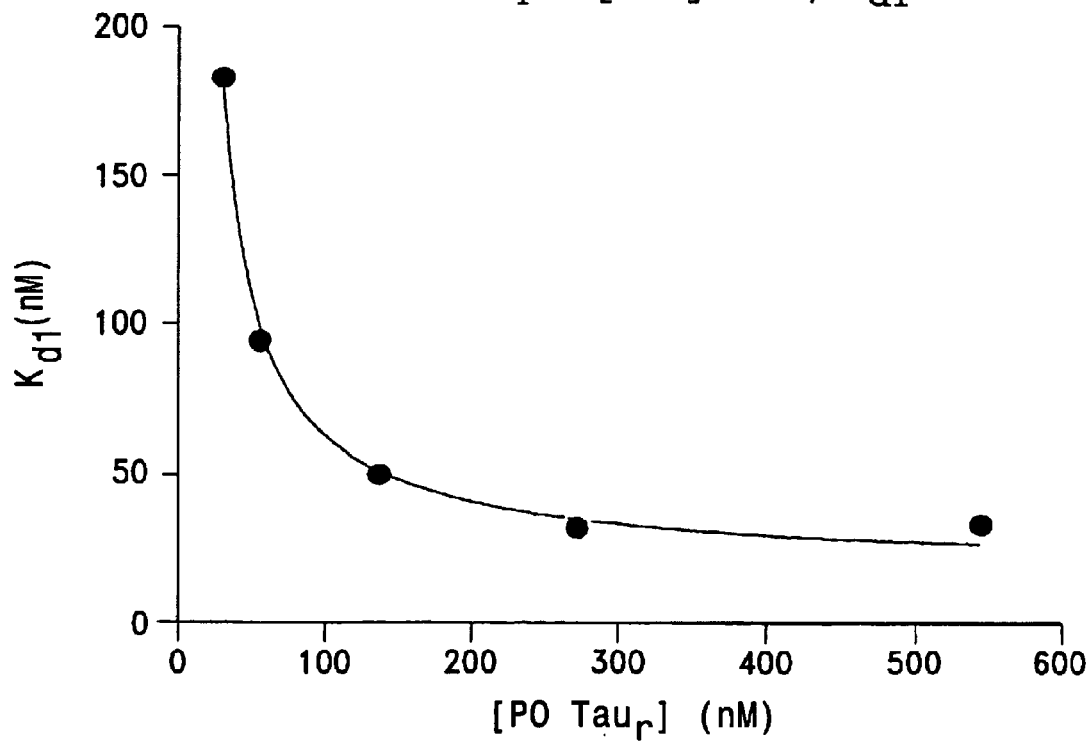

FIGS. 15A and 15B: By contrast with FIG. 14, after fetal tau has been bound passively in the solid phase, it is able to bind full-length unphosphorylated tau. A typical set of binding curves is shown in FIG. 15A, varying the concentration of full-length tau ("T40") and fetal tau ("PO Tau") in the concentration ranges shown. The derived assymptotic Kd is shown in FIG. 15B. As with binding of the full-length tau to the truncated core tau unit, binding of full-length tau to immobilised fetal tau has the same Kd of ~20 nM. Thus fetal tau, which does not bind to tau when it is present in the aqueous phase (FIG. 14), is converted into a tau-binding species simply by passive binding to the solid phase. Thus passive binding of tau to a solid matrix exposes the high affinity tau capture site.

FIG. 16: Comparison of Kd values in the tau-tau binding assay using the species shown in the aqueous or solid phases. Phosphorylation of full length recombinant tau used in the aqueous phase inhibits binding by a factor of 10-fold, and foetal/newborn tau from rat does not bind, as shown in FIG. 14. When newborn tau is used in the solid phase, T40 binds with the same affinity as to the truncated core PHF unit. Phosphorylation of T40 in the aqueous phase produces 30-fold inhibition of binding. Hyperphosphorylation of newborn tau in the solid phase inhibits binding to a comparable extent, and hyperphosphorylation in both phases produces 50-fold inhibition of binding. Therefore, contrary to the phosphorylation hypothesis, phosphorylation inhibits the pathological self-aggregation of tau protein in all configurations of the present assay.

FIGS. 17A, 17B and 17C: Proteolytic digestion of aggregated full-length tau protein. (FIG. 17A) Full-length tau (20 µg/ml) was bound to dGA (20 µg/ml) in PBS, washed, and incubated for 5 mm with Pronase in water at the concentrations indicated. Immunoreactivity was measured with mAb's 342 (Δ), 499 (o) and 423 (•). (FIG. 17B) Full length tau (10 µg/ml) which had self-aggregated in the solid phase in the absence of dGA was digested similarly, and immunoreacticity was measured with mAb's 342 (Δ) and 423 (•). In both cases, protease concentration-dependent loss of immunoreactivity with both mAb's 499 and/or 342 occurred with the acquisition of mAb 423 immunoreactivity. (FIG. 17C) The results from (FIG. 17A) are depicted schematically. Truncated dGA, initially coated on the hatched solid phase, binds full-length tau with high affinity through interaction via the repeat region. Both species lack the mAb 423 epitope prior to digestion. Proteolytic digestion of the complex (dotted lines) removes the N-terminal portion of the full-length tau molecule with loss of the mAb 499 and 342 epitopes located as shown. Acquisition of immunoreactivity with mAb 423 indicates truncation of full-length tau at Glu-391. The precise N-terminal extent of the proteolytically stable complex is unknown, but excludes the mAb 342 epitope immediately adjacent to the repeat region, and includes the tau-binding domain.

FIGS. 18A and 18B: Accumulation of truncated tau by repetitive tau capture. Beginning with the truncated tau fragment (dGA, 20 µg/ml) in the solid phase, full-length recombinant human tau (20 µg/ml) was bound, digested with Pronase (1 ng/ml) for 5 mm. washed, and the preparation was again incubated with further full-length tau (20 µg/ml) and again digested. This binding/digestion cycle was repeated four times; mAb 499 immunoreactivity was measured before and after, and mAb 423 measured only after, each Pronase digestion step. (FIG. 18A) Pronase digestion of the complex was associated with incremental accumulation of tau protein truncated at Glu-391 in the solid phase following each digestion cycle. (FIG. 18B) Binding of full-length tau was detected by the appearance of immunoreactivity for the N-terminus of tau (mAb 499), which was entirely abolished by Pronase digestion. In the subsequent incubation cycle, the binding capacity was increased for full-length tau incubated at a constant concentration in the aqueous phase. The incremental mAb 499 immunoreactivity cannot be explained by residual immunoreactivity left from the preceding cycle. Thus the proteolyticany stable complex left after Pronase digestion retains the capacity to bind further tau, and this binding capacity increases as truncated tau accumulates in the solid phase.

FIGS. 19A and 19B : Relative tau-tau binding (vertical axis) in the presence of increasing concentrations of prototype inhibitory phenothiazines (horizontal axis). This inhibition can be expressed in terms of a standard competitive inhibition model, with calculated Ki of 98–108 nM. The correlation coefficients for these approximations are 0.99, and are highly significant statistically, as shown. In FIG. 19A, the abscissa, represented as [A], refers to Azure A concentration. In FIG. 19B, the abscissa, represented as [B], refers to thionine concentration.

FIG. 20: Selective inhibition of tau-tau-binding by thionine. Truncated tau protein was used at 489 nM in both aqueous and solid phases of the assay as in FIG. 8 (filled circles). In the tau-tubulin assay, depolymerised tubulin was coated at 200 nM (open circles), and tau was incubated at 400 nM. Binding data could be described mathematically by a standard model which assumes competitive inhibition at the high affinity tau capture site. The $K_i$ values were calculated using the $K_d$ values obtained from the corresponding binding studies using full-length tau. Data points represent means of quadruplicate measurements.

FIGS. 21A and 21B: Nucleotide and predicted amino acid sequences of a human tau protein isoform (SEQ ID NO: 4). The sequence, deduced from cDNA clone htau40, differs from the previously determined three-repeat form (Goedert et al. (1988), loc. cit.) by an extra 58 amino acids inserted in the amino-terminal region (underlined) an by the previously described (Goedertet al. (1989), EMBO J. 8, 393–399) extra repeat of 31 amino acids (underlined). Nucleotides are numbered in the 5'–3' direction. The cDNA clone htau40 (Goedert et al. (1989b), Neuron 3, 519–526) contains the above sequence inserted into an Nde1 site (5'-end) and an EcoRl site 3' to the termination to the codon (* * *).

FIG. 22: Amino acid and cDNA sequence of PHF-core tau unit (SEQ ID NO: 6; Novak et al. (1993), loc. cit.), and primers (SEQ ID NO: 7 and 8) used in construction of the preferred core tau unit.

Figure 23:
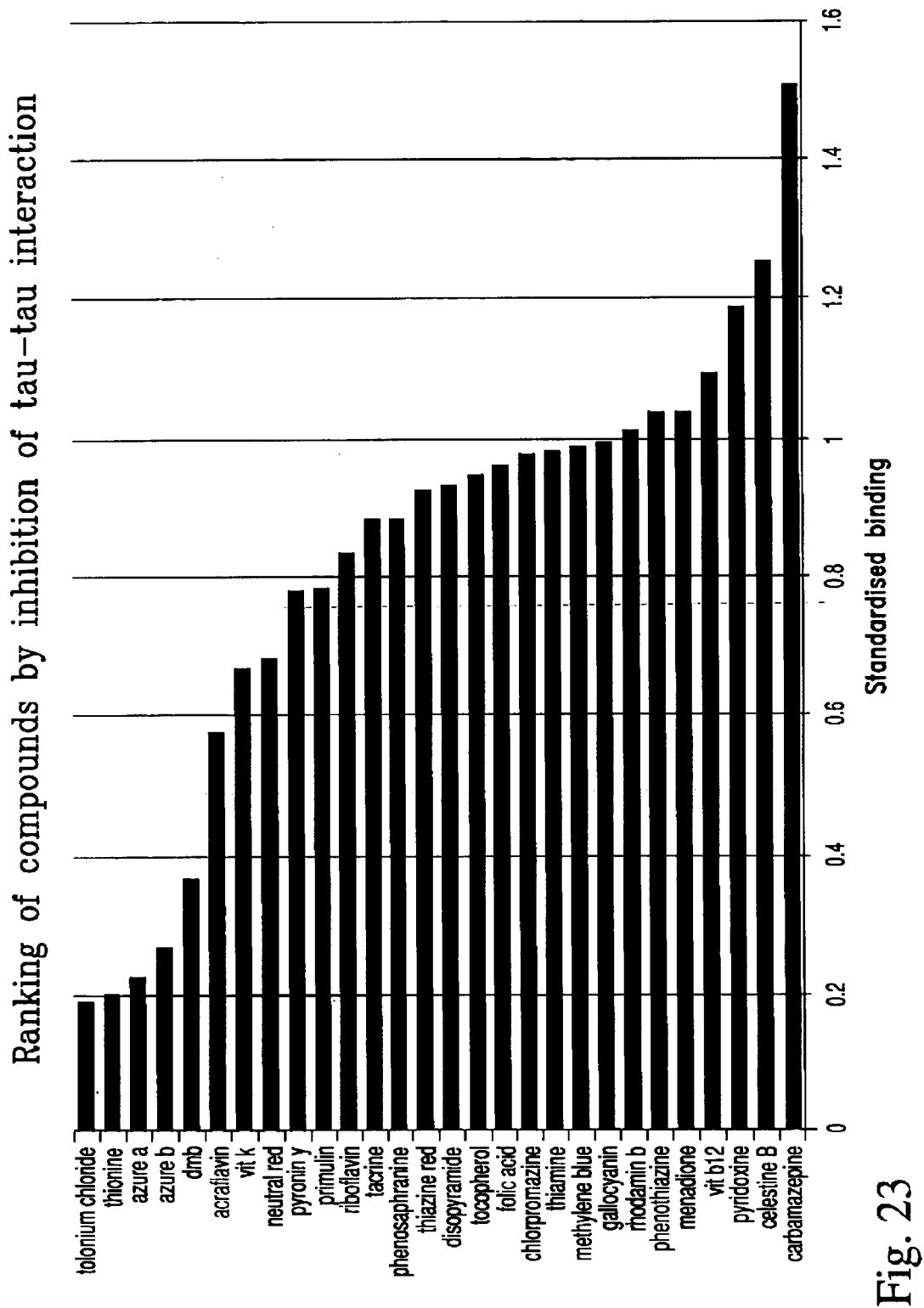
FIG. 23 shows the ranking of compounds by inhibition of tau-tau interaction. Ranking is based on the standardised binding relative to that seen in the absence of compound taken as the mean observed at 1 and 10 $\mu$g/ml.

FIG. 23: Ranking of compounds by inhibition of tau-tau interaction. Ranking is based on the standardised binding relative to that seen in the absence of compound taken as the mean observed at 1 and 10 µg/ml. In this ranking, "1" represents binding equivalent to that observed in the absence of compound, whereas "0.2" indicates that binding was reduced to a mean of 20% at test compound concentrations 1 and 10 µg/ml. Thus the lower the number the more effective the compound at inhibiting the binding of e and a.

As can be seen, the first five phenothiazines have standardised binding coefficients less the 0.4. That is, the binding seen in the range 1–10 µg/ml is less than 40% of that seen in the absence of compound.

FIGS. 24A–24D Chemical structures of the compounds tested with values for standardised binding according to FIG. 23.

FIG. 25: Schematic representation of tau, MAP2 (adult form), MAP2C (juvenile form) and high molecular weight tau (found in the peripheral nervous system and neuroblastoma cell lines). These proteins share similar microtubule-binding domains, but differ substantially in sequence and extent of the N-terminal projection domain. The juvenile forms of tau and MAP2 have only 3 of the tandem repeats. A 4-repeat form of MAP2 also exists.

FIG. 26: Sequence differences in the tandem repeat region of human tau (upper line; SEQ ID NO: 9) and mouse MAP2 (lower line; SEQ ID NO: 10). Vertical arrows show the limits of the truncated PHF-core fragment terminating at Glu-391, and the tubulin-binding segments are shown underlined.

FIG. 27: The pIF2 expression vector is an SV40-based eukaryotic expression vector (pSV2neo; Sambrook et al. (1989), loc. cit.; SEQ ID NO: 11 and 12 modified to contain a β-globin promotor driving the expression of foreign DNA (M. N. Neuberger). It has a neomycin resistance marker for Geneticin selection.

Figure 28:
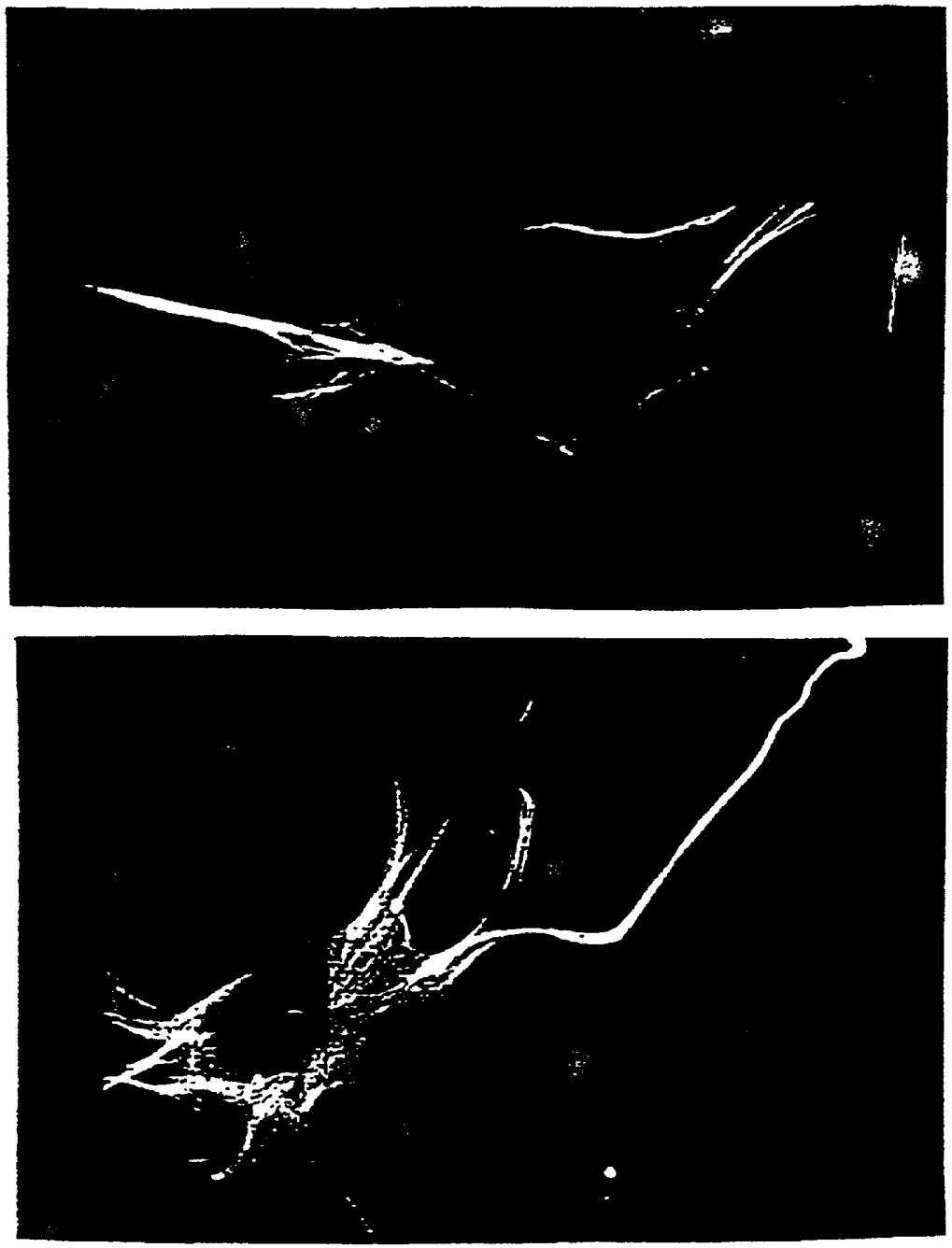
FIG. 28 shows mouse fibroblast 3T3 cells transfected with PIF2::T40, expressing full-length human tau protein (T40), immunolabelled by mAb 7.51 (upper figure) and mAb 499 (lower figure).

FIG. 28: Mouse fibroblast 3T3 cells transfected with PIF2::T40, expressing full-length human tau protein (T40). immunolabelled by mAb 7.51 (upper figure) and mAb 499 (lower figure). Cells form long slender processes, and tau immunoreactivity is also seen to have a cytoskeletal distribution in the perikaryon.

FIG. 29: Mouse fibroblast 3T3 cells transfected with PIF::dGAE, expressing the truncated PHF-core tau fragment terminating at Glu-391, immunolabelled with mAb 7.51. Early cell line transfected and grown without thionine. Cells are grossly abnormal, multinucleate, vacuolated, containing aggregates of tau protein in the cytoplasm.

Figure 30:
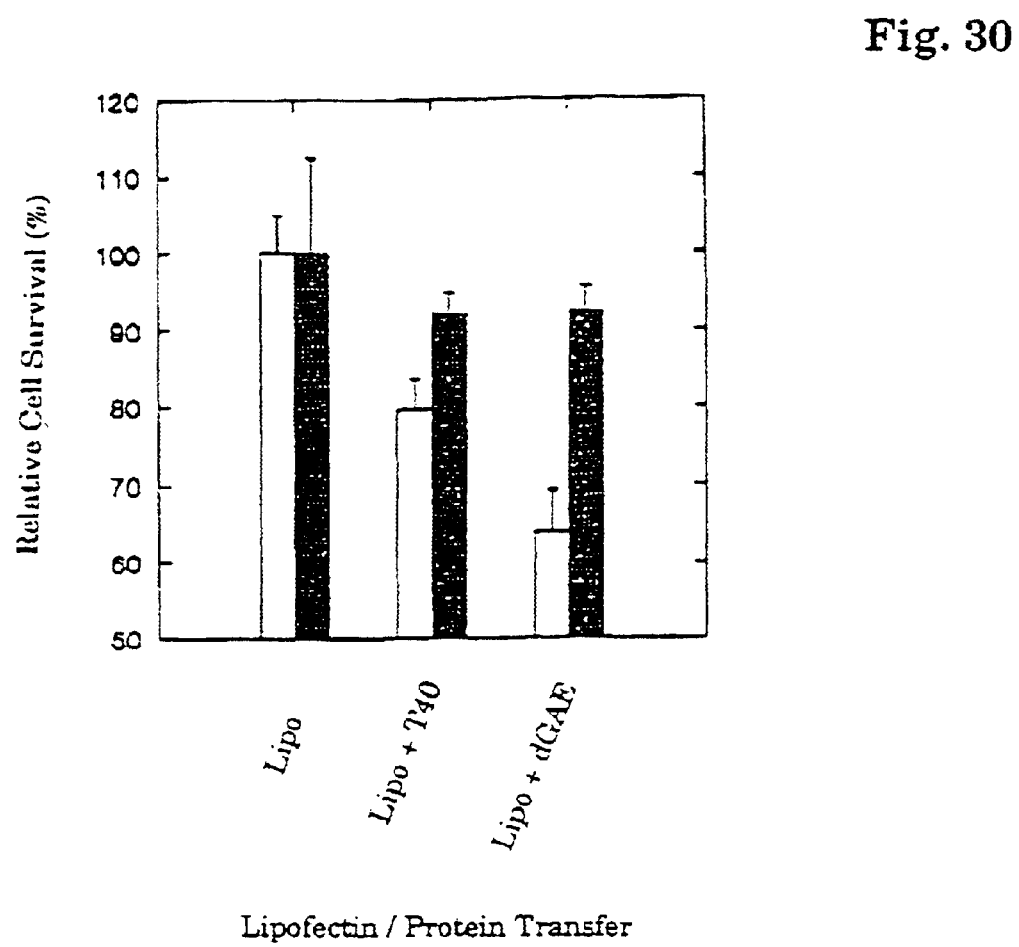
FIG. 30 shows lipofectin/tau protein transfers into 3T3 cells transfected with PIF2::T40. Relative cell survival is shown for approximately equimolar concentrations of full-length (T40) and truncated tau (dGAE), without (unshaded) or with shaded) thionine.

FIG. 30: Lipofectin/tau protein transfers into 3T3 cells transfected with PIF2::T40. Relative cell survival (normalised to cell counts after Lipofectin treatment without protein) is shown for approximately equimolar concentrations of full-length (T40, 220 nM) and truncated tau (dGAE, 300 nM), without (unshaded) or with shaded) thionine at 1 µM. Truncated tau is more toxic than full-length tau (p=0.02), despite the fact that at equimolar concentrations, the total protein load is 5× greater in the case of full-length tau.

Figure 31A:
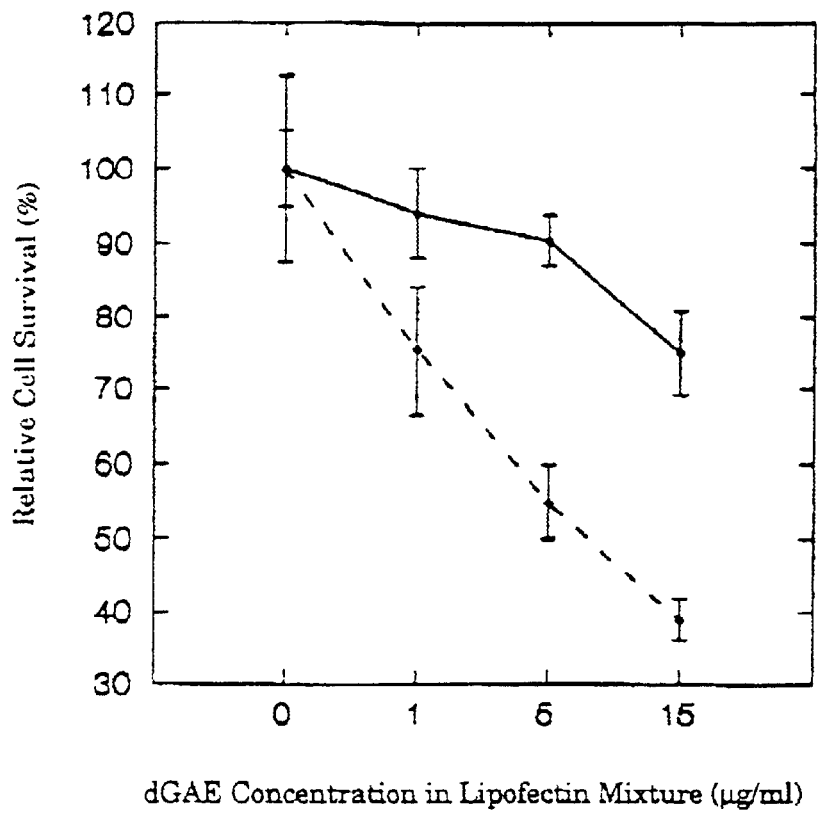
FIG. 31A shows reversal of truncated tau toxicity: the toxicity of truncated tau transferred via lipofectin into 3T3 cells expressing full-length tau is concentration dependent. Thionine (full-line) significantly reversed toxicity seen in the absence of thionine (broken line).
Figure 31B:
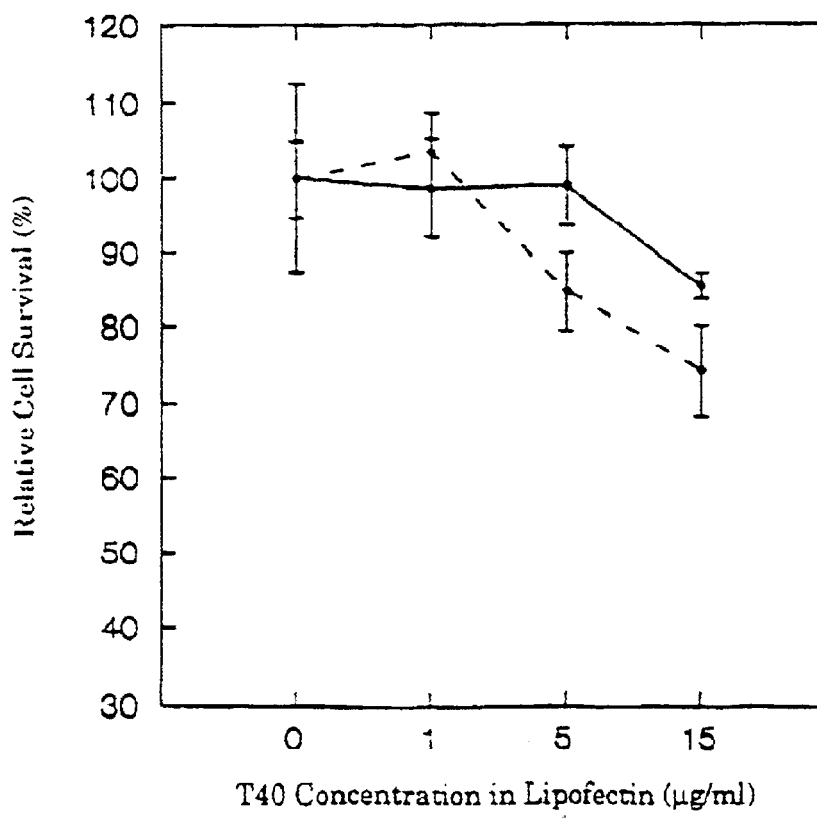
FIG. 31B shows a similar experiment in which full-length tau was transferred via lipofectin into 3T3 cells expressing full-length.

FIGS. 31A and 31B: (FIG. 31A) Reversal of truncated tau toxicity: The toxicity of truncated tau transferred via lipofectin into 3T3 cells expressing full-length tau is concentration dependent. Thionine (full-line) significantly reversed toxicity seen in the absence of thionine (broken line) at all three concentrations of truncated tau. (FIG. 31B) Similar experiment in which full-length tau was transferred via lipofectin into 3T3 cells expressing full-length. Both toxicity and thionine effects were much less apparent.

The following Examples are intended to illustrate details of the invention, without thereby limiting it in any manner.

EXAMPLES

Example 1

Tau-Tau-Binding Assay

The assay is carried out in a 96-well PVC microtitre plate, with solutions added and readings taken with respect to individual wells:

a) A 50 µl solution of purified truncated tau peptide at varying concentrations ranging 0–50 µg/ml (0, 1, 5, 10, 50 µg/ml) in 50 mM sodium carbonate buffer (pH 9.6) is added to each well and incubated 1 hr at 37° C.

b) The microtitre plate wells are washed 3× with water with or without 0.05% TWEEN™ (polyoxyethylene derivatives of sorbitan esters).

c) A 200 µl solution of 2% milk extract ("Marvel") made up in phosphate-buffered normal saline ("PBS", 137 mM sodium chloride, 1.47 mM potassium dihydrogen phosphate, 8.1 mM disodium hydrogen phosphate, 2.68 mM potassium chloride) is added to each well and incubated for 1 hr at 37° C.

d) The plate is washed as in b).

e) A 50 µl solution of full-length recombinant tau (T40) in the same range of concentrations as in a) above in 1% gelatine, 0.05% TWEEN™ (polyoxyethylene derivatives of sorbitan esters) in PBS is added to each well, and incubated for 1 hr at 37° C.

f) The plate is washed as in b).

g) A 50 µl solution of monoclonal antibody 499 is added at A dilution of the tissue culture supernatant with 2% milk extract ("Marvel") in PBS is added to each well and incubated for 1 hr at 37° C.

h) The plate is washed as in b).

i) A 50 µl solution of second antibody (blotting grade affinity purified goat anti-mouse lgG (H+L) conjugated with horseradish peroxidase—Biorad catalogue number 170-6516) at 1/1000 dilution in PBS with 0.05% TWEEN™ (polyoxyethylene derivatives of sorbitan esters) is added to each well and incubated for 1 hr at 37° C.

j) The plate is washed 3× with a 0.05% solution of TWEEN™ (polyoxyethylene derivatives of sorbitan esters) in water, followed by a single wash with water.

k) Preparation of colour development solution is as follows. Dissolve 10–15 mg of 3,3',5,5'-tetramethylbenzidine (TMB; BCL catalogue number 784 974) in dimethylsuphoxide to a final concentration of 10 mg/ml (TMB solution). Add 10 ml sodium acetate stock (0.5 M, pH 5.0) to 90 ml of water. While swirling, slowly add 1 ml TMB solution, followed by 10 µl hydrogen peroxide.

l) A 50 µl solution of TMB solution is added to each well to develop the peroxidase colour reaction, the rate of development of which is read over 2 mm. at 650 nm, in a Molecular Devices Microplate reader using Kinetic L1 Softmax software package.

Example 2

Preparation of Recombinant Tau Fragments

Tau cDNA was generated using standard protocols (Sambrook et al., loc. cit.) from mRNA isolated from brain tissue of an Alzheimer patient whose tissue was obtained 3 h after death. The cDNA library was screened with synthetic 17-mer oligonucleotide probes derived from the sequence from part of a PHF core protein (Goedert et al. (1988), loc. cit.). Full length cDNA clones were subcloned into the EcoRI site of M13mp18 and site-directed mutagenesis used to introduce a NdeI site in the context of the initiator codon. Following cleavage with NdeI and EcoRI, the resulting cDNA fragments were subcloned downstream of the T7 RNA polymerase promotor into NdeI/EcoRI-cut expression plasmid pRK172 (McLeod et al. (1987) EMBO J., 6, 729–736). pRK172 is a derivative of pBR322 that is propagated at very high copy number in E. coli due to removal of the pBR322 copy number control region. The plasmid carries an ampicillin resistance gene for selection of recombinant clones.

Constructs coding for truncated forms of tau were prepared from mRNA as described in Novak et al. (1993, loc. cit.). The mRNA was used as a template for polymerase chain reaction (PCR) using specific oligonucleotide primers. The sense primer contained an NdeI site and the anti-sense, an EcoRI site. PCR fragments were subcloned into pRK172 as described above. The primers used for construction of dGAE are given in FIG. 22. The authenticity of all DNA fragments used for expression was confirmed by full length sequencing of both strands.

Details for the construction of htau40 ("T40") cDNA are described in (Goedert et al. (1989), loc. cit.). This sequence is the largest form of tau found in the CNS and encodes tau protein that contains both the 2 N-terminal inserts of 29 amino acids each and an extra 31 amino acid repeat in the tubulin-binding domain. The DNA sequence and its predicted amino acid sequence are shown in FIG. 21 (SEQ ID NO: 4).

Recombinant plasmids were used to transform E. coli BL21 (DE3) a strain used for prokaryotic expression which carries a chromosomal copy of the bacteriophage T7 RNA polymerase acne under control of the lacUV5 promotor (Studier and Moffat (1986), J. Mol. Biol. 189, 113–130). Exponentially growing cultures were induced with IPTG (iso-propyl thiogalactoside) for 3 h.

Large-scale purification (1 liter bacterial culture) of tau fragments was carried out as described by Goedert and Jakes (1990, EMBO J., 9, 4225–4230), with minor modifications. Cells were disrupted by rapid freezing of the cell pellet in liquid nitrogen. The pellets were then suspended in buffer containing 50 mM PIPES, 1 mM dithiothreitol (DTT) (pH 6.8). The thermostable proteins in the supernatant were dialysed against PIPES/DTT, then applied co a column containing phosphocellulose equilibrated in the same buffer. Tau protein was eluted with a gradient of NaCl (0–0.5M) in the above buffer. Fractions were analysed by SDS-PAGE and both Coomassie staining and immunoblotting. Those fractions containing tau were pooled, dialysed against 25 mM MES, 1 mM DTT (pH 6.25) and stored at −20° C. at approximately 5 mg/ml. Protein concentrations were measured by the Lowry method (Harrington (1990), loc. cit.).

Example 3

Binding of Foetal MAP2C to Truncated and Full Length Tau

One possible explanation for the lack of MAP2 in PHFs might be that MAP2 in PHFs might be MAP2 is unable to bind to the core tau unit of the PHF because of sequence differences in the repeat regions. This was examined experimentally using the standard binding assay in two configurations: truncated tau in the solid phase with foetal MAP2C in the aqueous phase, and MAP2C in the solid phase with full-length tau in the aqueous phase. Binding could be demonstrated in both configurations, ant thionine blocked the tau/MAP2 binding interaction. Thus, aggregation in the tandem-repeat region is not selective for tau, and the inhibitory activity of phenothiazine inhibitors such as thionine is not dependent on sequences unique to tau. The reason why MAP2 is not found in PHFs is at present unknown, but factors may include the contribution of the large N-terminal domain found in the adult form of MAP2, compartment differences within the cell, or other differences in processing or the MAP2 molecules.

Example 4

Transfection of Mouse 3T3 Cells with Human Tau Protein

Mouse fibroblast 3T3 cells were transfected with a eukaryotic expression vector (pIF2) containing full-length and truncated forms of tau protein under constitutive control by a β-globin promotor . This vector contains a neomycin resistance gene as a selectable marker (pSV2neo; Sambrook et al. (1989), loc. cit.; modified by M. N. Neuberger). Cells were cultured in defined minimal essential mixtures (DMEM) containing antimicrobial agents and 10% foetal calf serum at 37° C. in an atmosphere of 5% $CO_2$. They were transfected with plasmid DNA either using a standard calcium phosphate protocol or by lipofection (according to manufacturers protocol; Gibco BRL). Cells which had integrated the plasmid DNA were selected by viability in medium containing Geneticin (0.5 mg/ml; Southern and Berg (1982), J. Mol. Appl Genet. 1, 327).

Stably transfected 3T3 fibroblast expressing full-length tau protein were readily produced. Expression could be demonstrated histologically using generic (mAB 7.51) and human-specific (mAB 499) anti-tau antibodies (FIG. 28). and by immunobiot of cell extracts (not shown). Two viable cell lines were produced when the transfection was carried out using the same vector carrying the truncated core tau unit. Truncated tau could be demonstrated within these cells histologically, but the morphology of these cells was grossly abnormal compared to those expressing full-length tau (FIG. 29). Abnormalities included failure of process development, formation of large rounded cells, cytoplasmic aggregation of tau and vacuolation of the cytoplasm. However, these cells proved unstable, and readily reverted to forms failing co express truncated tau protein despite the continued presence of Geneticin. The toxicity of truncated tau might be explained either by the accumulation of toxic tau-tau aggregates in the cell or by the binding of truncated tau to endogenous mouse MAPs essential for the cell.

Example 5

Growing of Tau-Transfected Cells in the Presence of Phenothiazine Inhibitors

The toxicity of the truncated core tau unit might be reversible in part if the prototype phenothiazine inhibitors could be used to block self-aggregation in vivo. This would be feasible only if the compounds were not intrinsically toxic at concentrations needed to block tau-tau binding,. The inhibitors with the lowest toxicity in 3T3 cells were thionine and acriflavin. and cells could survive prolonged exposure to these compounds at concentrations substantially in excess of the $K_i$ values (100 nM) for inhibition of tau-tau binding in vitro. In practice, 3T3 cells could be grown several month in the presence of 2 $\mu$M thionine.

The influence of thionine on the tau-tubulin binding interaction was examined in vivo by culturing 3T3 fibroblast transfected with full-length tau protein in the presence of thionine at a range of concentrations. Disruption of normal cytoskeletal distribution of tau immunoreactivity was seen at concentrations in the range 4–8 $\mu$M, comparable with the known $K_i$ for inhibition of the tau-tubulin binding interaction in vitro (8 $\mu$M), but no effect was seen over the concentration range at which transfected 3T3 cells were routinely cultured (0.5–2 $\mu$M). These findings demonstrate the feasibility of culturing transfected cell lines in the presence of prototypic inhibitor without detriment either to cell viability or to the normal cytoskeletal distribution of transgenic full-length tau protein.

Growing transfected cells in the presence of inhibitors of tau-tau binding was found to increase the viability of cells transfected with truncated tau in a dose-dependent manner. The number of viable cell lines transfected with truncated tau increased when the cells were grown in the presence of higher concentrations of thionine. Furthermore, the strength of expression of truncated tau, measured by immunohistochemistry on a semiquantitative scale, was found to increase as a function of the thionine concentration used following transfection.

The morphology of 3T3 cells and the distribution of truncated tau protein were much less abnormal when transfected cell lines were produced in the presence of thionine. Truncated tau protein appeared to follow the distribution of the endogenous microtubule network, but the tau staining had a more broken character than seen with full length tau. Cells expressing high levels of truncated tau were found to form aggregates with gross disruption of the cell cytoplasm when thionine was removed. This was similar to the initial findings for cells transfected in the absence of thionine.

Example 6

Untransfected Neuronal Cell Lines

Neuronal cell lines (N2A, NIE-115) were cultured in DMEM containing 2% or 10% foetal calf serum and 5% horse serum on tissue culture plates coated with collagen. These were all grown at 37° C. in an atmosphere containing 5% $CO_2$. Initial immunohistochemical studies of neuronal cell lines prior to transfection led to the identification of cytoplasmic aggregates immunoreactive with mAb 423 forming in the cytoplasm of undifferentiated neuroblastoma cells (N2A cells) and in PC-12 cells after brief treatment with dibutyryl-cAMP (db-cAMP, known to differentiate neuroblastoma cells in tissue culture). These structures were shown to be immunoreactive with an antibody recognising neurofilament protein (NFH; SMI-31, Sternberger et al. (1985) PNAS 82, 4274–4276) and more sparsely immunoreactive with an antibody recognising NIAPlA. which is known to bind neurofilaments. In the course of differentiation, this endogenous mAb 423 immunoreactivity was seen to shift from the cytoplasm to neurites. Immunoprecipitation of mAb423 immunoreactivity from these cells led co the identification of a species with gel mobility of 230 kDa which was recognised by SMI-31. These results suggest that the structures recognised by mAb 423 in rodent neuronal cell lines include the high molecular weight neurofilament protein in an aggregated state, but do not exclude the possibility that they also include altered MAPs. We refer to them as presumptive-NFH aggregates (pNFH). Dose-dependent inhibition of pNFH aggregates in the cytoplasm could be demonstrated with thionine in untransfected PC-12 cells.

Example 7

Transfection of Neuronal Cell Lines with Full-length and Truncated tau Proteins and Effects of Tau Aggregation Inhibitors A. PC-12 Cells PC-12 cells were transfected with the pIF2 vector containing either the PHF-core tau fragment truncated at Glu-391 or full-length tau protein. As with 3T3 fibroblasts, no viable cell lines transfected with truncated tau were produced unless cells were grown in thionine following transfection. Once stabilised, transfected cell lines were analysed in the presence or absence of db-cAMP and in the presence and absence of thionine. Two end-points were examined: formation of cytoplasmic pNFH aggregates, and distribution of pNFH immunoreactivity into neurites.

Brief incubation with db-cAMP increased the proportion of cells containing neurofilament aggregates from 9% to 37% (p<0.001). This effect was seen both in cells transfected with truncated tau (10% vs 47%, p<0.001), and the differential effect of truncated tau was itself significant (p=0.005). Thus, transfection with truncated tau accentuated the formation of pNFH aggregates in response to db-cAMP.

The effect of withdrawal of thionine after db-cAMP treatment was to double the frequency of cells with pNFH aggregates (27% vs 49%, p=0.05). These increases were seen for cells transfected with both full-length tau (16% vs 32%) and truncated tau (36% vs 60%). A further effect was thionine-dependent incorporation of pNFH immunoreactivity into neurites. This was particularly evident in PC-12 cells transfected with truncated, but not full-length tau or untransfected cells (pNFH-neurite indices 0.49 vs 0.04 with and without thionine respectively, p=0.07).

B. NIE-115 Cells

In general, pNFH aggregates seen in the cytoplasm of N2A cells did not occur in untransfected NIE cells. Rather, pNFH immunoreactivity was normally incorporated into growing neurites during the course of differentiation. although an early perinuclear-arc stage was also seen. NIE cells were transfected as above with the pIF2 vector containing either full-length or truncated tau protein and grown in the presence of thionine. The effects of adding db-cAMP in the presence or absence of thionine were then examined.

As with PC-12 cells, no stable NIE cells transfected with truncated tau were produced in the absence of thionine. Those transfected with truncated tau produced a significantly higher overall frequency of pNFH aggregates in the cytoplasm than cells transfected with full-length tau (9% vs 26%, p<0.001), and incubation with db-cAMP induced pNFH aggregates in cells transfected with truncated tau but not in full-length tau transfectants (6% vs 36%, p<0.001).

In cells transfected with full-length tau, the presence of thionine did not interfere with the incorporation of transgenic tau protein into the microtubular cytoskeleton, including the microtubule organising centre, diffuse cytoplasmic distribution and extension into neurites. Withdrawal of thionine in cells transfected with full-length tau increased the proportion containing pNFH aggregates (7% vs 16%, p=0.03). In cells transfected with truncated tau thionine withdrawal resulted in increased pNFH aggregates in specific cell lines (e.g. NIE-ND6, 14% vs 44%. p=0.07), which were also characterised by suppression of differentiation. This revision to a phenotype previously seen only in undifferentiated N2A cells, but not in NIE cells was striking.

As with PC-12 cells, thionine-dependent incorporation of pNFH into neurites could be demonstrated after db-cAMP treatment in certain cells (e.g. NIE-ND1, pNFH-neurite indices 0.1 vs 0.66 with and without thionine respectively, p=0.01). Thionine-dependent transport of pNFH into neurites could be seen quantitatively as a reversal of the relationship between cytoplasmic and neuritic neurofilament NHF immunoreactivity in transfected cell in the presence of thionine (r=−0.52 vs r=+0.52 without and with thionine; p=0.01 and 0.02 respectively).

What is claimed is:

1. A method for the treatment of Alzheimer's disease, motor neurone disease, Lewy body disease, Pick's disease, or progressive supranuclear palsy, which method comprises administering to a subject in need thereof an effective amount of an agent which modulates or inhibits tau-tau association and which does not inhibit tau-tubulin binding.

2. A method according to claim 1 for the treatment of Alzheimer's disease.

3. A method according to claim 1 wherein said agent phenothiazines of the formulae:

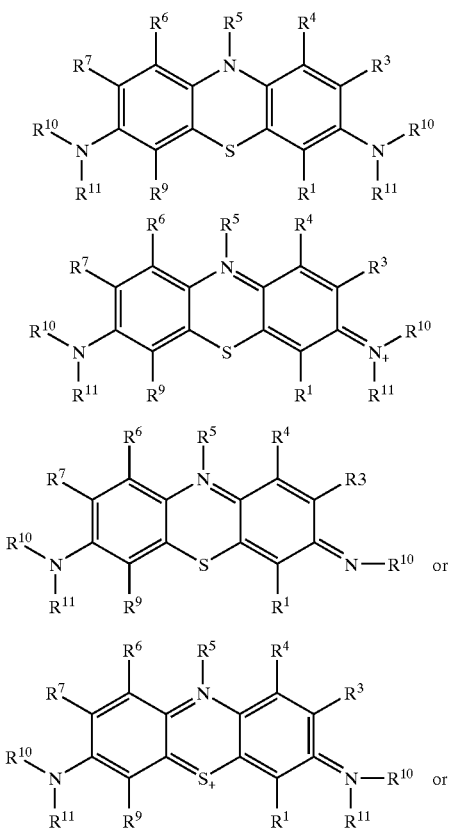

wherein:
   $R_1$, $R_3$, $R_4$, $R_6$, $R_7$ and $R_9$ are independently selected from hydrogen, halogen, hydroxy, carboxy, substituted or unsubstituted alkyl, haloalkyl or alkoxy;
   $R_5$, each $R_{10}$ and each $R_{11}$ are independently selected from hydrogen, hydroxy, carboxy, substituted or unsubstituted alkyl, haloalkyl or alkoxy; and pharmaceutically acceptable salts thereof.

4. A method according to claim 3 wherein: $R_1$, $R_3$, $R_4$, $R_5$, $R_6$, $R_7$, $R_9$, each $R_{10}$ and each $R_{11}$ are independently selected from hydrogen, —$CH_3$, —$C_2H_5$ or —$C_3H_7$.

5. A method according to claim 3 wherein said agent is a phenothiazine of the formula (I):

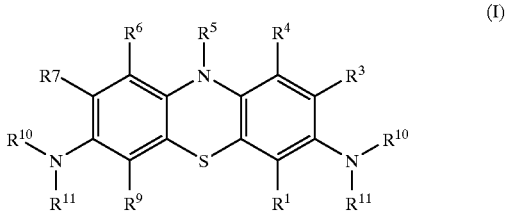

wherein:
   $R_1$, $R_3$, $R_4$, $R_6$, $R_7$ and $R_9$ are independently selected from hydrogen, halogen, hydroxy, carboxy, substituted or unsubstituted alkyl, haloalkyl or alkoxy;
   $R_5$, $R_{10}$ and $R_{11}$ are independently selected from hydrogen, hydroxy, carboxy, substituted or unsubstituted alkyl, haloalkyl or alkoxy; and pharmaceutically acceptable salts thereof.

6. A method according to wherein $R_5$ is hydrogen.

7. A method according to claim 4 wherein said compound is selected from Methylene Blue, Toluidine Blue O, thionine, Azure A, Azure B or 1,9-dimethyl-Methylene Blue.

8. A method according to claim 3 wherein the agent is present in a therapeutically effective amount in a therapeutically inert carrier material in a pharmaceutical composition.

9. A method according to claim 3 wherein the agent has a standardized tau binding coefficient of less than 0.4 in the range 1–10 μg/ml, and does not inhibit tau-tubulin binding up to a molar ratio of 1000:1 with respect to the molar concentration of tau.

* * * * *